United States Patent [19]

Goulet et al.

[11] Patent Number: 5,756,507
[45] Date of Patent: May 26, 1998

[54] ANTAGONISTS OF GONADOTROPIN RELEASING HORMONE

[75] Inventors: Mark Goulet, Westfield; Lin Chu, Scotch Plains; Wallace T. Ashton, Clark; Michael H. Fisher, Ringoes; Matthew J. Wyvratt, Mountainside; Roy G. Smith, Westfield; Robert L. Bugianesi, Colonia; Mitree M. Ponpipom, Branchburg; Yi Tien Yang, Neshanic Station; Peter Lin, Edison, all of N.J.

[73] Assignee: Merck & Co., Inc., Rahway, N.J.

[21] Appl. No.: 760,851

[22] Filed: Dec. 5, 1996

Related U.S. Application Data

[60] Provisional application No. 60/008,632, Dec. 14, 1995.

[51] Int. Cl.$^6$ .............. A61K 31/405; A61K 31/495; C07D 209/10; C07D 403/06
[52] U.S. Cl. .............. 514/255; 514/278; 514/322; 514/323; 514/415; 514/419; 544/373; 546/17; 546/199; 546/201; 548/495; 548/496; 548/504
[58] Field of Search .............. 548/495, 496, 548/504; 514/415, 419, 278, 322, 323, 255; 546/17, 199, 201; 544/373

[56] References Cited

U.S. PATENT DOCUMENTS

| | | | |
|---|---|---|---|
| 4,252,803 | 2/1981 | Webb | 424/248.5 |
| 4,544,663 | 10/1985 | Manning et al. | 514/378 |
| 5,030,640 | 7/1991 | Fisher et al. | 514/339 |

FOREIGN PATENT DOCUMENTS

| | | |
|---|---|---|
| 0219292 | 4/1987 | European Pat. Off. . |
| 0679642 A1 | 11/1995 | European Pat. Off. . |
| 2181559 | 4/1972 | France . |
| WO 90/05721 | 10/1989 | WIPO . |
| WO 95/28405 | 4/1995 | WIPO . |
| WO 95/29900 | 4/1995 | WIPO . |

OTHER PUBLICATIONS

Biswanath De, et al. *J. Med. Chem.*; 32, pp. 2036–2038 (1989).

*Primary Examiner*—Joseph McKane
*Attorney, Agent, or Firm*—Elliott Korsen; Mark R. Daniel

[57] ABSTRACT

There are disclosed compounds of formula (I)

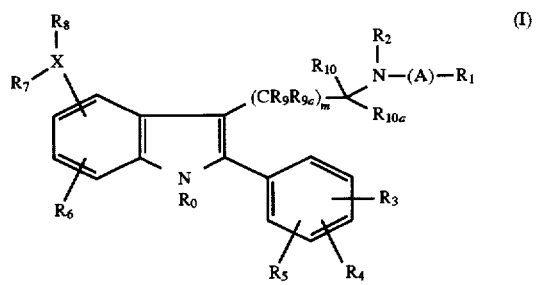

and pharmaceutically acceptable salts thereof which are useful as antagonists of GnRH and as such may be useful for the treatment of a variety of sex-hormone related and other conditions in both men and women.

38 Claims, No Drawings

ANTAGONISTS OF GONADOTROPIN RELEASING HORMONE

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus. The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4, 7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral administration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Substituted indoles known in the art include those described in the following patents and patent applications. U.S. Pat. No. 5,030,640 discloses alpha-heterocyclic ethanol aminoalkyl indoles which are potent β-agonists. U.S. Pat. No. 4,544,663 discloses indolamine derivatives which are allegedly useful as male anti-fertility agents. WO 90/05721 discloses alpha-amino-indole-3-acetic acids useful as antidiabetic, anti-obesity and anti-atherosclerotic agents. French patent 2,181,559 discloses indole derivatives with sedative, neuroleptic, analgesic, hypotensive, antiserotonin and adrenolytic activity. Belgian patent 879381 discloses 3-aminoalkyl-1H-indole-5-thioamide and carboxamide derivatives as cardiovascular agents used to treat hypertension, Raynaud's disease and migraine.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertrophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, for the treatment and the prevention of disturbances of calcium, phosphate and bone metabolism, in particular, for the prevention of bone loss during therapy with the GnRH antagonist, and in combination with estrogens, progesterones and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4, 7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

DETAILED DESCRIPTION OF THE INVENTION

The present invention relates to compounds of the general formula

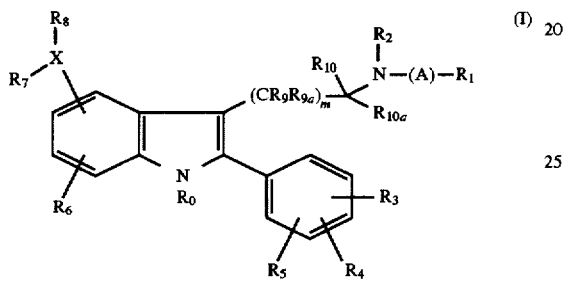

wherein

A is $C_1-C_6$ alkyl, substituted $C_1-C_6$ alkyl, $C_3-C_7$ cycloalkyl, substituted $C_3-C_7$ cycloalkyl, $C_3-C_6$ alkenyl, substituted $C_3-C_6$ alkenyl, $C_3-C_6$ alkynyl, substituted $C_3-C_6$ alkynyl, $C_1-C_6$ alkoxy, or $C_0-C_5$ alkyl-$S(O)_n$—$C_0-C_5$ alkyl, $C_0-C_5$ alkyl-O—$C_0-C_5$ alkyl, $C_0-C_5$ alkyl-$NR_{18}$—$C_0-C_5$ alkyl where $R_{18}$ and the $C_0-C_5$ alkyl can be joined to form a ring,

or a single bond;

$R_0$ is hydrogen, $C_1-C_6$ alkyl, substituted $C_1-C_6$ alkyl, wherein the substituents are as defined below; aryl, substituted aryl, aralkyl or substituted aralkyl, wherein the substituents are as defined for $R_3$, $R_4$ and $R_5$;

$R_1$ is

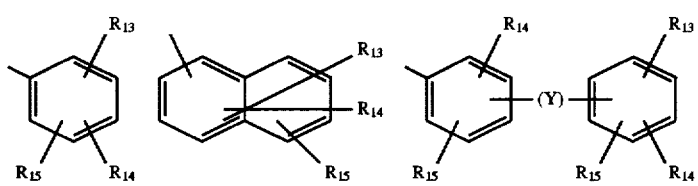

wherein:
Y is B, C or a bond;
B is O, $S(O)_n$, C(O), $NR_{18}$ or $C(R_{11}R_{12})_p$
C is $B(CH_2)_p$—;
$R_2$ is hydrogen, $C_1-C_6$ alkyl, substituted $C_1-C_6$ alkyl, aralkyl, substituted aralkyl, aryl, substituted aryl, alkyl —$OR_{11}$, $C_1-C_6(NR_{11}R_{12})$, $C_1-C_6(CONR_{11}R_{12})$ or $C(NR_{11}R_{12})NH$;

$R_2$ and A taken together form a ring of 5-7 atoms;

$R_3$, $R_4$ and $R_5$ are independently hydrogen, $C_1-C_6$ alkyl, substituted $C_1-C_6$ alkyl, $C_2-C_6$ alkenyl, substituted $C_2-C_6$ alkenyl, CN, nitro, $C_1-C_3$ perfluoroalkyl, $C_1-C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1-C_6$ alkyl, $C_1-C_3$ perfluoroalkyl, aryl or substituted aryl;

$R_3$ and $R_4$ taken together form a carbocyclic ring of 3-7 carbon atoms or a heterocyclic ring containing 1-3 heteroatoms selected from N, O and S;

$R_6$ is hydrogen, $C_1-C_6$ alkyl, substituted $C_1-C_6$ alkyl, aryl, substituted aryl, $C_1-C_3$ perfluoroalkyl, CN, $NO_2$, halogen, $R_{11}O(CH_2)_p$—, $NR_{12}C(O)R_{11}$, $NR_{12}C(O)NR_{11}R_{12}$ or $SO_nR_{11}$;

$R_7$ is hydrogen, $C_1-C_6$ alkyl, or substituted $C_1-C_6$ alkyl, unless X is hydrogen or halogen, then $R_7$ is absent;

$R_8$ is hydrogen, $C(O)OR_9$, $C(O)NR_{11}R_{12}$, $NR_{11}R_{12}$, $C(O)R_{11}$, $NR_{12}C(O)R_{11}$, $NR_{12}C(O)NR_{11}R_{12}$, $NR_{12}S(O)_2R_{11}$, $NR_{12}S(O)_2NR_{11}R_{12}$, $OC(O)R_{11}$, $OC(O)NR_{11}R_{12}$, $OR_{11}$, $SO_nR_{11}$, $S(O)_nNR_{11}R_{12}$, $C_1-C_6$ alkyl or substituted $C_1-C_6$ alkyl, unless X is hydrogen or halogen, then $R_8$ is absent; or $R_7$ and $R_8$ taken together form a carbocyclic ring of 3-7 atoms;

$R_9$ and $R_{9a}$ are independently hydrogen, $C_1-C_6$ alkyl, substituted $C_1-C_6$ alkyl; aryl or substituted aryl, aralkyl or substituted aralkyl when m≠0; or $R_9$ and $R_{9a}$ taken together form a carbocyclic ring of 3-7 atoms or $$\overset{O}{\underset{\|}{}}$$

when m≠0;

$R_9$ and A taken together form a heterocyclic ring containing 3-7 carbon atoms and one or more heteroatoms when m≠0; or $R_{10}$ and $R_{10a}$ are independently hydrogen, $C_1-C_6$ alkyl, substituted $C_1-C_6$ alkyl, aryl, substituted aryl, aralkyl or substituted aralkyl; or $R_{10}$ and $R_{10a}$ taken together form a carbocyclic ring of 3-7 atoms or $$\overset{O}{\underset{\|}{}}$$

;

$R_9$ and $R_{10}$ taken together form a carbocyclic ring of 3-7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms;

$R_{10}$ and A taken together form a heterocyclic ring containing 3–7 carbon atoms and one or more heteroatoms; or $R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl); $SO_2NR_{11}(C_1$–$C_6$ alkyl), $SO_2NR_{11}$(substituted $C_1$–$C_6$ alkyl), $SO_2NR_{11}$(aryl), $SO_2NR_{11}$(substituted aryl), $SO_2NR_{11}(C_1$–$C_3$ perfluoroalkyl); $SO_2NR_{11}(C(O)C_1$–$C_6$ alkyl); $SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl); $S(O)_n$ (substituted $C_1$–$C_6$ alkyl), $S(O)_n$(aryl), $S(O)_n$ (substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_{16}$ is hydrogen, $C_1$–$C_6$ alkyl, substituted $C_1$–$C_6$ alkyl, or $N(R_{11}R_{12})$;

$R_{18}$ is hydrogen, $C_1$–$C_6$ alkyl, substituted $C_1$–$C_6$ alkyl, $C(O)OR_9$, $C(O)NR_{11}R_{12}$, $C(O)R_{11}$, $S(O)_nR_{11}$;

X is hydrogen, halogen, N, O, $S(O)_n$, $C(O)$, $(CR_{11}R_{12})_p$; $C_2$–$C_6$ alkenyl, substituted $C_2$–$C_6$ alkenyl, $C_2$–$C_6$ alkynyl, or substituted $C_2$–$C_6$ alkynyl; when X is hydrogen or halogen, $R_7$ and $R_8$ are absent; when X is O, $S(O)_n$, $C(O)$, or $CR_{11}R_{12}$ only $R_7$ or $R_8$ is possible;

m is 0–3;

n is 0–2;

p is 0–4; and the alkyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

The term "aryl" includes phenyl and naphthyl. Preferably, aryl is phenyl.

The term "halogen" or "halo" is intended to include fluorine, chlorine, bromine and iodine.

The term "heterocycle" or "heterocyclic ring" is defined by all non-aromatic, heterocyclic rings of 3–7 atoms containing 1–3 heteroatoms selected from N, O, and S, such as oxirane, oxetane, tetrahydrofuran, tetrahydropyran, pyrrolidine, piperidine, tetrahydropyridine, tetrahydropyrimidine, tetrahydrothiophene, tetrahydrothiopyran, morpholine, hydantoin, valerolactam, pyrrolidinone, and the like.

As used herein, the term "composition" is intended to encompass a product comprising the specified ingredients in the specified amounts, as well as any product which results, directly or indirectly, from combination of the specified ingredients in the specified amounts In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared by the following reaction schemes. All substituents are as defined above unless indicated otherwise.

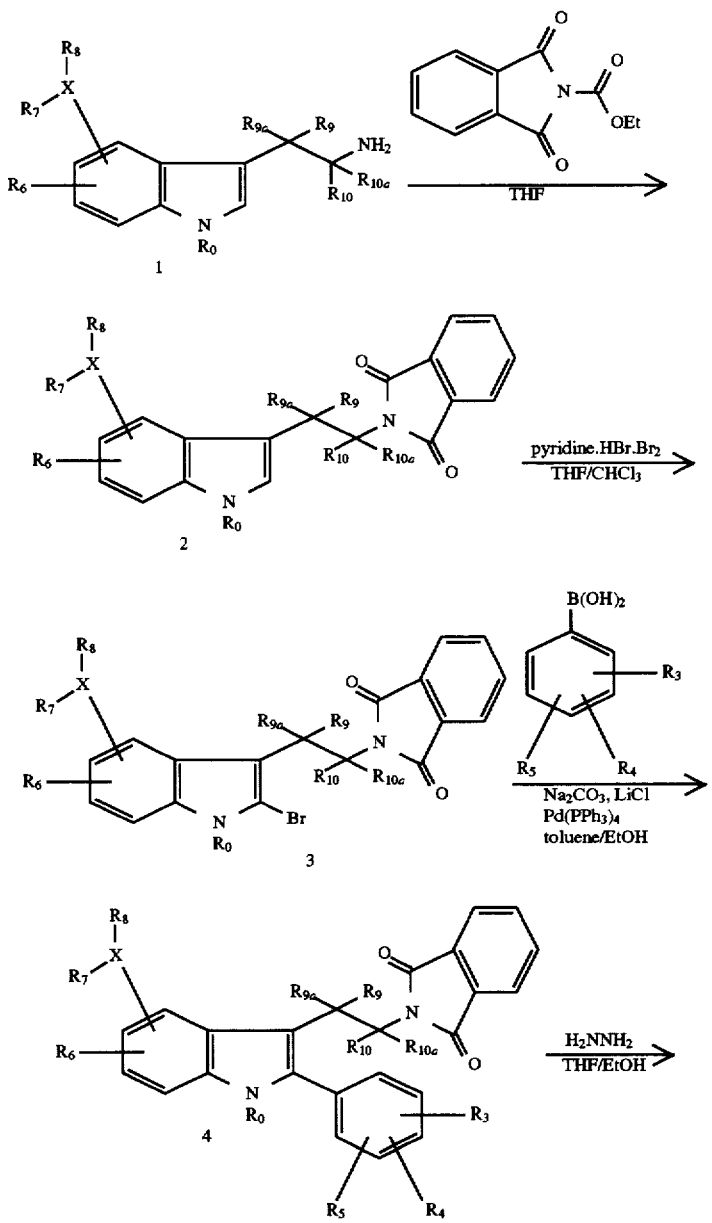

-continued
Scheme A

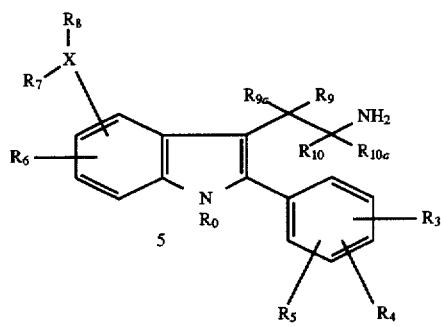

Reaction Scheme A

As shown in reaction Scheme A, treatment of tryptamine (1) with N-carboxyphthalimide in an inert organic solvent such as tetrahydrofuran at a temperature of 20°–65° C., preferably 65° C., for a period of 12–48 hours gives the corresponding N-phthalimidotryptamine derivative (2). The N-phthalimidotryptamine (2) could be further modified by treatment with a brominating agent such as pyridinium hydrobromide perbromide, pyrrolidone hydrotribromide, or the like in an inert organic solvent such as tetrahydrofuran, methylene chloride, chloroform, or mixtures thereof at 0°–25° C. for a period of 30 minutes to 4 hours to provide the 2-bromotryptamine (3). Bromide (3) may be reacted with an arylboronic acid (prepared essentially as described in: Gronowitz, S.; Hornfeldt, A.-B.; Yang, Y.-H. *Chem. Scr.* 1986, 26, 311–314.) with palladium (0) catalysis, a weak base such as aqueous sodium carbonate or the like, and a chloride source such as lithium chloride in an inert solvent like toluene, benzene, ethanol, propanol or mixtures thereof at a temperature of 25°–100° C., preferably 80° C., for a period of 1–6 hours to give the 2-aryltryptamine derivative (4). Finally, the phthalimido group may be removed by treatment of (4) with aqueous hydrazine in an inert solvent such as methanol or ethanol at a temperature of 0°–25° C. for a period of 4–24 hours to give tryptamine (5).

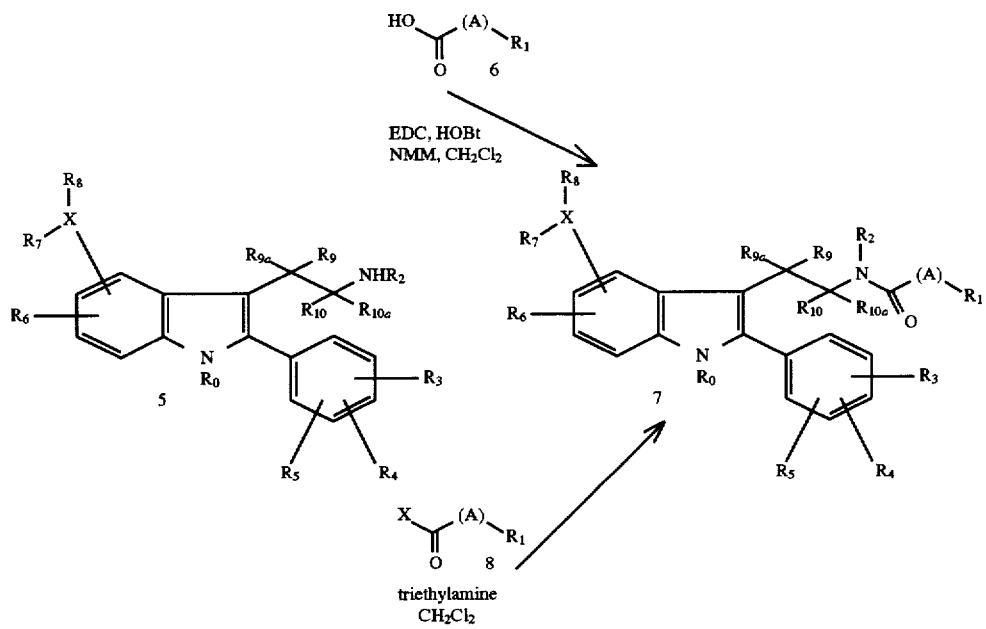

Reaction Scheme B

As shown in reaction Scheme B, the 2-aryltryptamine may be condensed with a carboxylic acid of type (6) using the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours to provide the corresponding amide derivative (7). Alternatively, 2-aryltryptamine (5) can be treated with an active ester or acid chloride of type (8) in an inert organic solvent such as methylene chloride, chloroform, tetrahydrofuran, diethyl ether, or the like and a tertiary amine base such as triethylamine, diisopropylethylamine, pyridine or the like at a temperature of 0°–25° C. for 30 minutes to 4 hours to give (7).

Scheme C

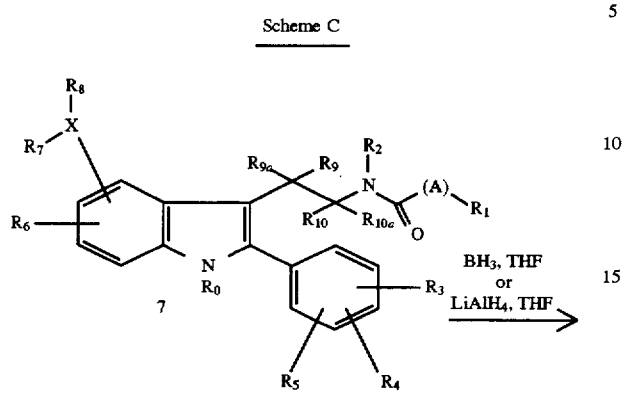

Reaction Scheme C

As shown in reaction Scheme C, the amide carbonyl of (7) can be reduced by treatment with borane, lithium aluminum hydride, or equivalent hydride sources in an inert organic solvent such as tetrahydrofuran, diethyl ether, 1,4-dioxane or the like at 25°–100° C., preferably 65° C., for a period of 1–8 hours to give the corresponding amine compound (9).

Scheme D

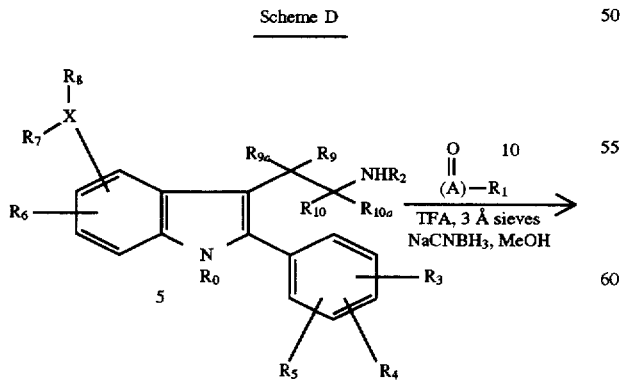

-continued
Scheme D

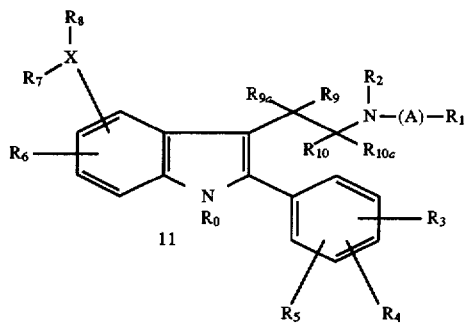

Reaction Scheme D

As shown in reaction Scheme D, the 2-aryltryptamine (5) can be modified by treatment with an aldehyde or ketone of type (10) in the presence of a weak acid such as trifluoroacetic acid (TFA), acetic acid or the like, with or without a dessicant such as 3 Å molecular sieves or magnesium sulfate, and a hydride source such as sodium borohydride or sodium cyanoborohydride, in an inert organic solvent such as methanol, ethanol, isopropanol, tetrahydrofuran, dichloromethane, chloroform, or mixtures thereof at a temperature of 0°–25° C. for a period of 1–12 hours to give the corresponding secondary or tertiary amine derivative (11).

Scheme E

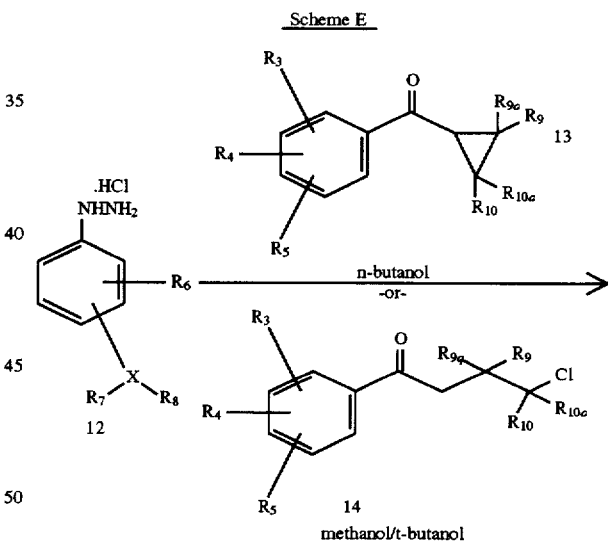

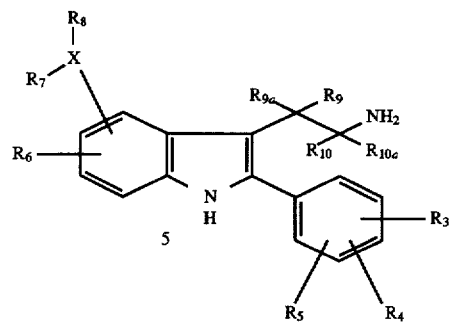

Reaction Scheme E

As shown in reaction Scheme E, treatment of an arylhydrazine or arylhydrazine hydrochloride (12) with an arylcyclopropylketone of type (13) in a polar organic solvent such as methanol, ethanol, n-propanol, isopropanol, n-butanol, t-butanol, preferably n-butanol, at a temperature of 70°–120° C. for a period of 8–24 hours gives 2-aryltryptamine (5). Alternatively, when an arylhydrazine or arylhydrazine hydrochloride (12) is treated with an arylbutyl ketone of type (14) containing a leaving group (chloride, bromide, iodide, O-methansulfonate, O-trifluoromethansulfonate, or the like) at the 4-position in a polar solvent such as methanol, ethanol, n-propanol, isopropanol, n-butanol, t-butanol, or mixtures thereof at room temperature for a period of 30 minutes to 2 hours followed by heating to a temperature of 65°–100° C. for 4–24 hours, 2-aryltryptamine (5) is produced.

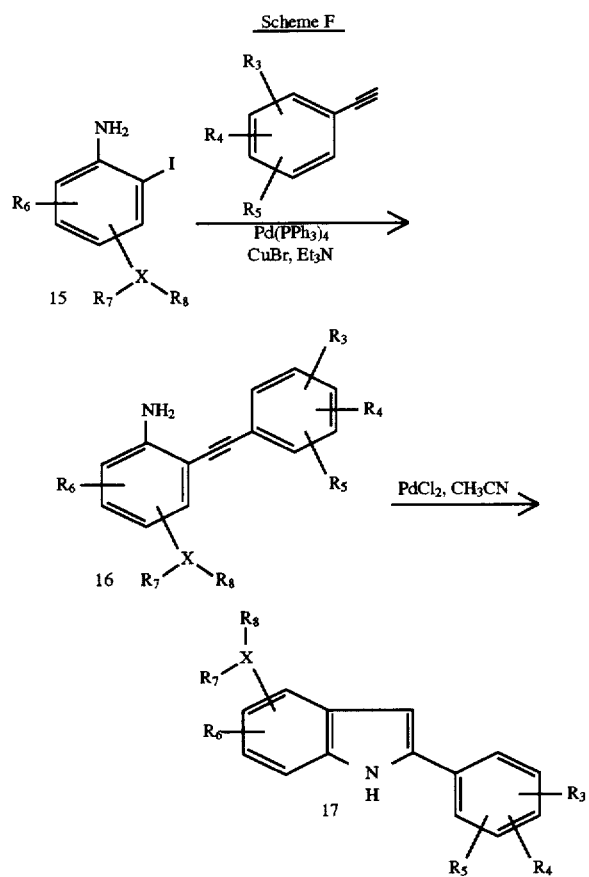

Reaction Scheme F

As shown in reaction Scheme F, iodoanilines of type (15) may be reacted with aryl acetylenes, an appropriate palladium (0) catalyst such as tetrakis(triphenylphosphine) palladium, a copper (I) halide such as cuprous bromide in an inert organic solvent such as triethylamine at a temperature of 50°–88° C. for a period of 30 minutes to 5 hours to provide the diarylacetylene (16). Acetylene (16) may be further modified by treatment with a palladium (II) catalyst such as palladium (II) chloride or palladium (II) acetate in an inert organic solvent such as acetonitrile at a temperature of 50°–82° C. for a period of 30 minutes to 6 hours to give 2-arylindole (17).

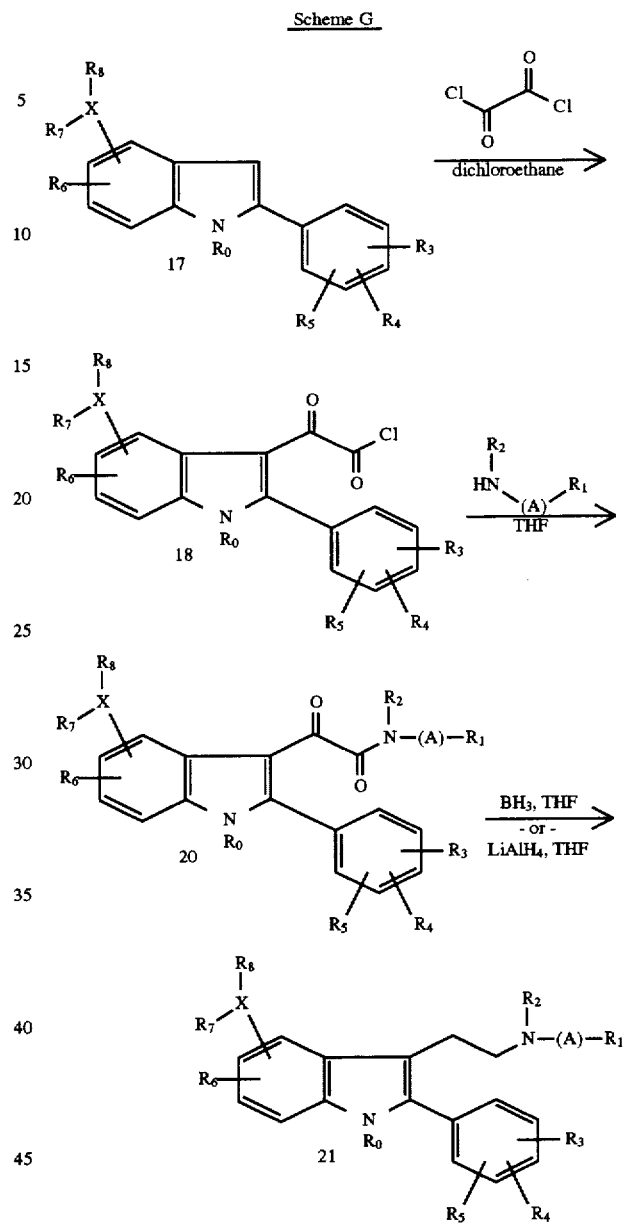

Reaction Scheme G

As shown in reaction Scheme G, treatment of 2-arylindole (17) with oxalyl chloride neat or in an inert organic solvent such as methylene chloride, chloroform, dichloroethane, tetrahydrofuran or the like at a temperature of 25°–65° C. for a period of 3–24 hours gives the acylchloride adduct (18). The crude product (18) may be reacted with an amine of type (19) in an inert organic solvent such as diethylether, tetrahydrofuran, methylene chloride, chloroform or the like and an amine base such as triethylamine, diisopropylethylamine or pyridine at a temperature of 0° C.–25° C. for a period of 30 minutes to 4 hours to provide the amide derivative (20). Amide (20) may be further modified by treatment with a reducing agent such as borane or lithium aluminum hydride in an inert organic solvent such as tetrahydrofuran at elevated temperatures, preferably reflux, for a period of 1–5 hours to give compound (21).

Scheme H

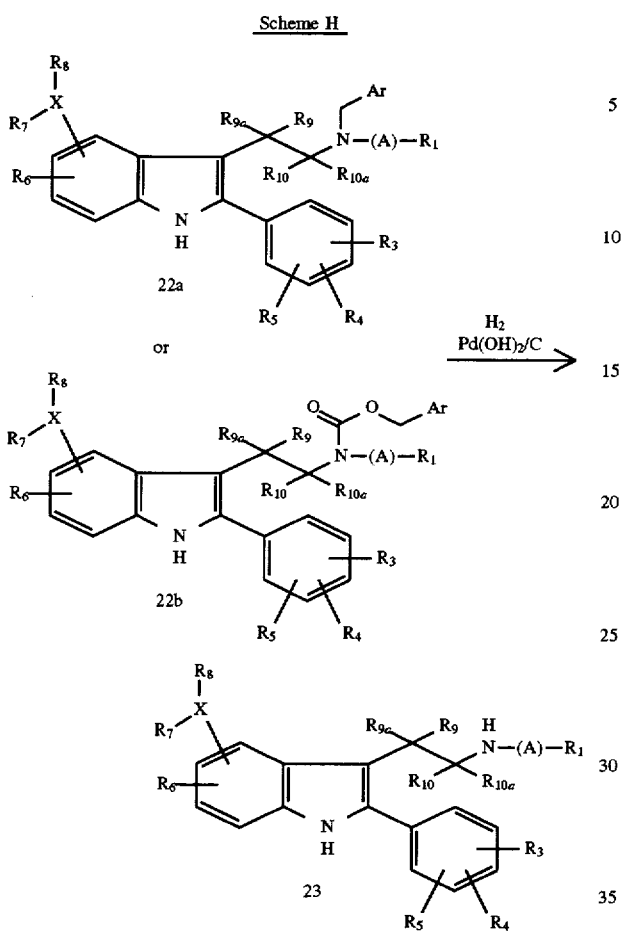

Reaction Scheme H

As shown in reaction Scheme H, N-benzyl derivatives of type (22a) or N-benzyloxycarbonyl derivatives of type (22b) may be reduced to provide the secondary amine analogs (7) by treatment with hydrogen (1 atm) and an appropriate catalyst such as palladium on carbon, palladium hydroxide on carbon, or the like in an inert organic solvent such as tetrahydrofuran, ethyl acetate, methanol, ethanol, or mixtures thereof to which has been added a weak acid such as 30% aqueous acetic acid for a period of 10 minutes to 3 hours or until the aryl group has been removed to give the secondary amine.

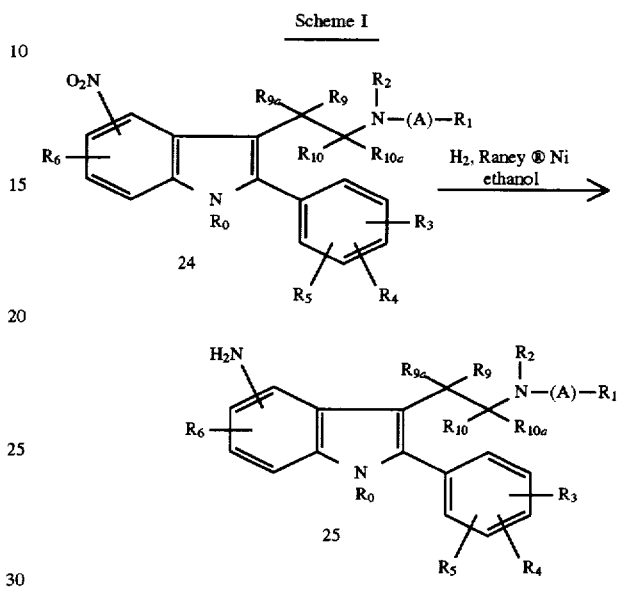

Reaction Scheme I

As shown in reaction Scheme I, treatment of a nitroindole of type (24) with hydrogen (1 atm) and an appropriate catalyst such as Raney® Nickel in an inert organic solvent such as ethanol, methanol, or the like at room temperature for a period of 2–12 hours gives the corresponding aminoindole derivative (25).

Scheme J

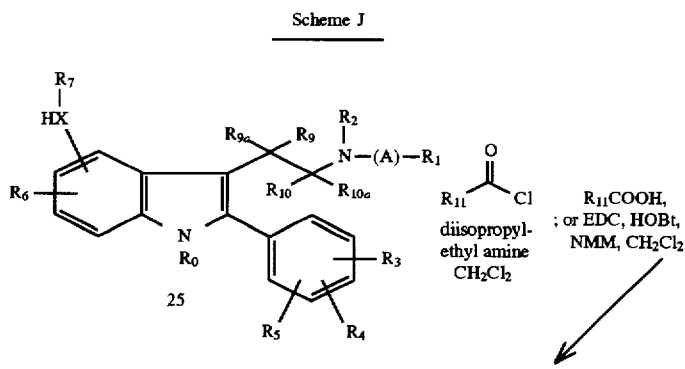

-continued
Scheme J

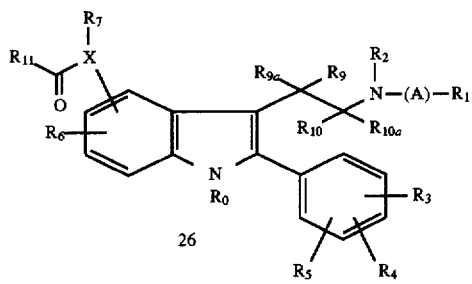

26

Reaction Scheme J

As shown in reaction Scheme J, amino- or hydroxyindole (25) may be modified by acylation under a variety of conditions. For example, treatment of (25) with an acid chloride, acid anhydride or active ester and an amine base such as triethylamine, diisopropylethylamine, pyridine, or the like in an inert organic solvent such as methylene chloride, chloroform, tetrahydrofuran, or mixtures thereof at 0° C. to room temperature for a period of 1 to 12 hours gives the corresponding amide or ester derivatives (26). Alternatively (25) may be coupled with a carboxylic acid by one of the many dehydrating agents commonly employed. For instance, treatment of aminoindole (25) with an appropriate carboxylic acid and 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours provides the corresponding amide or ester derivative (26).

Reaction Scheme K

As shown in reaction Scheme K, urea or carbamate derivatives of (25) can be prepared by treatment with a carbamoyl chloride of type (27a), or alternatively with an isocyanate reagent of type (27b), and an amine base such as pyridine, triethylamine, diisopropylethylamine, N-methylmorpholine or the like in an inert organic solvent such as methylene chloride, chloroform, dimethylformamide, tetrahydrofuran or mixtures thereof at a temperature of 0°–65° C. for a period of 1–72 hours to give (28).

Compound (25) can also be modified by treatment with a bis(electrophilic) reagent such as phosgene, triphosgene, 1,1'-carbonyldiimidazole, N,N'-disuccinimidyl carbonate, or the like with or without the addition of an amine base such as pyridine, triethylamine, diisopropylethylamine, N-methylmorpholine in an inert solvent such as methylene chloride, chloroform, or the like at a temperature of −20°–0° C. for a period of 20 minutes to 2 hours. After this time, the reaction mixture is treated with an appropriate mono- or disubstituted amine at −20°–25° C. for a period of 1–5 hours to give the urea or carbamate analog (28).

Scheme K

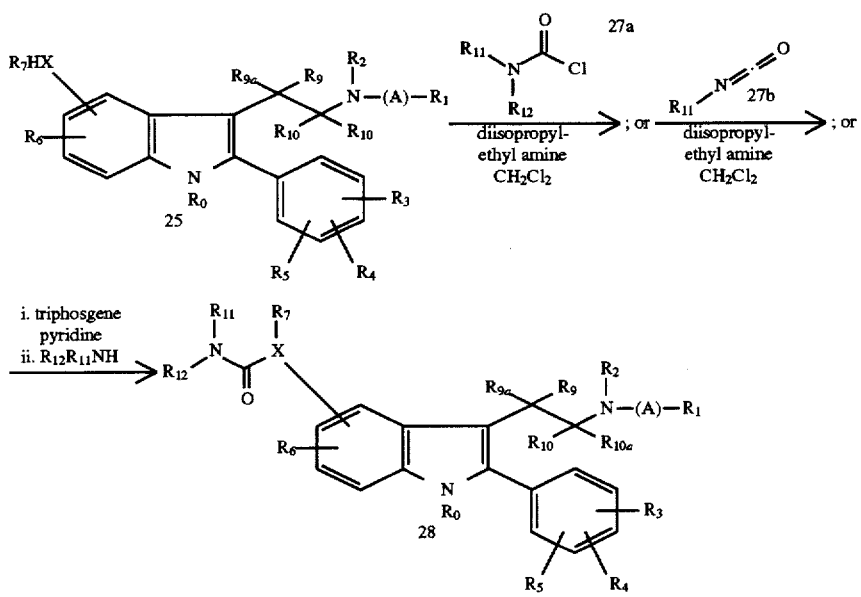

Scheme L

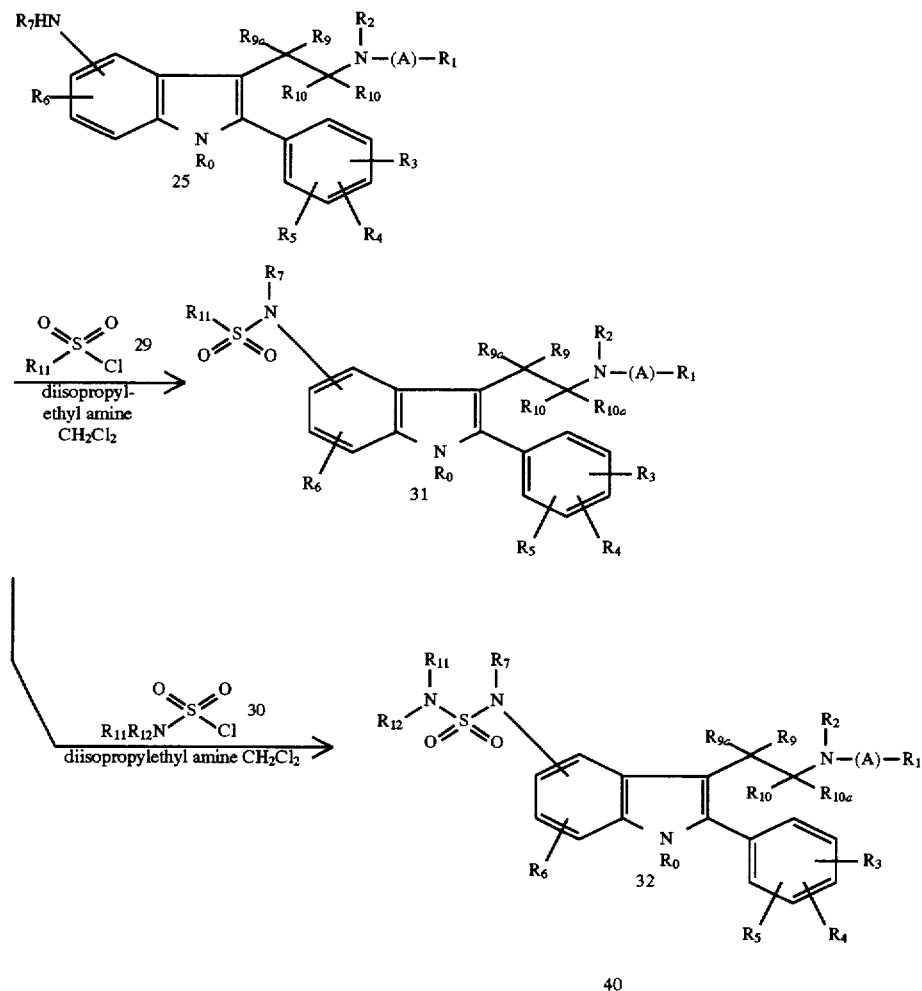

Reaction Scheme L

As shown in reaction Scheme L, amine (25) can be modified by treatment with an appropriate sulfonyl chloride of type (29) or sulfamyl chloride of type (30) with an amine base such as pyridine, triethylamine, diisopropylethylamine, N-methylmorpholine in an inert solvent such as methylene chloride, chloroform, dichloroethane or the like at a temperature of −20°–25° C. for a period of 20 minutes to 2 hours to give the corresponding N-sulfonamide (31) or N-sulfamylamide (32) derivatives, respectively.

Scheme M

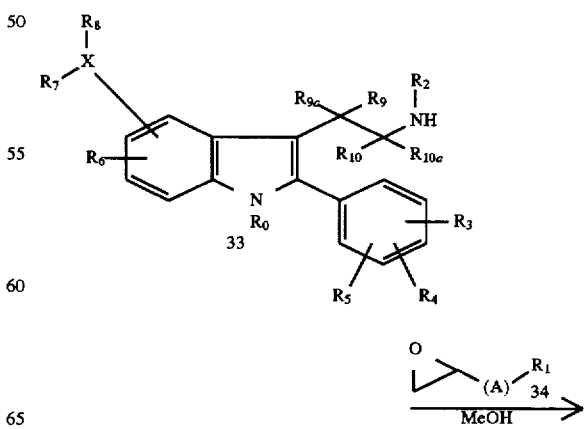

-continued
Scheme M

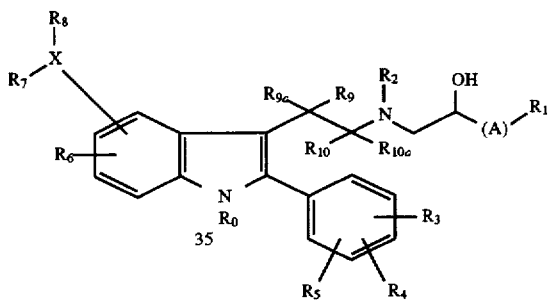

Reaction Scheme M

As shown in reaction Scheme M, the 2-aryltryptamine (33) can be modified by treatment with an epoxide such as (34) in an inert organic solvent such as methanol, ethanol, isopropanol, butanol, tertbutanol, or mixtures thereof at a temperature of 65°–110° C. for a period of 8–20 hours to give the corresponding amino-alcohol derivative (35).

Scheme N

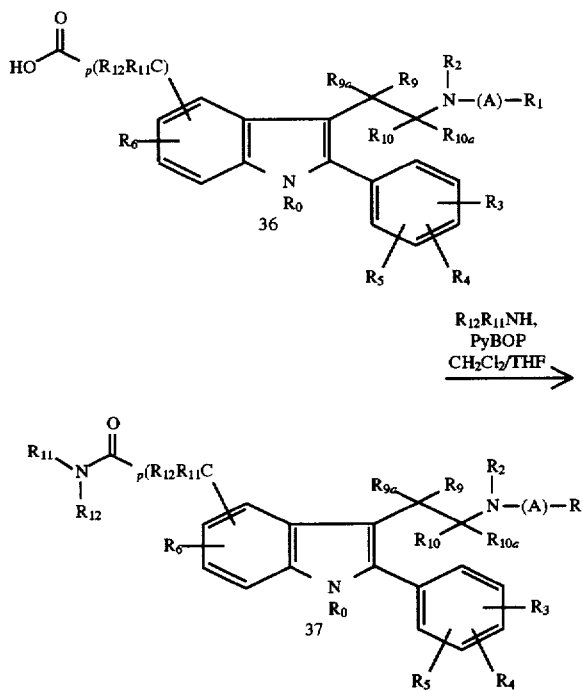

Reaction Scheme N

As shown in reaction Scheme N, amide derivatives of an acid-containing indole derivative such as (36) can be prepared by treatment with an appropriate amine ($R_{12}R_{11}NH$) and a suitable coupling agent such as benzotriazol-1-yloxy-tris(pyrrolidino)phosphonium hexafluorophosphate (PyBOP), benzotriazol-1-yloxy-tris(dimethylamino) phosphonium hexafluorophosphate (BOP), 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, tetrahydrofuran, dimethylformamide, or mixtures thereof at or near room temperature for a period of 3–24 hours provides the corresponding amide derivative (37).

The compounds of the present invention are useful in the treatment of various sex-hormone related conditions in men and women. This utility is manifested in their ability to act as antagonists of the neuropeptide hormone GnRH as demonstrated by activity in the following in vitro assays.

Rat pituitary GnRH receptor binding assay

Crude plasma membranes prepared from rat pituitary tissues were incubated in a Tris.HCl buffer (50 mM, PH. 7.5) containing bovine serum albumin (0.1%), [I-125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LH release assay

Active compounds from the GnRH receptor binding assay were further evaluated with an in vitro LH release assay to confirm their antagonist activity (blocking GnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (25° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-mL polypropylene centrifuge tube. The collection tube was centrifuged for 5 min at 250×g, and HBSS was removed by aspiration. Pituitary glands were transferred to a disposable petri plate and minced with a scalpel. The minced tissue was then transferred to a 50-mL disposable centrifuge tube by suspending the tissue fragments in three successive 10-mL aliquots of HBSS containing 0.2% collagenase and 0.2% hyaluronidase. The cell dispersion was carried out in a water bath at 37° C. with gentle stirring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200×g centrifugation for 5 min. The cells were then resuspended in Culture medium. The undigested pituitary fragments were treated with 30 mL aliquots of the digestion enzymes as above for a total of 3 digestions with the collagenase/hyaluronidase mixture. The resulting cell suspensions were pooled, counted and diluted to a concentration of $3 \times 10^5$ cells/ml, and 1.0 ml of this suspension was placed in each well of a 24-well tray (Costar, Cambridge, Mass.). Cells were maintained in a humidified 5% $CO_2$–95% air atmosphere at 37° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1% gentamycin. On the day of an experiment, cells were washed three times 1½ hrs prior to and two more times immediately before the start of the experiment with DMEM containing 0.37% NaHCO$_3$, 10% horse serum, 2.5% fetal bovine serum, 1% nonessential amino acids(100×), 1% glutamine(100×), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GnRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be useful in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (J. Endocrinol Invest., 15(Suppl 4), 45 (1992)). Other compounds which stimulate the release of endogenous growth hormone are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; Science, 260, 1640–1643 (Jun. 11, 1993); Ann. Rep. Med. Chem., 28, 177–186 (1993); Bioorg. Med. Chem. Ltrs., 4(22), 2709–2714 (1994); and Proc. Natl. Acad. Sci. USA 92, 7001–7005 (July 1995).

Representative preferred growth hormone secretagoues employed in the present combination include the following:

1) N-[1(R)-[(1,2-Dihydro-1-methanesulfonylspiro[3H-indole-3,4'-piperidin]-1'-yl)carbonyl]-2-(1H-indol-3-yl) ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(1H-indol-3-yl) ethyl]-2-amino-2-methylpropanamide;
3) N-[1(R)-[(1,2-Dihydro-1-benzenesulfonylspiro[3H-indole-3,4'-piperidin]-1'-yl)carbonyl]-2-(1H-indol-3-yl) ethyl]-2-amino-2-methylpropanamide;
4) N-[1(R)-[(3,4-Dihydro-spiro[2H-1-benzopyran-2,4'-piperidin]-1'-yl)carbonyl]-2-(1H-indol-3-yl)ethyl]-2-amino-2-methylpropanamide;
5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methylpropanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-Dihydro-1-methanesulfonyl-5-fluorospiro[3H-indole-3,4'-piperidin]-1'-yl)carbonyl]-2-(phenylmethyloxy)ethyl]-2-amino-2-methylpropanamide;
10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;
11) N-[1(R)-[(1,2-Dihydro-1-methanesulfonylspiro[3H-indole-3,4'-piperidin]-1'-yl)carbonyl]-3-phenylpropyl]-2-amino-2-methylpropanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;
13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;
14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;
16) N-[1(R)-[(1,2-Dihydro-1-(2-ethoxycarbonyl)methylsulfonylspiro-[3H-indole-3,4'-piperidin]-1'-yl) carbonyl]-2-(1H-indol-3-yl)ethyl]-2-amino-2-methylpropanamide;
17) N-[1(R)-[(1,2-Dihydro-1,1-dioxospiro[3H-benzothiophene-3,4'-piperidin]-1'-yl)carbonyl]-2-

(phenylmethyloxy)ethyl]-2-amino-2-methylpropanamide;
and pharmaceutically acceptable salts thereof.

The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. No. 3,251,907; U.S. Pat. No. 3,422,137; U.S. Pat. No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,007; U.S. Pat. No. 4,942,157; U.S. Pat. No. 5,227,506; U.S. Pat. No. 5,270,365; EPO Patent Pub. No. 0,252,504; and *J. Org. Chem.*, 36, 3843 (1971).

The preparation of bisphosphonic acids and halobisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidenebisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE I

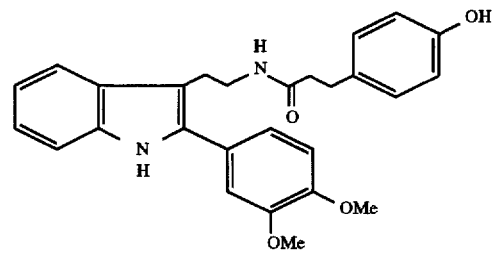

N-[2-[2-(3 4-dimethoxyphenyl)-1H-indol-3-yl]ethyl]-3-(4-hydroxyphenyl)propionamide To a stirred solution of 3-(4-hydroxyphenyl)propionic acid (80 mg in 4 mL N,N-dimethylformamide) was added 1-hydroxybenzotriazole (78 mg) and the mixture cooled to 0° C. After 10 minutes, 1-(3-dimethylaminopropyl)-3-ethylcarbodiimide hydrochloride (130 mg) was added. The mixture was warmed to room temperature and 2-[2-(3,4-dimethoxyphenyl)-1H-indol-3-yl]ethylamine (272 mg) was added. After 17 hours the reaction was quenched by the addition of water and extracted with ethyl acetate. The organic portion was washed with water, 0.5M sodium bisulfate and brine, dried over sodium sulfate and concentrated in vacuo. Purification by flash chromatography on silica gel (methylene chloride:methanol, 95:5) gave the title compound (227 mg). m/e=444 (M)

Following a procedure similar to that described in Example 1, the following intermediates were prepared:

| Example # | $R_1$ | $R_3, R_4, R_5$ | $(CH_2)_n = A$ | m/e |
|---|---|---|---|---|
| 1A | Ph-4-O—CH$_2$—Ph | 3,4-OMe | 3 | 505 (M + H) |
| 1B | Ph-4-OH | 3,4-OMe | 3 | 459 (M + H) |
| 1C | Ph-4-OH | 3,4-OMe | 1 | 431 (M + H) |
| 1D | Ph-3,4-Cl,Cl | 3,4-OMe | 1 | 483 (M) |
| 1E | Ph-4-F | 3,4-OMe | 1 | 433 (M + H) |
| 1F | Ph-4-NO$_2$ | 3,4-OMe | 3 | — |
| 1G | Ph-4-NH$_2$ | 3,4-OMe | 3 | 458 (M + H) |
| 1H | Ph-4-NO$_2$ | 3,4-OMe | 1 | — |
| 1I | Ph-4-NH$_2$ | 3,4-OMe | 1 | 430 (M + H) |
| 1J | Ph-4-OH | 3,5-OMe | 3 | — |
| 1K | Ph-4-OH | 3-Ph | 3 | 475 (M + H) |
| 1L | Ph-4-NH—COO-tBu | 3,5-Me | 3 | 526 (M + H) |
| 1M | Ph-4-NH$_2$ | 3,5-Me | 3 | 426 (M + H) |
| 1N | Ph-4-NO$_2$ | 3,5-Me | 3 | 456 (M + H) |
| 1O | Ph-4-OH | 3-SCH$_3$, 5-CH$_3$ | 3 | 459 (M + H) |
| 1P | Ph-4-SO$_2$NH$_2$ | 3,5-Me | 0 | 448 (M + H) |

EXAMPLE 2

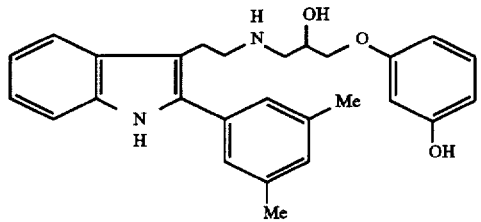

3-[3-[2-[2-(3,5-dimethylphenyl)-1H-indol-3-yl]ethylamino]-2-hydroxypropoxy]phenol Step 2A 2-[2-(1H-indol-3-yl)-ethyl]-isoindole-1,3-dione To a stirred suspension of 2-(1H-indol-3-yl)ethylamine (2.0 g in 20 mL of dry tetrahydrofuran) was added N-carbethoxyphthalimide (2.85 g) and the mixture heated to reflux on an oil bath. After 48 hours the reaction was cooled to room temperature, filtered and the filtrate concentrated in vacuo. The resulting solid was suspended in a mixture of hexane/methylene chloride (2.5:1) and filtered. Purification of the collected solids by flash chromatography on silica gel (methylene chloride:methanol, 97:3) gave the title compound (3.1 g).

Step 2B 2-[2-(2-bromo-1H-indol-3-yl)-ethyl]-isoindole-1,3-dione

To a solution of 2-[2-(1H-indol-3-yl)-ethyl]-isoindole-1,3-dione (1.0 g in a mixture of 10 mL dry tetrahydrofuran and 10 mL dry chloroform) at 0° C. was added pyridinium bromide perbromide (1.14 g) and the reaction stirred at 0° C. After 50 minutes, the reaction was quenched by the addition of saturated sodium bicarbonate and extracted with ethyl acetate. The organic portion was washed with saturated sodium bicarbonate (3×) and 0.3M sodium bisulfate (3×) then dried over magnesium sulfate. Purification of the concentrate by flash chromatography on silica gel (hexane:ethyl acetate, 3:1) gave the title compound (1.2 g).

Step 2C 2-{2-[2-(3,5-dimethylphenyl)-1H-indol-3-yl]-ethyl}-isoindole-1,3-dione

To a solution of 2-[2-(2-bromo-1H-indol-3-yl)-ethyl]-isoindole-1,3-dione (150 mg in a mixture of 5 mL toluene and 5 mL ethanol) was added 3,5-dimethylphenyl boronic acid (85 mg) followed by 1.0 mL of 1M sodium carbonate. To the stirred solution was added lithium chloride (60 mg) followed by tetrakis(triphenylphosphine) palladium (28 mg) and the mixture heated to reflux on an oil bath. After 4 hours the mixture was cooled to room temperature and concentrated in vacuo. Purification by flash chromatography on silica gel (hexane:ethyl acetate, 5:1) gave the title compound (146 mg).

Step 2D 2-[2-(3,5-dimethylphenyl)-1H-indol-3-yl]-ethylamine

To a solution of 2-{2-[2-(3,5-dimethylphenyl)-1H-indol-3-yl]-ethyl}-isoindole-1,3-dione (87 mg in a mixture of 4 mL tetrahydrofuran and 4 mL ethanol) was added 0.6 mL of 95% aqueous hydrazine and the reaction stirred at room temperature. After 18 hours the mixture was concentrated in vacuo and purified by flash chromatography on silica gel (methylene chloride:methanol:ammonium hydroxide, 9:6:1) to provide the title compound (54 mg).

Step 2E 3-[3-[2-[2-(3,5-dimethylphenyl)-1H-indol-3-yl]ethylaminol-2-hydroxypropoxyl]phenol (benzyl ether)

To a solution of 2-[2-(3,5-dimethylphenyl)-1H-indol-3-yl]-ethylamine (25.5 mg in 5 mL dry methanol) was added 12.1 mg of 1-[3-(benzyloxy)phenoxy]-2,3-epoxypropane and the mixture heated to reflux on an oil bath. After 7 hours the reaction mixture was cooled to room temperature, concentrated in vacuo and the product purified by flash chromatography on silica gel (methylene chloride:methanol, 95:5) to give the title compound (13.3 mg).

Step 2F 3-[3-[2-[2-(3,5-dimethylphenyl)-1H-indol-3-yl] ethylamino]-2-hydroxypropoxy]phenol To a solution of 3-[3-[2-[2-(3,5-dimethylphenyl)-1H-indol-3-yl]ethylamino]-2-hydroxypropoxylphenol (benzyl ether) (11 mg in 1 mL ethanol) was added 10 mg of 10% palladium hydroxide on carbon catalyst. The reaction flask was fitted with a hydrogen balloon, evacuated and recharged with hydrogen (3 times) and stirred at room temperature. After 2 hours the reaction was flushed with nitrogen, filtered over diatomaceous earth, concentrated in vacuo and purified by flash chromatography on silica gel (methylene chloride:methanol, 95:5) to provide the title compound (2.3 mg). m/e=431 (M+H)

Following a procedure similar to that described in Example 2, the following compounds were prepared:

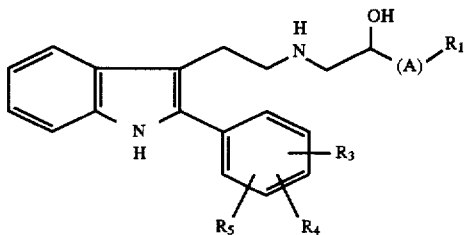

| Example # | R₁ | R₃,R₄,R₅ | A | m/e |
|---|---|---|---|---|
| 2A | Ph-4-OH | 3,4-OMe | (S) $CH_2$—O | |
| 2B | Ph-4-OH | 4-OMe | (S) $CH_2$—O | |
| 2C | Ph | 3,4-OMe | (S) $CH_2$—O | |
| 2D | Ph-4-OH | 3,4-OMe | (S) $CH_2$—$CH_2$ | |
| 2E | Ph-4-OH | 3,4-OMe | (R) $CH_2$ | |
| 2F | Ph-3-F, 4-NH2 | 3,4-OMe | (S) $CH_2$—O | |
| 2G | Ph-4-NHAc | 3,4-OMe | (S) $CH_2$—O | |
| 2H | Ph-4-NH2 | 3,4-OMe | (S) $CH_2$—O | |
| 2I | Ph-4-OH | 3,4-OMe | (R) $CH_2$—O | |
| 2J | Ph-4-F | 3,4-OMe | (S) $CH_2$—O | 465 (M + H) |
| 2K | Ph-4-Cl, 3-NH2 | 3,4-OMe | (S) $CH_2$—O | 496 (M + H) |
| 2L | Ph-4-O—$CH_2$—Ph, 3-NH—$COCH_3$ | 3,4-OMe | (S) $CH_2$—O | — |
| 2M | Ph-4-OH, 3-$NHCOCH_3$ | 3,4-OMe | (S) $CH_2$—O | 520 (M + H) |
| 2N | Ph-3-CN | 3,4-OMe | (S) $CH_2$—O | 472 (M + H) |
| 2O | Ph-3-$CH_2OH$ | 3,4-OMe | (S) $CH_2$—O | 477 (M + H) |
| 2P | Ph-3-F | 3,4-OMe | (S) $CH_2$—O | 465 (M + H) |
| 2Q | Ph-3-$CH_2NH_2$ | 3,4-OMe | (S) $CH_2$—O | 476 (M + H) |
| 2R | Ph-2-F | 3,4-OMe | (S) $CH_2$—O | 465 (M + H) |
| 2S | Ph-3-$OCH_2$—Ph | 3,5-Me | (R,S) $CH_2$—O | 521 (M + H) |
| 2T | Ph-4-OH | 3,5-Me | (R,S) $CH_2$—O | 431 (M + H) |
| 2U | Ph-3-Cl | 3,5-Me | (S) $CH_2$—O | 449 (M + H) |
| 2V | Ph-3-CN | 3,5-Me | (S) $CH_2$—O | 440 (M + H) |
| 2W | Ph-3-$CH_2OH$ | 3,5-Me | (S) $CH_2$—O | 445 (M + H) |

EXAMPLE 3

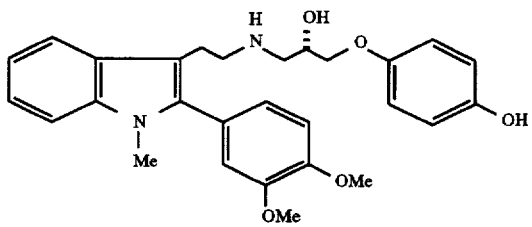

(S)-4-[3-[2-[2-(3,5-dimethylphenyl)-1-methyl-1H-indol-3-yl]ethylamino]-2-hydroxypropoxy]phenol Step 3A [2-[2-(3,4-dimethoxyphenyl)-1H-indol-3-yl]ethyl] carbamic acid benzyl ester To a suspension of 2-[2-(3,4-dimethoxyphenyl)-1H-indol-3-yl]ethylamine (150 mg in 1.5 mL methylene chloride) at −78° C. was added benzyl chloroformate (0.08 mL) and diisopropylethyl amine (0.093 mL) and the mixture warmed to 0° C. After 40 minutes, the reaction was quenched by the addition of saturated ammonium chloride, extracted with ethyl acetate and the organic portion dried over sodium sulfate. Purification by flash chromatography on silica gel (hexane:ethyl acetate, 2:1) gave the title compound (220 mg).

Step 3B 2-[2-(3,4-dimethoxyphenyl)-1-methyl-1H-indol-3-yl]ethylamine

To a solution of [2-[2-(3,4-dimethoxyphenyl)-1H-indol-3-yl]ethyl]carbamic acid benzyl ester (100 mg in 1.5 mL N,N-dimethylformamide) at 0° C. was added sodium hydride (9 mg) and the mixture allowed to stir at 0° C. After 10 minutes, iodomethane (0.016 mL) was added followed by warming to room temperature for 20 minutes and quenching by the addition of water. The mixture was extracted with ethyl acetate, washed with water and the organics dried over sodium sulfate to give the crude N-methylated product. Hydrogenolysis of the crude product by a method similar to that described in EXAMPLE 7.1 Step J gave the title compound.

Step 3C (S)-4-[3-[2-[2-(3,5-dimethylphenyl)-1-methyl-1H-indol-3-yl]ethylamino]-2-hydroxypropoxy]phenol The title compound was prepared following a procedure similar to that described in Example 2 Step F. m/e=477 (M+H)

Following a procedure similar to that described above, the following compounds were prepared:

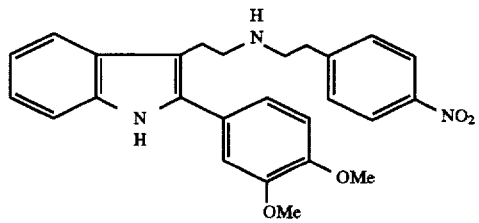

| Example # | R₁ | R₃,R₄,R₅ | R₂ | m/e |
|---|---|---|---|---|
| 3A | Ph-4-$OCH_2$—Ph | 3,4-OMe | Me | — |
| 3B | Ph-4-$OCH_2$—Ph | 3,4-OMe | H | — |
| 3C | Ph—OH | 3,4-OMe | Me | 491 (M + H) |

EXAMPLE 4.1

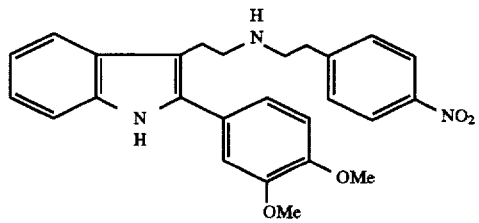

[2-[2-(3,4-dimethoxyphenyl)-1H-indol-3-yl]ethyl]-[2-(4-nitrophenyl)ethyl]amine

Step 4.1A N-[2-[2-(3,4-dimethoxyphenyl)-1H-indol-3-yl]ethyl]-2-(4-nitrophenyl)acetamide To a stirred solution of 4-nitrophenylacetic acid (100 mg in 2.5 mL N,N-dimethylformamide) was added 1-hydroxybenzotriazole (90 mg) and the mixture cooled to 0° C. After 10 minutes, 1-(3-dimethylaminopropyl)-3-ethylcarbodiimide hydrochloride (148 mg) was added. The mixture was warmed to room temperature and 3-(2-aminoethyl)-2-(3,4-dimethoxyphenyl)indole (316 mg) was added. After 17 hours the reaction was quenched by the addition of water and extracted with ethyl acetate. The organic portion was washed with water, 0.5M sodium bisulfate and brine, dried over sodium sulfate and concentrated in vacuo. Purification by flash chromatography on silica gel (hexane:ethyl acetate, 1:2) gave the title compound (116 mg).

Step 4.1B [2-[2-(3,4-dimethoxyphenyl)-1H-indol-3-yl]ethyl]-[2-(4-nitrophenyl)ethyl]amine To a stirred solution of N-[2-[2-(3,4-dimethoxy-phenyl)-1H-indol-3-yl]ethyl]-2-(4-nitrophenyl)acetamide (90 mg in 3 mL dry tetrahydrofuran) was added 0.79 mL of a 1M solution of borane in tetrahydrofuran and the mixture heated slowly to reflux on an oil bath. After 2 hours the mixture was cooled to room temperature and the excess borane quenched by the careful addition of methanol. The mixture was concentrated to half-volume, treated with N,N-dimethylethanolamine (0.60 mL) and heated to reflux on an oil bath. After 3 hours the mixture was cooled to room temperature and concentrated in vacuo. Purification by flash chromatography on silica gel (methylene chloride:methanol, 96:4) gave the title compound (79 mg).

EXAMPLE 4.2

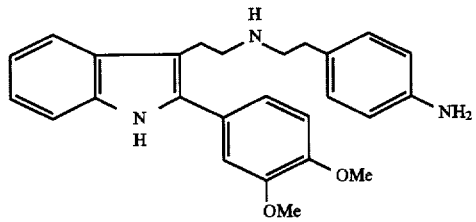

[2-[2-(3,4-dimethoxyphenyl)-1H-indol-3-yl]ethyl]-[2-(4-aminophenyl)ethyl]amine

To a stirred solution of [2-[2-(3,4-dimethoxyphenyl)-1H-indol-3-yl]ethyl]-[2-(4-nitrophenyl)ethyl]amine (45 mg in 4 mL methanol) was added 2N hydrochloric acid (0.020 mL) and 18 mg of 10% palladium hydroxide on carbon catalyst. The reaction flask was fitted with a hydrogen balloon, evacuated and recharged with hydrogen (3 times) and stirred at room temperature. After 40 minutes the reaction was flushed with nitrogen, filtered over diatomaceous earth, concentrated in vacuo and purified by flash chromatography on silica gel (methylene chloride:methanol, 96:4) to provide the title compound (32 mg). m/e=416 (M+H)

Following a procedure similar to that described in EXAMPLES 4.1 and/or 4.2, the following compounds were prepared:

| Example # | R₁ | R₃,R₄,R₅ | m/e |
|---|---|---|---|
| 4A | Ph-3-F,4-OH | 3,4-OMe | 435 (M + H) |
| 4B | Ph-4-OH | 3,4-OMe | 417 (M + H) |
| 4C | Ph-3,4-Cl | 3,4-OMe | 469 (M + H) |
| 4D | Ph-4-F | 3,4-OMe | 419 (M + H) |
| 4E | Ph-4-Cl | 3,4-OMe | 435 (M + H) |
| 4F | Ph-4-OH | 3,5-Me | 385 (M + H) |

EXAMPLE 5.1

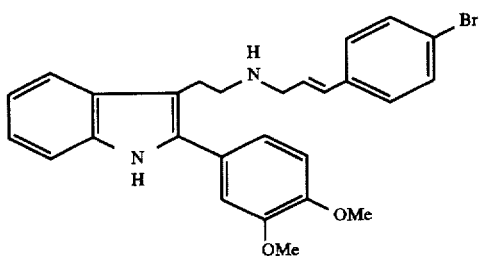

[3-(4-bromophenyl)allyl]-[2-[2-(3,4-dimethoxyphenyl)-1H-indol-3-yl]ethyl]amine

To a stirred solution of 2-[2-(3,4-dimethoxyphenyl)-1H-indol-3-yl]ethylamine (261 mg in a mixture of 3 mL N,N-dimethylformamide and 8 mL methylene chloride) at 0° C. was added a solution of 81 mg of 4-bromocinnamyl bromide in 2 mL methylene chloride and the mixture allowed to warm to room temperature. After 27 hours the reaction was quenched by the addition of water followed by extraction with ethyl acetate. The organic portion was dried over over sodium sulfate and purified by flash chromatography on silica gel (methylene chloride:methanol, 95:5) to give the title compound (93 mg). m/e=491 (M)

EXAMPLE 5.2

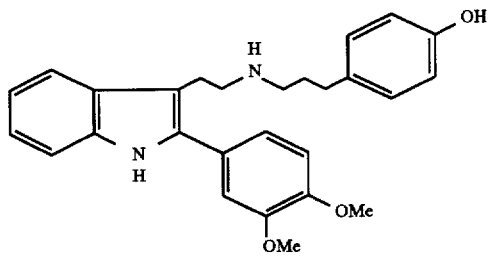

4-[3-[2-[[2-(3,4-dimethoxyphenyl)-1H-indol-3-yl]ethyl]amino]propyl)phenol

To a stirred solution of N-[2-[2-(3,4-dimethoxyphenyl)-1H-indol-3-yl]ethyl]-3-(4-hydroxyphenyl)propionamide (50 mg in 1.5 mL dry tetrahydrofuran) was added 0.45 mL of a 1M solution of borane in tetrahydrofuran and the mixture heated slowly to reflux on an oil bath. After 2 hours the mixture was cooled to room temperature and the excess borane quenched by the careful addition of methanol. The mixture was concentrated to half-volume, treated with N,N-dimethylethanolamine (0.34 mL) and heated to reflux on an oil bath. After 4 hours the mixture was cooled to room temperature and concentrated in vacuo. Purification by flash chromatography on silica gel (methylene chloride:methanol, 90:10) gave the title compound (47 mg). m/e=431 (M+H)

Following a procedure similar to that described in EXAMPLES 5.1 and 5.2, the following compounds were prepared:

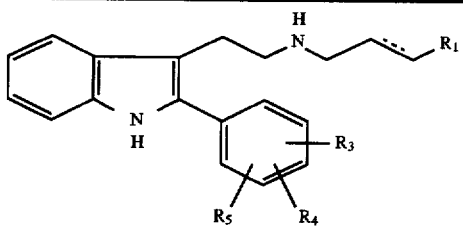

| Example # | R₁ | R₃,R₄,R₅ | m/e |
|---|---|---|---|
| 5A | Ph-3-NH₂,4-OH | 3,4-OMe | 446 (M + H) |
| 5B | Ph-4-OH | 3,5-Me | 399 (M + H) |
| 5C | Ph-4-SO₂NH₂ | 3,5-Me | 462 (M + H) |
| 5D | Ph-4-CH₂OH | 3,5-Me | 413 (M + H) |
| 5E | Ph-4-COOMe | 3,5-Me | 441 (M + H) |
| 5F | Ph-4-NHSO₂Me | 3,5-Me | 476 (M + H) |

EXAMPLE 6.1

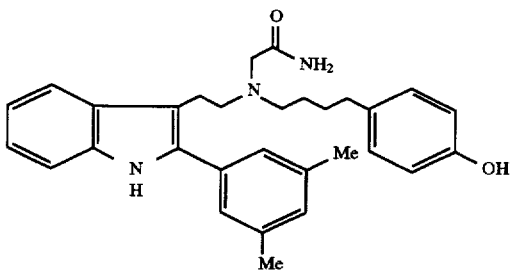

2-[[2-[2-(3,5-dimethylphenyl)-1H-indol-3-yl]ethyl]-
[4-(4-hydroxyphenyl)-butyl]amino]acetamide To a solution of 4-[4-[[2-[2-(3,5-dimethylphenyl)-1H-indol-3-yl]ethyl]amino]butyl]phenol (15 mg in a mixture of 0.7 mL acetonitrile and 0.2 mL N,N-dimethylformamide) was added 0.015 mL of diisopropylethyl amine followed by 8 mg of iodoacetamide and the mixture stirred at room temperature. After 4.5 hours the crude reaction mixture was applied to a silica gel preparative TLC plate and eluted with (methylene chloride:methanol, 93:7). Isolation of the desired band was followed by extraction with methylene chloride:methanol (95:5) and further purification of this material by flash chromatography on silica gel (hexane:ethyl acetate, 2:5) to give the title compound (16 mg). m/e=470 (M+H)

EXAMPLE 6.2

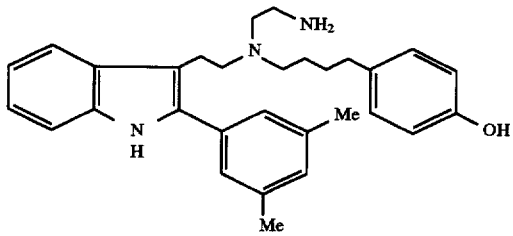

4-[4-[(2-aminoethyl)-[2-[2-(3,5-dimethylphenyl)-1H-indol-3-yl]ethyl]amino]butyl]phenol Following a procedure similar to that in Example 5.2, the title compound was prepared from 2-[[2-[2-(3,5-dimethylphenyl)-1H-indol-3-yl]ethyl]-[4-(4-hydroxyphenyl)-butyl]amino]acetamide. m/e=456 (M+H)

EXAMPLE 6.3

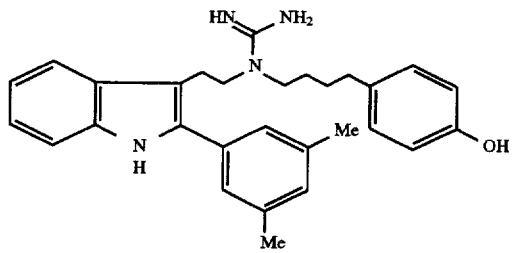

and

EXAMPLE 6.4

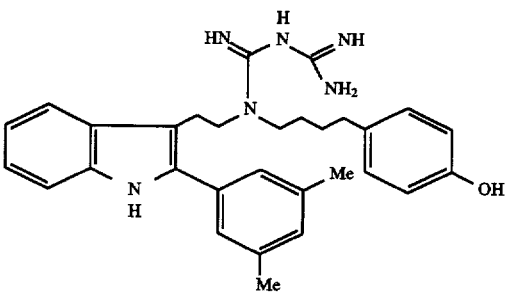

N-[2-[2-(3,5-dimethylphenyl)-1H-indol-3-yl]ethyl]-
N-[4-(4-hydroxyphenyl)butyl]guanidine and N-[2-[2-(3,5-dimethylphenyl)-1H-indol-3-yl]ethyl]-
N-[4-(4-hydroxyphenyl)butyl]guanidino-guanidine To a solution of 4-[4-[[2-[2-(3,5-dimethylphenyl)-1H-indol-3-yl]ethyl]amino]butyl]phenol (15 mg in 0.50 mL ethanol) in a thick-walled vial was added 50 mg of cyanamide followed by 0.30 mL of triethylamine. The vessel was flushed with nitrogen, sealed and heated to 70° C. on an oil bath. After 17.5 hours the mixture was cooled to room temperature, concentrated in vacuo and purified by flash chromatography on silica gel (methanol:chloroform:water:trifluoroacetic acid, 20:100:3:0.3; then repurified with methylene chloride:methanol:ammonium hydroxide, 83:17:1) to give title compounds (12 mg and 5 mg, respectively). m/e=455 (M+H), 497 (M+H)

EXAMPLE 6.5

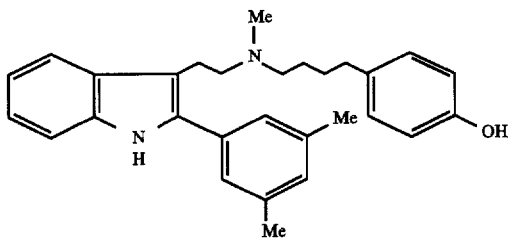

4-[4-[[2-[2-(3,5-dimethylphenyl)-1H-indol-3-yl]ethyl]methylamino]butyl]phenol

To a solution of 4-[4-[[2-[2-(3,5-dimethylphenyl)-1H-indol-3-yl]ethyl]amino]butyl]phenol (19 mg in 1 mL methanol) was added 0.020 mL of a 37% solution of formaldehyde in water followed by 0.010 mL acetic acid and 16 mg of sodium cyanoborohydride and the mixture stirred at room temperature. After 26 hours the reaction was quenched by the addition of acetic acid, concentrated in vacuo and the excess acetic acid removed by toluene azeotrope. Purification of the concentrate by flash chromatography on silica gel (methylene chloride:methanol, 93.5:6.5; then methylene chloride:methanol:ammonium hydroxide, 90:10:1) gave the title compound (20 mg). m/e=427 (M+H)

EXAMPLE 6.6

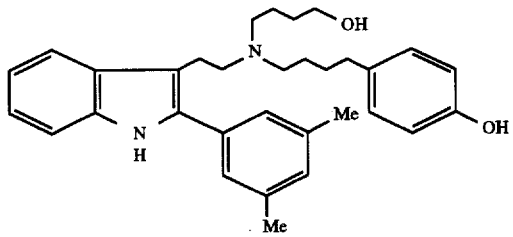

4-[4-[[2-[2-(3,5-dimethylphenyl)-1H-indol-3-yl]ethyl]-(4-hydroxybutyl)amino]butyl]phenol To a solution of 4-[4-[[2-[2-(3,5-dimethylphenyl)-1H-indol-3-yl]ethyl]amino]butyl]phenol (18 mg in 2 mL tetrahydrofuran) was added 0.050 mL of 2-ethoxytetrahydrofuran followed by 0.25 mL of 30% aqueous acetic acid and the mixture stirred for 30 minutes. At this time 0.35 mL triethylamine was added followed by 10% palladium hydroxide on carbon catalyst. The reaction flask was fitted with a hydrogen balloon, evacuated and recharged with hydrogen (3 times) and stirred at room temperature. After 23 hours the reaction was flushed with nitrogen, filtered over diatomaceous earth and concentrated in vacuo and partially purified by flash chromatography on silica gel (methylene chloride:methanol, 92:8). Repurification by HPLC (C8, methanol:water, 55:45=0.1% trifluoroacetic acid) gave the title compound (2.8 mg). m/e=485 (M+H)

Following a procedure similar to that described in EXAMPLES 6.5 or 6.6, the following compounds were prepared:

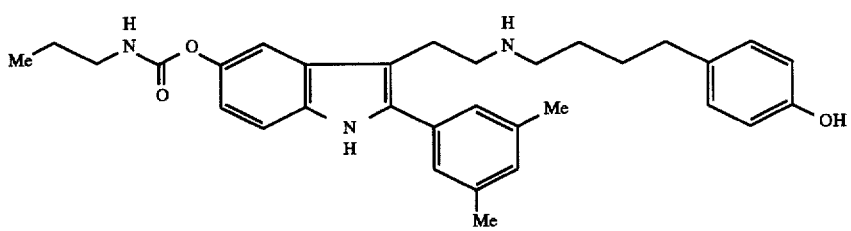

| Example # | R$_2$ | R$_3$–R$_5$ | m/e |
|---|---|---|---|
| 6A | CH$_3$ | 3,4-OMe | 459 (M + H) |
| 6B | (CH$_2$)$_4$–Ph(4-OH) | 3,5-Me | 561 (M + H) |

EXAMPLE 7.1

Propylcarbamic acid 2-(3,5-dimethylphenyl)-3-[2-[4-(4-hydroxyphenyl)butylamino]ethyl]-1H-indol-5-yl ester Step 7.1A 2-[2-(5-benzyloxy-1H-indol-3-yl)ethyl]isoindole-1,3-dione To a stirred suspension of 5-benzyloxytryptamine hydrochloride (1.0 g in 10 mL of dry tetrahydrofuran) was added triethylamine (0.50 mL) followed by N-carbethoxyphthalimide (750 mg) and the mixture heated to reflux on an oil bath. After 48 hours the reaction was cooled to room temperature, filtered and the filtrate concentrated in vacuo. The resulting solid was suspended in a mixture of hexane/methylene chloride (2.5:1, 50 mL) and filtered to give the title compound (1.3 g).

Step 7.1B 2-[2-(5-benzyloxy-2-bromo-1H-indol-3-yl)ethyl]isoindole-1,3-dione

To a solution of 2-[2-(5-benzyloxy-1H-indol-3-yl)ethyl]isoindole-1,3-dione (800 mg in a mixture of dry 25 mL tetrahydrofuran and 25 mL dry chloroform) at 0° C. was added pyridinium hydrobromide perbromide (666 mg) and the mixture stirred at 0° C. After 23 minutes the reaction was quenched by the addition of saturated sodium bicarbonate and extracted with ethyl acetate. The organic portion was washed with saturated sodium bicarbonate (3×) and 0.3M sodium bisulfate (3×) then dried over magnesium sulfate.

Purification of the concentrate by flash chromatography on silica gel (hexane:ethyl acetate, 7:2) followed by repurification by flash chromatography on silica gel (methylene chloride) gave the title compound (632 mg).

Step 7.1C 2-[2-[5-benzyloxy-2-(3,5-dimethylphenyl)-1H-indol-3-yl]ethyl]isoindole-1,3-dione To a solution of 2-[2-(5-benzyloxy-2-bromo-1H-indol-3-yl)ethyl]isoindole-1,3-dione (500 mg in a mixture of 6 mL ethanol and 16 mL toluene) was added 3,5-dimethylphenyl boronic acid (205 mg) followed by 2.7 mL of 1M sodium carbonate. To the stirred solution was added lithium chloride (156 mg) followed by tetrakis(triphenylphosphine) palladium (78 mg) and the mixture heated to reflux on an oil bath. After 2 hours the mixture was cooled to room temperature and concentrated in vacuo. Purification by flash chromatography on silica gel (hexane:methylene chloride:ethyl acetate, 15:8:1 then 12:8:1) gave the title compound (479 mg).

Step 7.1D 2-[2-[2-(3,5-dimethylphenyl)-5-hydroxy-1H-indol-3-yl]ethyl]isoindole-1,3-dione To a stirred solution of 2-[2-[5-benzyloxy-2-(3,5-dimethylphenyl)-1H-indol-3-yl]ethyl]isoindole-1,3-dione (510 mg in 20 mL dry ethyl acetate was added 197 mg of 10% palladium on carbon catalyst. The reaction flask was fitted with a hydrogen balloon, evacuated and recharged with hydrogen (3 times) and stirred at room temperature. After 37 hours the reaction was flushed with nitrogen, filtered over diatomaceous earth and concentrated in vacuo to provide the crude title compound (418 mg).

Step 7.1 E 3-(2-aminoethyl)-2-(3,5-dimethylphenyl)-1H-indol-5-ol

To a solution of 2-[2-[2-(3,5-dimethylphenyl)-5-hydroxy-1H-indol-3-yl]ethyl]isoindole-1,3-dione (418 mg in a mixture of 7 mL ethanol and 7 mL tetrahydrofuran) was added 2.5 mL of 95% aqueous hydrazine and the reaction stirred at room temperature. After 12 hours the mixture was concentrated in vacuo and purified by flash chromatography on silica gel (methylene chloride:methanol:ammonium hydroxide, 89:11:1) to provide the title compound (228 mg).

Step 7.1F 4-(4-benzyloxyphenyl)-N-{2-[2-(3,5-dimethylphenyl)-5-hydroxy-1H-indol-3-yl]ethyl}butyramide To a stirred solution of 4-benzyloxyphenylbutyric acid (159 mg in a mixture of 2 mL methylene chloride and 0.5 mL N,N-dimethylformamide) was added 1-hydroxybenzotriazole (110 mg) and 1-(3-dimethylaminopropyl)-3-ethylcarbodiimide hydrochloride (113 mg) and the reagents allowed to mix for 30 minutes. At this time a solution of 3-(2-aminoethyl)-2-(3,5-dimethylphenyl)-1H-indol-5-ol (144 mg in 4 mL N,N-dimethylformamide) was added and the reaction stirred at room temperature. After 6 hours, the mixture was concentrated in vacuo and purified by flash chromatography on silica gel (hexane:ethyl acetate, 4:5) to give the title compound (241 mg).

Step 7.1G 3-[2-[4-(4-benzyloxyphenyl)butylamino]ethyl]-2-(3,5-dimethylphenyl)-1H-indol-5-ol To a stirred solution of 4-(4-benzyloxyphenyl)-N-{2-[2-(3,5-dimethylphenyl)-5-hydroxy-1H-indol-3-yl]ethyl}butyramide(241 mg in 10 mL dry tetrahydrofuran) was added 4 mL of a 1M solution of borane in tetrahydrofuran and the mixture heated slowly to reflux on an oil bath. After 2 hours the mixture was cooled to room temperature and the excess borane quenched by the careful addition of methanol. The mixture was concentrated to half-volume, treated with N,N-dimethylethanolamine (1.4 mL) and heated to reflux on an oil bath. After 3 hours the mixture was cooled to room temperature and concentrated in vacuo. Purification by flash chromatography on silica gel (methylene chloride:methanol, 92:8) gave the title compound (234 mg).

Step 7.1H [4-(4-benzyloxyphenyl)-butyl]-[2-[2-(3,5-dimethylphenyl)-5-hydroxy-1H-indol-3-yl]ethyl]carbamic acid benzyl ester To a solution of 3-[2-[4-(4-benzyloxyphenyl)butylamino]ethyl]-2-(3,5-dimethylphenyl)-1H-indol-5-ol (234 mg in 5 mL of dry methylene chloride) at −78° C. was added benzyl chloroformate (0.082 mL) and diisopropylethylamine (0.104 mL) and the mixture stirred at room temperature. After 1 hour the reaction was quenched by the addition of saturated sodium bicarbonate and extracted with ethyl acetate. The organic portion was washed with saturated ammonium chloride, dried over magnesium sulfate and concentrated in vacuo. Purification by flash chromatography on silica gel (hexane:ethyl acetate, 3:1 then 2:1) gave the title compound (155 mg).

Step 7.1I Propylcarbamic acid 3-(2-benzyloxycarbonyl-[4-(4-benzyloxyphenyl)butyl]amino]-ethyl)-2-(3,5-dimethylphenyl)-1H-indol-5-yl ester To a stirred solution of [4-(4-benzyloxyphenyl)-butyl]-[2-[2-(3,5-dimethylphenyl)-5-hydroxy-1H-indol-3-yl]ethyl] carbamic acid benzyl ester (20 mg in 3 mL dry methylene chloride) at 0° C. was added triphosgene (4.9 mg) and pyridine (0.037 mL of a 10% solution in methylene chloride) and the reagents allowed to mix for 30 minutes. At this time, propylamine (0.040 mL) was added and the mixture allowed to warm to room temperature. After 30 minutes, the reaction was quenched by the addition of 0.3M sodium bisulfate and extracted with ethyl acetate. The organic portion was washed with 0.3M sodium bisulfate (3×) and brine, then dried over magnesium sulfate and concentrated in vacuo. Purification by flash chromatography on silica gel (hexane:methylene chloride:ethyl acetate, 4:5:1) gave the title compound (17 mg).

Step 7.1J Propylcarbamic acid 2-(3,5-dimethylphenyl)-3-[2-[4-(4-hydroxyphenyl)-butylamino]ethyl]-1H-indol-5-yl ester To a stirred solution of propylcarbamic acid 3-(2-[benzyloxycarbonyl-[4-(4-benzyloxyphenyl)butyl]amino]-ethyl)-2-(3,5-dimethylphenyl)-1H-indol-5-yl ester (17 mg in a mixture of 1.5 mL tetrahydrofuran and 0.5 mL methanol) was added 16 mg of 10% palladium on carbon catalyst followed by acetic acid (0.010 mL of a 30% solution in water). The reaction flask was fitted with a hydrogen balloon, evacuated and recharged with hydrogen (3 times) and stirred at room temperature. After 1.5 hours the reaction was flushed with nitrogen, filtered over diatomaceous earth and concentrated in vacuo. Purification by flash chromatography (methylene chloride:methanol:ammonium hydroxide, 90:6:1) gave the title compound (11 mg). m/e=514 (M+H)

PREPARATION OF SYNTHETIC INTERMEDIATES 4-(4-benzyloxyphenyl)butyric acid

Step A: 4-(4-benzyloxyphenyl)butyric acid benzyl ester

To a stirred solution of 4-hydroxyphenylbutyric acid (810 mg in 8 mL N,N-dimethylformamide) at 0° C. was added sodium hydride (290 mg of an 80% dispersion in mineral oil) and the mixture allowed to warm to room temperature. Benzyl bromide (1.2 mL) was added after 20 minutes and the mixture stirred at room temperature. After 13 hours the reaction was quenched by the addition of saturated ammonium chloride and extracted with ethyl acetate. The organic portion was washed with water (4×), dried over sodium sulfate and concentrated in vacuo. Purification by flash chromatography on silica gel (hexane:ethyl acetate, 13:1) gave the title compound (1.45 g).

Step B: 4-(4-benzyloxyphenyl)butyric acid

To a stirred solution of 4-(4-benzyloxyphenyl)butyric acid benzyl ester (277 mg in a mixture of 3 mL methanol and 1 mL methylene chloride) at 0° C. was added 1.5 mL of 5M sodium hydroxide and the mixture warmed to room temperature. After 2 hours the mixture was acidified to pH 2 by the addition of aqueous hydrochloric acid, the aqueous portion extracted with ethyl acetate (5×) and the resulting organics concentrated in vacuo. Purification by flash chromatography on silica gel (methylene chloride:methanol, 94:6 then 96:4+0.25% TFA) gave the title compound (196 mg).

3,5-dimethylphenylboronic acid

To a solution of 5-bromo-m-xylene (1.5 g in 15 mL of dry tetrahydrofuran) at −78° C. was added 6.4 mL of a 1.4M solution of butyllithium in hexane and the mixture stirred for 20 minutes. At this time triisopropyl borate (2.8 mL) was added and the mixture allowed to warm to room temperature. After 1.5 hours the reaction was concentrated in vacuo to 1/3 volume then cooled to 0° C. and treated with 2N hydrochloric acid (9 mL) followed by warming to room temperature. After 4 hours the mixture was made basic by the addition of 2.5M sodium hydroxide and partitioned between ethyl ether (75 mL) and 1.25M sodium hydroxide. The organic layer was extracted with 1.25M sodium hydroxide (2×) and the aqueous portion then cooled to 0° C. and acidified to pH 3 by the dropwise addition of conc. hydrochloric acid. The white slurry was dissolved in methylene chloride, the organic portion dried over magnesium sulfate and concentrated in vacuo to provide the title compound (960 mg).

EXAMPLE 7.2

Ethylcarbamic acid 2-(3,5-dimethylphenyl)-3-[2-[4-(4-hydroxyphenyl)butylamino]ethyl]-1H-indol-5-yl ester Step 7.2A Ethylcarbamic acid 3-(2-[benzyloxycarbonyl-[4-(4-benzyloxyphenyl)butyl]amino]-ethyl)-2-(3,5-dimethylphenyl)-1H-indol-5-yl ester To a solution of [4-(4-benzyloxyphenyl)-butyl]-[2-[2-(3,5-dimethylphenyl)-5-hydroxy-1H-indol-3-yl]ethyl] carbamic acid benzyl ester (50 mg in 0.5 mL dry tetrahydrofuran) was added 0.035 mL of ethyl isocyanate and the mixture stirred at room temperature. Over the course of 2 weeks, additional ethyl isocyanate was added in portions and the mixture heated to reflux for several days after which time it was cooled to room temperature, concentrated in vacuo and purified by flash chromatography on silica gel (hexane:ethyl acetate, 2:1) to give the title compound (20 mg).

Step 7.2B Ethylcarbamic acid 2-(3,5-dimethylphenyl)-3-[2-[4-(4-hydroxyphenyl)butylamino]ethyl]-1H-indol-5-yl ester To a stirred solution of ethylcarbamic acid 3-(2-[benzyloxycarbonyl-[4-(4-benzyloxyphenyl)butyl]amino]-ethyl)-2-(3,5-dimethylphenyl)-1H-indol-5-yl ester (12 mg in a mixture of 1.5 mL tetrahydrofuran and 0.5 mL methanol) was added 12 mg of 10% palladium hydroxide on carbon catalyst followed by acetic acid (0.010 mL of a 30% solution in water). The reaction flask was fitted with a hydrogen balloon, evacuated and recharged with hydrogen (3 times) and stirred at room temperature. After 1.5 hours the reaction was flushed with nitrogen, filtered over diatomaceous earth and concentrated in vacuo. Purification by flash chromatography (methylene chloride:methanol: ammonium hydroxide, 90:7:1) gave the title compound (8.2 mg). m/e=500 (M+H)

Following a procedure similar to that described in EXAMPLES 7.1 and 7.2 above, the following compounds were prepared:

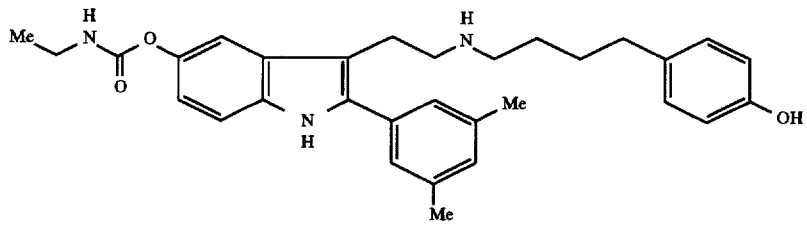

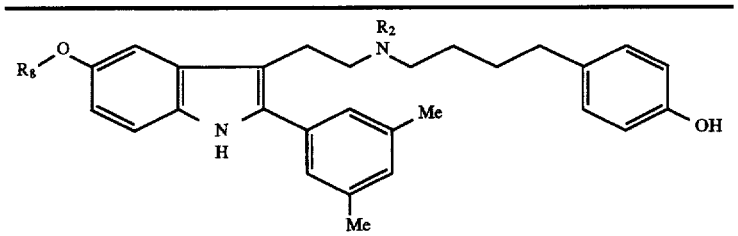

| Example | R₂ | R₈ | m/e |
|---|---|---|---|
| 7A | $(CH_2)_4OH$ | $-CO-NHEt$ | 572 (M + H) |
| 7B | $(CH_2)_4OH$ | $-CO-N(CH_2CH_3)-CO-NCH_2CH_3$ | 643 (M + H) |
| 7C | H | $-CO-N(CH_2CH_3)-CO-NHCH_2CH_3$ | 571 (M + H) |
| 7D | H | $-CO-OCH_2CH_3$ | 501 (M + H) |
| 7E | H | $-CO-NH-CH_3$ | 486 (M + H) |
| 7F | H | $-CO-N-(CH_3)_2$ | 500 (M + H) |
| 7G | H | $-CO-NH-Ph$ | 548 (M + H) |

EXAMPLE 8

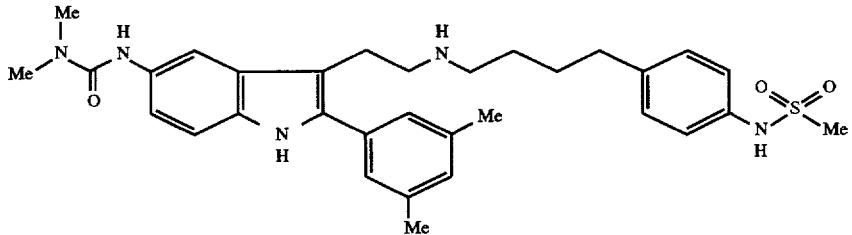

N-[4-(4-{2-[2-(3,5-dimethylphenyl)-5-(3,3-dimethylureido)-1H-indol-3-yl]ethylamino}butyl) phenyl]methanesulfonamide Step 8A 2-(3,5-dimethylphenylethynyl)-4-nitrophenylamine To a solution of 3,5-dimethylphenylethyne (156 mg in 7 mL of dry, nitrogen saturated triethylamine) was added 2-iodo-4-nitroaniline (264 mg, prepared essentially as described in: Toth, I. Helv. Chim. Acta, 1971, 54, 1486.) followed by tetrakis(triphenylphosphine)palladium (23 mg) and cuprous bromide (10 mg) and the mixture heated to reflux on an oil bath. After 2 hours the mixture was cooled to room temperature, concentrated in vacuo and purified by flash chromatography on silica gel (hexane:methylene chloride:ethyl acetate, 15:8:1) to give the title compound (256 mg).

Step 8B 2-(3,5-dimethylphenyl)-5-nitro-1H-indole

To a stirred solution of 2-(3,5-dimethylphenylethynyl)-4-nitrophenylamine (50 mg in 3 mL of dry, nitrogen saturated acetonitrile) was added 5 mg of palladium (II) chloride and the mixture heated to reflux on an oil bath. After 3 hours the mixture was cooled to room temperature, concentrated in vacuo and purified by flash chromatography on silica gel (hexane:methylene chloride:ethyl acetate 15:8:1) to provide the title compound (46 mg).

Step 8C N-benzyl-2-[2-(3,5-dimethylphenyl)-5-nitro-1H-indol-3-yl]-N-[4-(4-methanesulfonylaminophenyl)butyl]-2-oxo-acetamide To a stirred suspension of 2-(3,5-dimethylphenyl)-5-nitro-1H-indole (59 mg in 6 mL dry dichloroethane) was added oxalyl chloride (0.025 mL) and heated to reflux on an oil bath. After 15 hours the mixture was cooled to room temperature, diluted with benzene and the volatiles removed in vacuo. The resulting solid was dissolved in 3 mL dry tetrahydrofuran and cooled to 0° C. To this a solution of N-[4-(4-benzylaminobutyl)-phenyl]methanesulfonamide (74 mg in 2 mL dry methylene chloride) was added simultaneously with triethylamine (0.047 mL) and the mixture stirred for 20 minutes at 0° C. then warmed to room temperature. After 10 minutes the reaction was quenched by the addition of saturated sodium bicarbonate, extracted with ethyl acetate. The organic portion was washed with saturated ammonium chloride (2×), dried over magnesium sulfate and concentrated in vacuo. Purification by flash chromatography on silica gel (hexane:ethyl acetate, 4:5) gave the title compound (127 mg).

Step 8D N-[4-[4-(benzyl-{2-[2-(3,5-dimethylphenyl)-5-nitro-1H-indol-3-yl]ethyl}amino)butyl]phenyl]-methanesulfonamide To a stirred solution of N-benzyl-2-[2-(3,5-dimethylphenyl)-5-nitro-1H-indol-3-yl]-N-[4-(4-methanesulfonylaminophenyl)butyl]-2-oxo-acetamide (73 mg in 4 mL dry tetrahydrofuran) was added 1 mL of a 1M solution of borane in tetrahydrofuran and the mixture heated slowly to reflux on an oil bath.

After 2 hours the mixture was cooled to room temperature and the excess borane quenched by the careful addition of methanol. The mixture was concentrated to half-volume, treated with N,N-dimethylethanolamine (0.35 mL) and heated to reflux on an oil bath. After 2.5 hours the mixture was cooled to room temperature and concentrated in vacuo. Purification by flash chromatography on silica gel (hexane:ethyl acetate, 3:2) gave the title compound (59 mg).

Step 8E N-{4-[4-({2-[5-amino-2-(3,5-dimethylphenyl)-1H-indol-3-yl]ethyl}benzylamino)butyl]phenyl}methanesulfonamide To a stirred solution of N-{4-[4-(benzyl-{2-[2-(3,5-dimethylphenyl)-5-nitro-1H-indol-3-yl]ethyl}amino)butyl]

phenyl}methanesulfonamide (59 mg in 4 mL absolute ethanol) was added ca. 15 mg of Raney® nickel. The reaction flask was fitted with a hydrogen balloon, evacuated and recharged with hydrogen (3 times) and stirred at room temperature. After 3 hours the reaction was flushed with nitrogen, filtered over diatomaceous earth and concentrated in vacuo. Purification by flash chromatography on silica gel (hexane:ethyl acetate, 1:2) gave the title compound (42 mg).

Step 8F N-{4-[4-(benzyl-{2-[2-(3,5-dimethylphenyl)-5-(3,3-dimethylureido)-1H-indol-3-yl]ethyl}amino)butyl]phenyl}methanesulfonamide To a stirred solution of N-{4-[4-({2-[5-amino-2-(3,5-dimethylphenyl)-1H-indol-3-yl]ethyl}benzylamino)butyl] phenyl}methanesulfonamide (15 mg in 1.5 mL of dry methylene chloride) at 0° C. was added dimethylcarbamyl chloride (0.03 mL of a 10% v/v solution in methylene chloride) and diisopropylethylamine (0.053 mL of a 10% v/v solution in methylene chloride) and the mixture warmed to room temperature. After 3 days the reaction was concentrated in vacuo and purified by flash chromatography on silica gel (methylene chloride:methanol:ammonium hydroxide, 96:4:1) to give the title compound (17 mg).

Step 8G N-[4-(4-{2-[2-(3,5-dimethylphenyl)-5-(3,3-dimethylureido)-1H-indol-3-yl]ethylamino}butyl)phenyl] methanesulfonamide To a stirred solution of N-{4-[4-(benzyl-{2-[2-(3,5-dimethylphenyl)-5-(3,3-dimethylureido)-1H-indol-3-yl] ethyl}amino)butyl]phenyl}methanesulfonamide (17 mg in a mixture of 4 mL tetrahydrofuran and 1.5 mL methanol) was added 7 mg of 10% palladium hydroxide on carbon catalyst followed by acetic acid (0.020 mL of a 30% solution in water). The reaction flask was fitted with a hydrogen balloon, evacuated and recharged with hydrogen (3 times) and stirred at room temperature. After 45 minutes the reaction was flushed with nitrogen, filtered over diatomaceous earth and concentrated in vacuo. Purification by flash chromatography (methylene chloride:methanol:ammonium hydroxide, 91:9:1) gave the title compound (14.5 mg). m/e=576 (M+H)

Following a procedure similar to that described above, the following compounds were prepared:

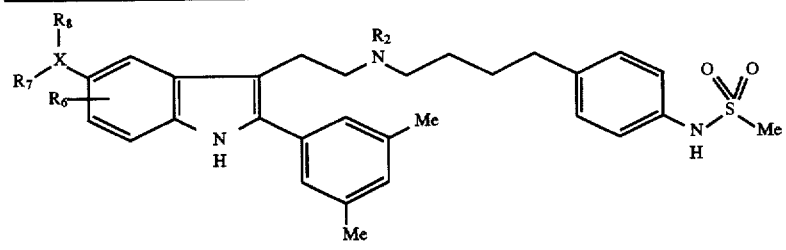

| Example | $R_6$ | $R_2$ | $X-R_7R_8$ | m/e |
|---|---|---|---|---|
| 8A | H | H | NH—COOCH$_2$Ph | |
| 8B | H | CH$_2$Ph | NH—COO—Et | 677 (M + H) |
| 8C | H | H | NH—COO—Et | 577 (M + H) |
| 8D | H | H | NH—CO—N(CH$_2$CH$_3$)$_2$ | 604 (M + H) |
| 8E | H | H | N(CH$_2$CH$_3$)CO—N(CH$_2$CH$_3$)$_2$ | 632 (M + H) |
| 8F | H | H | NH—CO-Cyclopropyl | 573 (M + H) |
| 8G | H | H | NH—CO—Ph | 609 (M + H) |
| 8H | H | H | 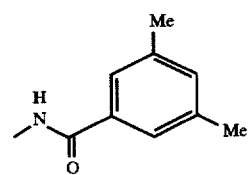 | 637 (M + H) |
| 8I | H | H | 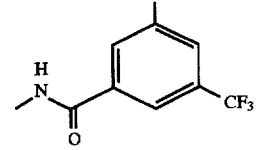 | 745 (M + H) |
| 8J | H | H | NH—CO—Me | 547 (M + H) |
| 8K | H | H | 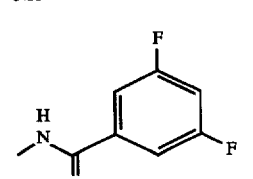 | 645 (M + H) |
| 8L | H | H | NH—CO—CH(Me)—NH—CO—Me | 618 (M + H) |
| 8M | H | H | N(Me)—CO—Ph | 623 (M + H) |
| 8N | H | H | N(Me)—CO—Me | 561 (M + H) |

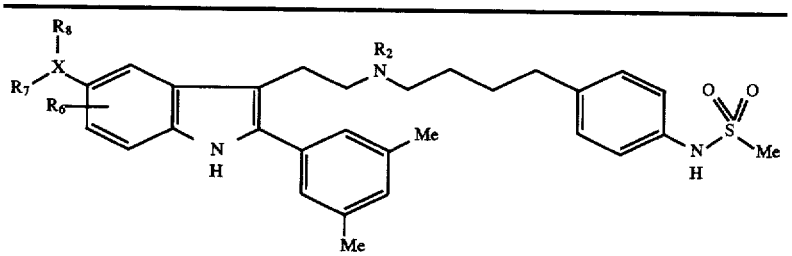

| Example | R$_6$ | R$_2$ | X—R$_7$R$_8$ | m/e |
|---|---|---|---|---|
| 8O | H | H | NH—SO$_2$Me | 583 (M + H) |
| 8P | H | H | (4-methoxybenzamide NHMe) | 639 (M + H) |
| 8Q | H | H | (3-methoxybenzamide NHMe) | 639 (M + H) |
| 8R | H | H | NH—CO—NH(CH$_2$CH$_3$) | 576 (M + H) |
| 8S | H | H | NH—CO—CH$_2$CH$_3$ | 561 (M + H) |
| 8T | H | H | NH—CO—NHMe | 562 (M + H) |
| 8U | H | H | NH—CO—NH(CH$_2$CH$_2$CH$_3$) | 590 (M + H) |
| 8V | H | H | NH—CO—CH(CH$_3$)$_2$ | 575 (M + H) |
| 8W | H | H | NH—CO—NH—CH(CH$_3$)$_2$ | 590 (M + H) |
| 8X | H | H | NH—CO—NH-(cyclopropyl) | 588 (M + H) |
| 8Y | H | H | NH—SO$_2$—(CH$_2$CH$_2$CH$_3$) | 611 (M + H) |
| 8Z | H | H | NH—SO$_2$—NH—(CH$_2$CH$_3$) | 612 (M + H) |
| 8AA | H | H | SCH$_3$ | 536 (M + H) |
| 8BB | H | H | S(O)CH$_3$ | 552 (M + H) |
| 8CC | H | H | S(O)$_2$CH$_3$ | 568 (M + H) |
| 8DD | H | H | S(O)$_2$NH$_2$ | 569 (M + H) |
| 8EE | 6-Cl | H | * | 569 (M + H) |
| 8FF | 6-Cl | H | NH—CO—NH-(cyclopropyl) | 622 (M + H) |

* = NO$_2$

EXAMPLE 9

Following a procedure similar to that described in EXAMPLES 4.1 and 12.1 the following compounds were prepared:

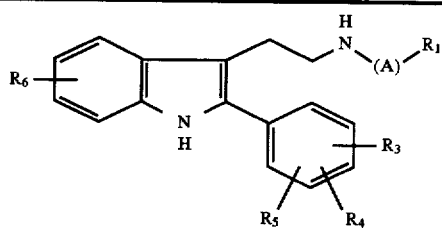

| EX. # | R$_1$ | R$_3$—R$_5$ | R$_6$ | (CH$_2$)$_n$ = (A) | m/e |
|---|---|---|---|---|---|
| 9A | Ph-4-O—CH$_2$—Ph | 3,4-OMe | | 4 | — |
| 9B | Ph-4-OH | 3,4-OMe | | 4 | 445 (M + H) |
| 9C | Ph-4-OH | 3,4-OMe | | 1 | 403 (M + H) |
| 9D | Ph-4-NO$_2$ | 3,4-OMe | | 4 | 474 (M + H) |
| 9E | Ph-4-NH$_2$ | 3,4-OMe | | 4 | 444 (M + H) |
| 9F | Ph-4-OCH$_3$ | 3-OCH$_2$(Ph-3-OMe) | | 4 | 535 (M + H) |
| 9G | Ph-4-OH | 3,4-OMe | | 5 | 549 (M + H) |
| 9H | Ph-4-OH | 3,5-CF3 | | 4 | 521 (M + H) |
| 9I | Ph-4-OH | 3,4-OMe | | 6 | 473 (M + H) |

-continued

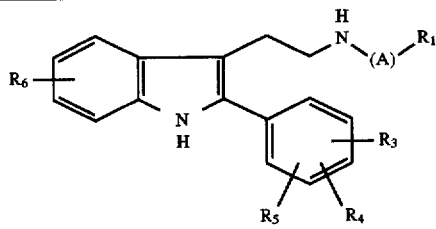

| EX. # | R₁ | R₃—R₅ | R₆ | (CH₂)ₙ = (A) | m/e |
|---|---|---|---|---|---|
| 9J | Ph-4-OCH₃ | 3,4-OMe | | 4 | 459 (M + H) |
| 9K | Ph-4-OH | 2-Me | | 4 | 399 (M + H) |
| 9L | Ph-4-OH | 2,4-Cl | | 4 | 453 (M) |
| 9M | Ph-4-OH | 4-F | | 4 | 403 (M + H) |
| 9N | Ph-4-OH | 4-Me | | 4 | 399 (M + H) |
| 9O | Ph-4-OH | 3-Cl,4-F | | 4 | 437 (M + H) |
| 9P | Ph-4-OH | 3,5-Cl | | 4 | 453 (M) |
| 9Q | Ph-4-OH | — | | 4 | 385 (M + H) |
| 9R | Ph-4-OH | 3,5-Me | | 4 | 413 (M + H) |
| 9S | Ph-4-OH | 3-Me | | 4 | 399 (M + H) |
| 9T | Ph-4-OH | 2,6-Me | | 4 | 413 (M + H) |
| 9U | Ph-4-OH | 3-OMe | | 4 | 415 (M + H) |
| 9V | Ph-4-OH | 3,5-OMe | | 4 | 445 (M + H) |
| 9W | Ph-4-OCH₃ | 3,5-Me | | 4 | 427 (M + H) |
| 9X | Ph-4-OH | 3,5-Me | 5-Cl | 4 | 447 (M + H) |
| 9Y | Ph-4-OH | 3,5-Me | 5-Me | 4 | 427 (M + H) |
| 9Z | Ph-4-OH | 3,5-Me | | 5 | 427 (M + H) |
| 9AA | Ph-4-OH | 3,5-Me | 5-OBn | 4 | 519 (M + H) |
| 9BB | Ph-4-OH | 2,3-Me | | 4 | 413 (M + H) |
| 9CC | Ph-4-OH | 3-N(Me)₂ | | 4 | 428 (M + H) |
| 9DD | Ph-4-OH | 3,5-Me | | 6 | 441 (M + H) |
| 9EE | Ph-4-OH | 2,5-Me | | 4 | 413 (M + H) |
| 9FF | Ph-4-OH | 3,5-Me | 7-Me | 4 | 427 (M + H) |
| 9GG | Ph-4-OH | 3,5-Me | | 1 | 371 (M + H) |
| 9HH | Ph-4-OH | 3,5-Me | 5-OMe | 4 | 443 (M + H) |
| 9II | Ph-4-OH | 3-OCH₂—Ph | | 4 | 491 (M + H) |
| 9JJ | Ph-4-OH | 3-CH(Me)OBn | | 4 | 519 (M + H) |
| 9KK | Ph-4-OH | 3-Et | | 4 | 413 (M + H) |
| 9LL | Ph-4-NO₂ | 3,5-Me | | 4 | 442 (M + H) |
| 9MM | Ph-4-OH | 3-CH(Me)OH | | 4 | 429 (M + H) |
| 9NN | Ph-4-OH | 3,5-Me | 6-NH—C(O)CH₃ | 4 | |
| 9OO | Ph-4-OCH₃ | 3-O—CH₂Ph | | 4 | 505 (M + H) |
| 9PP | Ph-4-NH₂ | 3,5-Me | | 4 | 412 (M + H) |
| 9QQ | Ph-4-NH—COCH₃ | 3,5-Me | | 4 | 454 (M + H) |
| 9RR | Ph-4-NHSO₂Ph | 3,5-Me | | 4 | 552 (M + H) |
| 9SS | Ph-4-NHSO₂Me | 3,5-Me | | 4 | 490 (M + H) |
| 9TT | Ph-4-OMe | 3-OCH₂(Ph-3-OMe) | | 4 | 535 (M + H) |
| 9UU | Ph-4-OH | 3-SMe | | 4 | 431 (M + H) |
| 9VV | Ph-4-OH | 3-SMe, 5-Me | | 4 | 445 (M + H) |
| 9WW | Ph-4-OH | 3,5-Me | 6-Cl | 4 | 475 (M) |
| 9XX | Ph-4-SO₂NH₂ | 3,5-Me | | 1 | — |
| 9YY | Ph-4-OH | 3,5-Me | 4-Cl | 4 | 475 (M) |
| 9ZZ | Ph-4-OH | 3-S(O)Me | | 4 | 447 (M + H) |
| 9AAA | Ph-4-OH | 3-S(O)Me, 5-Me | | 4 | 461 (M + H) |
| 9BBB | Ph-4-OH | 3-SO₂Me | | 4 | 463 (M + H) |
| 9CCC | Ph-4-OH | 3-SO₂Me, 5-Me | | 4 | 477 (M + H) |
| 9DDD | Ph-NHSO₂CF₃ | 3,5-Me | | 4 | 544 (M + H) |
| 9EEE | Ph-NHSO₂Et | 3,5-Me | | 4 | 504 (M + H) |
| 9FFF | 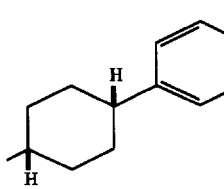 | 3,4-OMe | | 0 | 471 (M + H) |

-continued

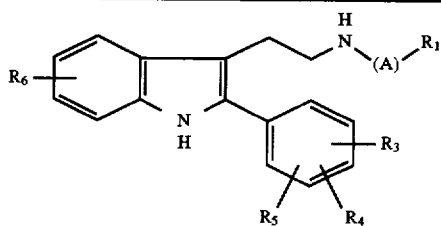

| EX. # | R₁ | R₃–R₅ | R₆ | (CH₂)ₙ = (A) | m/e |
|---|---|---|---|---|---|
| 9GGG | (4-hydroxyphenyl-trans-4-methylcyclohexyl) | 3,4-OMe | | 0 | 471 (M + H) |
| 9HHH | Ph-4-OH | 3,5-Me | 6-(3,5-dimethylphenyl) | 4 | 517 (M + H) |
| 9III | Ph-4-OH | 3-Me, 5-i-Bu | | 4 | |
| 9JJJ | Ph-4-OH | 3-Me, 5-Pr | | 4 | |
| 9KKK | Ph-4-NH₂ | 3,5-Me | 5-NHC(O)—NHEt | 4 | |
| 9LLL | Ph-4-NHSO₂-iPr | 3,5-Me | | 4 | 532 (M + H) |
| 9MMM | Ph-4-OH | 3,5-Me | 5-NO₂ | 4 | — |
| 9NNN | Ph-3,4-OMe | 3,5-Me | | 4 | 457 (M + H) |
| 9OOO | Ph-3,4-OH | 3,5-Me | | 4 | 429 (M + H) |
| 9PPP | Ph-4-OH | 3,5-Me | 5-Br | 4 | 492 (M + H) |
| 9QQQ | 2-naphthyl | 3,5-Me | | 4 | 447 (M + H) |
| 9RRR | Ph-4-NHSO₂NHMe | 3,5-Me | | 4 | 505 (M + H) |
| 9SSS | Ph-4-CN | 3,5-Me | | 4 | 422 (M + H) |
| 9TTT | Ph-4-F | 3,5-Me | | 4 | 415 (M + H) |
| 9UUU | Ph-4-OH | 3,5-Me | 5-Ph | 4 | 489 (M + H) |
| 9VVV | Ph-3-Br, 4-NHSO₂—Me | 3,5-Me | | 4 | 570 (M + H) |
| 9WWW | Ph-4-NHCONHMe | 3,5-Me | | 4 | 469 (M + H) |
| 9XXX | Ph-4-OH | 3,5-Me | 5-CH(Me)₂ | 4 | 455 (M + H) |
| 9YYY | Ph-4-SO₂NH₂ | 3,5-Me | | 4 | 476 (M + H) |
| 9ZZZ | 1-naphthyl-4-OMe | 3,5-Me | | 4 | 477 (M + H) |
| 9AAAA | 1-naphthyl-4-OH | 3,5-Me | | 4 | 463 (M + H) |
| 9BBBB | Ph-3-F, 4-OMe | 3,5-Me | | 4 | 445 (M + H) |
| 9CCCC | Ph-3-F, 4-OH | 3,5-Me | | 4 | 4310 (M + H) |
| 9DDDD | Ph-4-NHSO₂NHEt | 3,5-Me | | 4 | 519 (M + H) |
| 9EEEE | Ph-4-NHCONHEt | 3,5-Me | | 4 | 483 (M + H) |
| 9FFFF | Ph-4-NHSO₂Me | 3,5-Me | 5-SO₂Me | 5 | 582 (M + H) |
| 9GGGG | Ph-4-NHSO₂Me | 3,5-Cl | 5-N(Et)CO—N(Et)₂ | 4 | — |
| 9HHHH | Ph-4-OH | 3,5-Me | 5-F | 4 | 431 (M + H) |

EXAMPLE 10

Following a procedure similar to that described in EXAMPLE 9, the following compounds were prepared:

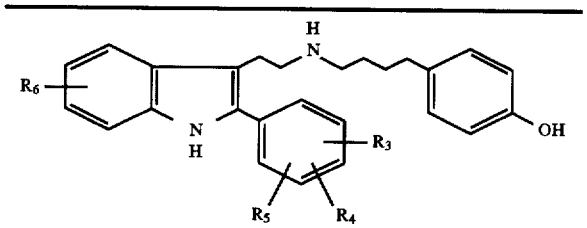

| Example # | R₃–R₅ | R₆ | m/e |
|---|---|---|---|
| 10A | 2-(CH)₄-3 | H | 435 (M + H) |
| 10B | 3-(CH)₄-4 | H | 435 (M + H) |
| 10C | 3-(CH=CH—N(Me))-4 | H | 438 (M + H) |
| 10D | 2-(CH)₄-3 | 5-OBn | 541 (M + H) |
| 10E | 2-(CH)₄-3 | 5-OH | 451 (M + H) |

-continued

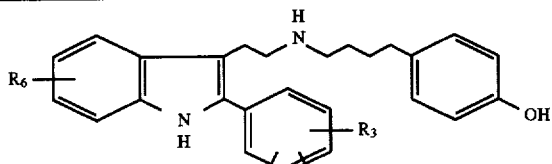

| Example # | R$_3$—R$_5$ | R$_6$ | m/e |
|---|---|---|---|
| 10F | 2-(CH)$_4$-3 | 6-F | 453 (M + H) |
| 10G | 2-(CH)$_4$-3, 5-Me | H | 449 (M + H) |

EXAMPLE 11

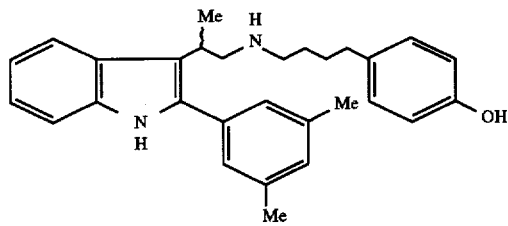

4-(4-[2-[2-(3,5-dimethylphenyl)-1H-indol-3-yl]propylamino]butyl)phenol

Step 11A 2-methylcyclopropanecarboxylic acid N-methoxy-N-methyl-amide

To a solution of 2-methylcyclopropanecarboxylic acid (10 g in a mixture of 200 mL benzene and 2 mL N,N-dimethylformamide) at 0° C. was added 10.5 mL of oxalyl chloride and the mixture stirred at 0° C. for 30 minutes then warmed to room temperature for 30 minutes. At this time, 14.6 g of N,O-dimethylhydroxylamine hydrochloride was added followed by 41 mL of triethylamine. The mixture was stirred at room temperature for one hour then quenched by the addition of saturated sodium bicarbonate. The aqueous portion was extracted with ethyl acetate and the combined organics washed with brine, dried over sodium sulfate and concentrated in vacuo. The product was purified by distillation under reduced pressure to give 8.9 g as an oil.

Step 11B (3,5-dimethylphenyl)-(2-methylcyclopropyl)methanone

To a solution of 5-bromo-meta-xylene (5.7 mL in 120 mL of dry tetrahydrofuran) at −78° C. was added 30.6 mL of a 1.4M solution of n-butyllithium in hexane and the mixture stirred at low temperature. After 15 minutes, a solution of 2-methylcyclopropanecarboxylic acid N-methoxy-N-methyl-amide (5.0 g in 50 mL tetrahydrofuran) was added dropwise over 5 minutes and the mixture then allowed to warm slowly to room temperature. After 1 hour, the reaction was quenched by the addition of 20 mL 2N hydrochloric acid and 40 mL water. This was extracted with ethyl acetate washed with saturated sodium bicarbonate and brine then dried over sodium sulfate to give 6.95 g of the crude title compound.

Step 11C 2-[2-(3,5-dimethylphenyl)-1H-indol-3-yl]propylamine

To a solution of phenylhydrazine hydrochloride (1.42 g in 24 mL n-butanol) at 95° C. was added a solution of (3,5-dimethylphenyl)-(2-methylcyclopropyl)methanone 2.0 g in 16 mL of n-butanol) and heat at 110° C. for 4 hours. At this time the reaction was cooled to room temperature, 25 mL of 1N sodium hydroxide and the mixture extracted 3× with methylene chloride. The organics were washed with brine and dried over sodium sulfate. Purification of the concentrate by flash chromatography on silica gel (methylene chloride:methanol, 95:5) gave the title compound (307 mg).

Steps 11D, 11E 4-(4-[2-[2-(3,5-dimethylphenyl)-1H-indol-3-yl]propylamino]butyl)phenol The title compound was prepared essentially as described in EXAMPLES 1 and 5.2 from 2-[2-(3,5-dimethylphenyl)-1H-indol-3-yl]propylamine.

Following a procedure similar to that described above, the following compounds were prepared:

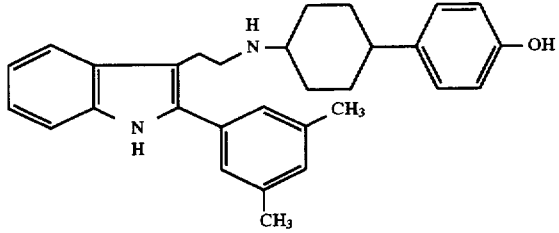

| Ex | R$_1$ | R$_2$ | R$_9$ | R$_{9a}$ | R$_{10}$ | R$_{10a}$ | A |
|---|---|---|---|---|---|---|---|
| 11A | Ph-4-OH | H | H | H | CH$_3$ | H | 4 |
| 11B | Ph-4-OH | H | Ph | H | H | H | 4 |
| 11C | Ph-4-OH | —CH$_2$CH$_2$— | | H | H | H | 4 |
| 11D | Ph-4-OH | H | CH$_3$ | H | H | H | 2 |
| 11E | Ph-4-NHSO$_2$Me | H | CH$_3$ | H | H | H | 4 |
| 11F | Ph-4-OH | H | H | H | CH$_3$ | H | 2 |
| 11G | Ph-4-OH | H | H | H | CH$_3$ | CH$_3$ | 4 |
| 11H | Ph-4-NHSO$_2$Me | H | CH$_3$ | H | H | H | 2 |

EXAMPLE 12.1

4-(4-{2-[2-(3,5-dimethylphenyl)-1H-indol-3-yl]ethylamino}cyclohexyl)phenol

A mixture of 2-[2-(3,5-dimethylphenyl)-1H-indol-3-yl]ethylamine (EXAMPLE 2, Step D, 345 mg) and 4-(4-hydroxyphenyl)cyclohexanone (62 mg) were solvated in 8 mL dry methanol to which ca. 2 g powdered 3 Å molecular sieves were added. The pH of this mixture was adjusted to 6 by the addition of 0.65 mL of a 10% solution of trifluoroacetic acid in methanol and then 90 mg sodium cyanoborohydride was added and the mixture stirred at room temperature. After 20 hours, the mixture was filtered through diatomaceous earth, concentrated in vacuo and purified by flash chromatography on silica gel [(methylene chloride:methanol:, 92:8) then again (chloroform:methanol, 90:10) to separate the diastereomers] to give the title compound (isomer A 40 mg, isomer B 36 mg). m/e=439 (M+H)

EXAMPLE 12.2

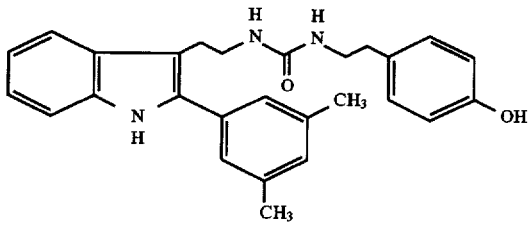

1-{2-[2-(3,5-dimethylphenyl)-1H-indol-3-yl]ethyl}-3-[2-(4-hydroxyphenyl)ethyl]urea Step 12.2A 1-[2-(4-benzyloxyphenyl)ethyl]-3-{2-[2-(3,5-dimethylphenyl)-1H-indol-3-yl]ethyl}urea To a solution of 2-[2-(3,5-dimethylphenyl)-1H-indol-3-yl]ethylamine (EXAMPLE 2 Step D, 39 mg in 1 mL dry methanol) was added 64 mg [2-(4-benzyloxyphenyl)-ethyl]-carbamic acid 4-nitrophenyl ester and the mixture stirred at room temperature. After 24 hours, the mixture was concentrated in vacuo and the residue re-solvated in ethyl acetate. This was washed with saturated aqueous potassium carbonate (3×) and brine, dried over sodium sulfate and purified by flash chromatography on silica gel (hexane:ethyl acetate, 5:4; then 1:1) to give the title compound (73 mg).

Step 12.2B 1-{2-[2-(3,5-dimethylphenyl)-1H-indol-3-yl]ethyl}-3-[2-(4-hydroxyphenyl)ethyl]urea The title compound was prepared essentially as described in EXAMPLE 2 Step B starting from 1-[2-(4-benzyloxyphenyl)ethyl]-3-{2-[2-(3,5-dimethylphenyl)-1H-indol-3-yl]ethyl}urea to give the title compound. m/e=428 (M+H)

Following a procedure similar to those described above and in EXAMPLE 4.1, the following compounds were prepared:

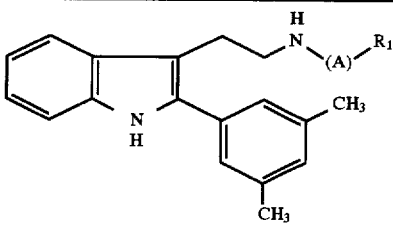

| Example | R₁ | (A) | m/e |
|---|---|---|---|
| 12A | Ph-4-O-tBu | —CH₂—CH₂—O—CH₂— | |
| 12B | Ph-4-OH | —(CH₂)₃—C(CH₃)₂—Ph-4-OH | |
| 12C | Ph-4-OH | —CH₂—CH₂—CHMe—CH₂— | |
| 12D | Ph-4-OH | —CH₂—CH(CH₃)₂— | 427 (M + H) |
| 12E | Ph-4-OH | —CNH—NH—(CH₂)₂— | |
| 12F | Ph-4-OH | —(CH₂)₃—CH(O—CH₂—CH₂—OH)— | |
| 12G | Ph-4-OH | —(CH₂)₃—C(O—CH₂—CH₂—O)— | |
| 12H | 1-(naphthyl-4-OH) | —CH₂—C(Me)₂— | 463 (M + H) |

EXAMPLE 13.1

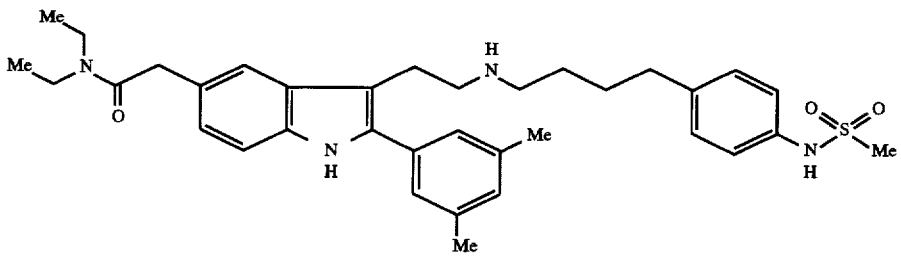

2-(2-(3,5-dimethylphenyl)-3-{2-[4-(4-methanesulfonylaminophenyl)-butylamino]-ethyl}-1H-indol-5-yl)-N,N-diethylacetamide Step 13.1A [3-(2-aminoethyl)-2-(3,5-dimethylphenyl)-1H-indol-5-yl]-acetic acid ethyl ester A mixture of 6.34 g (approximately 29.5 mmol) of ethyl 2-(4-hydrazinophenyl)acetate hydrochloride/2-(4-hydrazinophenyl)acetic acid hydrochloride, 6.22 g (29.5 mmol) of 3-chloropropyl 3,5-dimethylphenyl ketone, and 120 mL of absolute ethanol was stirred at reflux under nitrogen for 12 hours. The cooled solution was concentrated in vacuo, and the residue was partitioned between 200 mL of ethyl acetate and 50 mL of saturated aqueous sodium carbonate solution. The organic phase was washed with 25 mL of brine, then dried over sodium sulfate, and filtered. The residue from concentration of the filtrate in vacuo was purified by flash chromatography on silica gel (elution with 95:5 CH₂Cl₂—MeOH and then 95:5:0.5 CH₂Cl₂—MeOH-concentrated NH₄OH). Concentration of the product fractions gave 1.13 g (11%) of a stiff foam; nearly homogeneous by TLC in 95:5:0.5 CH₂Cl₂-MeOH-concentrated NH₄OH. 400 MHz ¹H NMR (CDCl₃) was consistent with the assigned structure. Mass spectrum (PB-NH₃/CI): m/e=351 (M+H).

Step 13.1B (2-(3,5-dimethylphenyl)-3-{2-[4-(4-methanesulfonylaminophenyl)butylamino]ethyl}-1H-indol-5-yl)acetic acid ethyl ester The reductive amination reaction of [3-(2-aminoethyl)-2-(3,5-dimethylphenyl)-1H-indol-5-yl]-acetic acid ethyl ester and 4-[4-(methanesulfonamido)phenyl]butyraldehyde was accomplished according to the procedure of Example 14.1, Step 14.1B to give the titled compound in 29% yield as a stiff foam; homogenous by TLC in 92.5:7.5 $CH_2Cl_2$—MeOH. 500 MHz $^1$H NMR ($CDCl_3$) was consistent with the assigned structure. Mass spectrum (ESI): m/e=576 (M+H).

Step 13.1C [3-(2-{benzyloxycarbonyl-[4-(4-methanesulfonylaminophenyl)butyl]amino}-ethyl)-2-(3,5-dimethylphenyl)-1H-indol-5-yl]-acetic acid ethyl ester The reaction of (2-(3,5-dimethylphenyl)-3-{2-[4-(4-methanesulfonylaminophenyl)butylamino]ethyl}-1H-indol-5-yl)acetic acid ethyl ester with benzyl chloroformate was carried out according to the procedure of Example 14.1, Step 14.1C, to give the titled compound in 73% yield as a stiff foam; homogeneous by TLC in 95:5 $CH_2Cl_2$—MeOH. 500 MHz $^1$H NMR was complex, owing to the existence of rotamers, but was consistent with the assigned structure. Mass spectrum (ESI): m/e=710 (M+H).

Step 13.1D [3-(2-{benzyloxycarbonyl-[4-(4-methanesulfonylaminophenyl)butyl]amino}ethyl)-2-(3,5-dimethylphenyl)-1H-indol-5-yl]acetic acid To a solution of 227 mg (0.32 mmol) of [3-(2-{benzyloxycarbonyl-[4-(4-methanesulfonylamino-phenyl)butyl]amino }-ethyl)-2-(3,5-dimethylphenyl)-1H-indol-5-yl]-acetic acid ethyl ester in 4.0 mL (2.0 mmol) of 0.50N potassium hydroxide in methanol was stirred under nitrogen at 60°–65° C. as 1.0 mL of water was added gradually, resulting in slight cloudiness. After 3 hours, the homogeneous solution was cooled and concentrated to small volume in vacuo. The residue was partitioned between 10 mL of ethyl acetate and 10 mL of 0.5N hydrochloric acid. The organic phase was dried (magnesium sulfate), filtered, and concentrated in vacuo at room temperature. Trituration of the residue with diethyl ether resulted in solidification of the product. This material was collected on a filter and washed with small volumes of ether. The evaporation residue from the mother liquor was also triturated with some ether to give a solid. After decantation of the ether, the trituration-decantation cycle was repeated twice more. The solids were combined and dried in vacuo to give 205 mg (94%) of a powder, mp 123°–125° C.; virtually homogeneous by TLC (92.5:7.5 $CH_2Cl_2$—MeOH). 500 MHz $^1$H NMR (DMSO-$d_6$) was complex, owing to rotamers, but was consistent with the assigned structure. Mass spectrum (ESI): m/e=682 (M+H).

Step 13.1E {2-[5-diethylcarbamoylmethyl-2-(3,5-dimethylphenyl)-1H-indol-3-yl]ethyl}-[4-(4-methanesulfonylaminophenyl)butyl]-carbamic acid benzyl ester The reaction of 34.1 mg (0.05 mmol) of [3-(2-benzyloxycarbonyl-[4-(4-methanesulfonylaminophenyl) butyl]-amino}ethyl)-2-(3,5-dimethylphenyl)-1H-indol-5-yl] acetic acid with diethylamine in the presence of PyBOP reagent was accomplished according to the procedure of Example 14.1, Step 14.1E. The crude product was purified by preparative TLC on 2 1000-micron silica gel GF plates (20×20 cm), which were developed in 92.5:7.5 $CH_2Cl_2$—MeOH. The product bands were isolated and extracted with the same solvent to afford 30.9 mg (84%) of nearly colorless residual glass; virtually homogeneous by TLC in 92.5:7.5 $CH_2Cl_2$—MeOH. 500 MHz $^1$H NMR ($CDCl_3$) was complex, owing to rotamers, but was consistent with the assigned structure. Mass spectrum (ESI): m/e=737 (M+H).

Step 13.1F 2-(2-(3,5-dimethylphenyl)-3-{2-[4-(4-methanesulfonylaminophenyl)-butylamino]-ethyl}-1H-indol-5-yl)-N,N-diethylacetamide A mixture of 28.7 mg (0.039 mmol) of {2-[5-diethylcarbamoylmethyl-2-(3,5-dimethylphenyl)-1H-indol-3-yl]ethyl}-[4-(4-methanesulfonylaminophenyl)butyl]-carbamic acid benzyl ester, 20 mg of 20% palladium hydroxide on carbon, and 5 mL of glacial acetic acid was shaken with hydrogen (50 psig) in a pressure vessel. After 1 day, an additional 20 mg of catalyst was added, and shaking with hydrogen was continued for 3 hours more. The catalyst was removed by filtration through Celite under nitrogen, and the filtrate was concentrated in vacuo. The residue was reconcentrated twice from toluene and then purified by preparative TLC on 2 1000-micron silica gel GF plates (20×20 cm), which were developed in 92.5:7.5:0.75 $CH_2Cl_2$—MeOH-concentrated $NH_4OH$. The product band from each plate was isolated, combined, and extracted with the same solvent. Concentration of the extracts in vacuo afforded 15.7 mg (67%) of a glass; virtually homogeneous by TLC in 92.5:7.5:0.75 $CH_2Cl_2$—MeOH-concentrated $NH_4OH$. 500 MHz $^1$H NMR ($CDCl_3$) was consistent with the assigned structure. Mass spectrum (ESI): m/e=603 (M+H).

EXAMPLE 13.2

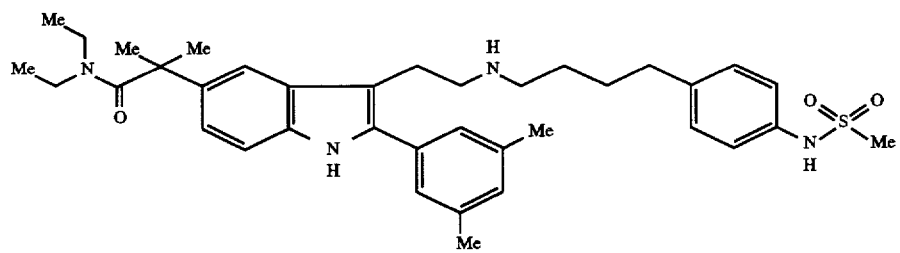

2-(2-(3,5-dimethylphenyl)-3-{2-[4-(4-methanesulfonylaminophenyl)-butylamino]ethyl}-1H-indol-5-yl)-N,N-diethylisobutyramide Step 13.2A 2-[3-(2-aminoethyl)-2-(3,5-dimethylphenyl)-1H-indol-5-yl]-2-methylpropionic acid ethyl ester By the procedure of Example 14.1 Step A, ethyl 2-(4-hydrazinophenyl)-2-methylpropionate was reacted with 3-chloropropyl 3,5-dimethylphenyl ketone to afford the titled compound in 16% yield as a stiff foam; virtually homogeneous by TLC in 95:5:0.5 $CH_2Cl_2$—MeOH-concentrated $NH_4OH$. 500 MHz 1H NMR ($CDCl_3$) was consistent with the assigned structure. Mass spectrum (PB-$NH_3$/CI): m/e=379 (M+H).

Step 13.2B 2-(2-(3,5-dimethylphenyl)-3-{2-[4-(4-methanesulfonylamino-phenyl)butylamino]ethyl}-1H-indol-5-yl)-2-methylpropionic acid ethyl ester The reductive amination reaction of 2-[3-(2-aminoethyl)-2-(3,5-dimethylphenyl)-1H-indol-5-yl]-2-methylpropionic acid ethyl ester and 4-[4-(methanesulfonamido)phenyl] butyraldehyde was carried out according to the procedure of Example 14.1 Step B to give the titled compound in 43% yield as a stiff foam; virtually homogenous by TLC in 92.5:7.5 $CH_2Cl_2$—MeOH. 500 MHz $^1H$ NMR ($CDCl_3$) was consistent with the assigned structure. Mass spectrum (PB-$NH_3$/CI): m/e=604 (M+H).

Step 13.2C 2-[3-(2-{benzyloxycarbonyl-[4-(4-methanesulfonylaminophenyl)butyl]amino]ethyl)-2-(3,5-dimethyl-phenyl)-1H-indol-5-yl]-2-methylpropionic acid ethyl ester The reaction of 2-(2-(3,5-dimethylphenyl)-3-{2-[4-(4-methanesulfonylaminophenyl)butylamino]ethyl}-1H-indol-5-yl)-2-methylpropionic acid ethyl ester with benzyl chloroformate was carried out according to the procedure of Example 14.1 Step C, to give the titled compound in 72% yield as a stiff foam; homogeneous by TLC in 95:5 $CH_2Cl_2$—MeOH. 500 MHz $^1H$ NMR was complex, owing to the existence of rotamers, but was consistent with the assigned structure. Mass spectrum (ESI): m/e=738 (M+H).

Step 13.2D 2-[3-(2-{benzyloxycarbonyl-[4-(4-methanesulfonylamino-phenyl)butyl]amino}ethyl)-2-(3,5-dimethylphenyl)-1H-indol-5-yl]-2-methylpropionic acid The saponification of 2-[3-(2-{benzyloxycarbonyl-[4-(4-methanesulfonylamino-phenyl)butyl]amino}ethyl)-2-(3,5-dimethylphenyl)-1H-indol-5-yl]-2-methylpropionic acid ethyl ester was achieved according to the procedure of Example 14.1 Step D, except that the reaction time was increased to 30 hours, providing a quantitative yield of the titled compound as a powder, mp>102° C. (gradual; partial decomposition); homogeneous by TLC in 92.5:7.5 $CH_2Cl_2$—MeOH. 500 MHz $^1H$ NMR (DMSO-$d_6$) was complex, owing to rotamers, but was consistent with the assigned structure. Mass spectrum (ESI): m/e=710 (M+H).

Step 13.2E {2-[5-(1-diethylcarbamoyl-1-methylethyl)-2-(3,5-dimethylphenyl)-1H-indol-3-yl]ethyl}-[4-(4-methanesulfonylaminophenyl)butyl]carbamic acid benzyl ester A solution of 71.0 mg (0.1 mmol) of 2-[3-(2-{benzyloxycarbonyl-[4-(4-methanesulfonylamino-phenyl)butyl]amino}ethyl)-2-(3,5-dimethylphenyl)-1H-indol-5-yl]-2-methylpropionic acid, 53.0 mg (0.102 mmol) of PyBOP reagent, and 14.2 mL (10.3 mg; 0.102 mmol) of triethylamine in 400 mL of dry methylene chloride was stirred at room temperature in a stoppered flask. After 25 minutes, 15.5 mL (11.0 mg; 0.15 mmol) of diethylamine was added, followed after 4 hours by an additional 36.2 mL (25.6 mg; 0.35 mmol) of diethylamine. After 1 day, the solution was partitioned between 10 mL of 0.5N hydrochloric acid. The organic phase was washed with 10 mL of saturated aqueous sodium bicarbonate solution and then with 5 mL of saturated aqueous sodium chloride solution. The ethyl acetate phase was then dried (magnesium sulfate), filtered, and concentrated in vacuo at room temperature. The residue was purified by preparative TLC on 4 Analtech tapered silica gel plates (20×20 cm), which were developed in 94:6 $CH_2Cl_2$—MeOH. The product band from each plate was isolated, combined, and extracted with 94:6 $CH_2Cl_2$—MeOH. Concentration of the extracts in vacuo yielded 66.2 mg (87%) of a nearly colorless glass; virtually homogeneous by TLC in 95:5 $CH_2Cl_2$—MeOH. 500 MHz $^1H$ NMR ($CDCl_3$) was complex, owing to rotamers, but was consistent with the assigned structure. Mass spectrum (ESI): m/e=765 (M+H).

Step 13.2F 2-(2-(3,5-dimethylphenyl)-3-{2-[4-(4-methanesulfonylaminophenyl)-butylamino]ethyl}-1H-indol-5-yl)-N,N-diethylisobutyramide A mixture of 62.7 mg (0.082 mmol) of {2-[5-(1-diethylcarbamoyl-1-methylethyl)-2-(3,5-dimethylphenyl)-1H-indol-3-yl]ethyl}-[4-(4-methanesulfonylaminophenyl)butyl]carbamic acid benzyl ester, 30 mg of 20% palladium on carbon, 10 mL of glacial acetic acid, and 5 mL of absolute ethanol was shaken with hydrogen (48 psig) in a pressure vessel for 2 hours. The catalyst was removed by filtration through Celite under nitrogen, and the filtrate was concentrated in vacuo at room temperature. The residue was purified by preparative TLC on 4 Analtech tapered silica gel plates (20×20 cm), which were developed in 92.5:7.5:0.75 $CH_2Cl_2$—MeOH-concentrated $NH_4OH$. The product band from each plate was isolated, combined, and extracted with 92.5:7.5:0.75 $CH_2Cl_2$—MeOH-concentrated $NH_4OH$. Concentration of the extracts in vacuo yielded 47.2 mg (91%) of a glass; homogeneous by TLC in 92.5:7.5:0.75 $CH_2Cl_2$—MeOH-concentrated $NH_4OH$. 500 MHz $^1H$ NMR ($CDCl_3$) was consistent with the assigned structure. Mass spectrum (ESI): m/e=631 (M+H).

PREPARATION OF SYNTHETIC INTERMEDIATES

Step A 4-chloro-N-methoxy-N-methylbutyramide

To a solution of 4-chlorobutyryl chloride (10.0 g in 200 mL of dry methylene chloride) was added 10.4 g of N,O-dimethylhydroxylamine hydrochloride. The mixture was stirred under nitrogen and maintained below 25° C. by cooling in an ice bath as necessary while triethylamine (29.1 mL) was added dropwise over about 20 minutes, resulting in precipitation. After 1.5 hours at room temperature, the mixture was concentrated in vacuo. The residue was partitioned between 100 mL of diethyl ether and 100 mL of saturated aqueous sodium bicarbonate solution. The organic layer was washed with an additional 100 mL of saturated sodium bicarbonate, and the aqueous fractions were back-extracted with ether. The combined organic phases were dried over sodium sulfate, filtered, and concentrated in vacuo to give 10.5 g (90%) of an oil, which had satisfactory purity by $^1H$ NMR ($CDCl_3$). Mass spectrum (PB-$NH_3$/CI): m/e=166 (M+H).

Step B 3-chloropropyl 3,5-dimethylphenyl ketone

A solution of 10.2 mL (13.9 g; 72 mmol) 5-bromo-m-xylene in 200 mL of anhydrous tetrahydrofuran was stirred under nitrogen at −78° C. as 35.8 mL (84 mmol) of 2.5M n-butyllithium in tetrahydrofuran was added dropwise. After 15 minutes at −78° C., a solution of 10.0 g (60 mmol) of 4-chloro-N-methoxy-N-methylbutyramide (from Step A) in 30 mL of anhydrous tetrahydrofuran was added dropwise over 25–30 minutes. The resulting solution was maintained at −78° C. for 45 minutes and then warmed briefly to room temperature. The reaction was quenched by addition of 40 ml of 2N hydrochloric acid and then partitioned between ethyl acetate and water. The organic phase was washed with saturated aqueous sodium bicarbonate solution and then saturated aqueous sodium chloride solution. The organic solution was dried over sodium sulfate, filtered, and concentrated in vacuo. Flash chromatography of the residue afforded 8.91 g (70%) of an oil, which had satisfactory purity by $^1H$ NMR ($CDCl_3$).

Step AA 4-(4-nitrophenyl)butyric acid N-methoxy-N-methylamide

A stirred solution of 6.29 g (30 mmol) of 4-(4-nitrophenyl)butyric acid in 90 mL of dry methylene chloride (maintained under nitrogen and cooled in a water bath) was treated with 4.17 mL (3.03 g; 30 mmol) of triethylamine, followed by 13.26 g (30 mmol) of BOP reagent. After a few minutes, 3.22 g (33 mmol) of N,O-dimethylhydroxylamine hydrocholoride was added, followed by an additional 4.59 mL (3.33 g. 33 mmol) of triethylamine. After 2.25 hours, the solution was diluted with 200 mL of diethyl ether and washed successively with 3×100 mL of 2N hydrochloric acid, 1×100 mL and 2×50 mL of saturated aqueous sodium bicarbonate solution, and 1×50 mL of saturated aqueous sodium chloride solution. The organic phase was dried over magnesium sulfate, filtered, and concentrated in vacuo. Flash chromatography of the residue on silica gel (elution with 2:1 and then 3:2 hexane-EtOAc) afforded 6.27 g (83%) of crystals, mp 39.5°–41.5° C.; homogeneous by TLC in 1:1 hexane-EtOAc. 500 MHz $^1$H NMR (CDCl$_3$) was consistent with the assigned structure. Mass spectrum (PB-NH$_3$/CI): m/e=253 (M+H).

Step BB 4-(4-aminophenyl)butyric acid, N-methoxy-N-methylamide

A mixture of 6.05 g (24 mmol) of 4-(4-nitrophenyl)butyric acid, N-methoxy-N-methylamide, 50 mg of 10% palladium on carbon, and 200 mL of ethanol was shaken with hydrogen (initial hydrogen pressure 53 psig) for 1.5 hours, by which time hydrogen uptake had ceased and TLC indicated complete reaction. The mixture was filtered through Celite under nitrogen, and the filtrate was concentrated in vacuo to yield 5.29 g of an oil; homogeneous by TLC in 95:5 CH$_2$Cl$_2$—MeOH. 400 MHz $^1$H NMR (CDCl$_3$) was consistent with the assigned structure. Mass spectrum (PB-NH$_3$/CI): m/e=223 (M+H).

Step CC 4-[4-(methanesulfonamido)phenyl]butyric acid, N-methoxy-N-methylamide

A solution of 5.33 g (24 mmol) of 4-(4-aminophenyl)butyric acid, N-methoxy-N-methylamide in 48 mL of dry pyridine was stirred under nitrogen with cooling in an ice bath as 1.86 mL (2.75 g; 24 mmol) of methanesulfonyl chloride was added dropwise over about 15 minutes. After completion of the addition, the solution was allowed to warm to room temperature. After 1.5 hours, the solution was concentrated in vacuo at room temperature. The residue was diluted with 10 mL of methylene chloride and partitioned between a mixture of 100 mL of ethyl acetate+100 mL of tetrahydrofuran and 100 mL of 2N hydrochloric acid. The organic layer was washed with an additional 4×100 mL of 2N hydrochloric acid, then with 50 mL of saturated aqueous sodium bicarbonate solution, and finally with 20 mL of saturated aqueous sodium chloride solution. The organic phase was diluted with some tetrahydrofuran, dried over magnesium sulfate, and treated with charcoal. The mixture was filtered through Celite, and the filter cake was washed with additional tetrahydrofuran. Concentration of the filtrate in vacuo gave 4.39 g (61%) of crystals, mp 115°–117° C.; homogeneous by TLC in 95:5 CH$_2$Cl$_2$—MeOH. 400 MHz $^1$H NMR (DMSO-d$_6$) was consistent with the assigned structure. Mass spectrum (PB-NH$_3$/CI): m/e=301 (M+H).

Step DD 4-[4-(methanesulfonamido)phenyl]butyraldehyde

A mixture of 4.20 g (14 mmol) of 4-[4-(methanesulfonamido)phenyl]butyric acid, N-methoxy-N-methylamide and 100 mL of anhydrous tetrahydrofuran was stirred under nitrogen with cooling in an ice bath as 17.5 mL (17.5 mmol) of 1M lithium aluminum hydride in tetrahydrofuran was added gradually by syringe. After 0.75 hours, 70 mL of 5% potassium hydrogen sulfate solution (aqueous) was added cautiously by syringe. The mixture was then removed from the ice bath, diluted with 150 mL of water, and shaken with 150 mL of ethyl acetate. The milky aqueous phase was extracted with an additional 50 mL of ethyl acetate. The combined organic fractions were washed successively with 2×100 mL of 1N hydrochloric acid, then 50 mL of saturated aqueous sodium bicarbonate solution, and finally 50 mL of saturated aqueous sodium chloride solution.

The organic phase was dried over magnesium sulfate, filtered, and concentrated in vacuo. Flash chromatography of the residue on silica gel (elution with 3:2 hexane-EtOAc) yielded 2.47 g (73%) of an oil; homogeneous by TLC in 1:1 hexane-EtOAc). Upon storage in the freezer, solidification occurred (mp 41°–44° C.). 400 MHz $^1$H NMR (CDCl$_3$) was consistent with the assigned structure. Mass spectrum (PB-NH$_3$/CI): m/e=259 (M+NH$_4$).

Step AAA Ethyl 2-(4-hydrazinophenyl)acetate hydrochloride and 2-(4-hydrazinophenyl)acetic acid hydrochloride This compound (a mixture of the ethyl ester and the carboxylic acid) was prepared from 13.4 g (75 mmol) of ethyl 2-(4-aminophenyl)acetate, by diazotization and stannous chloride reduction of the diazonium salt, according to the method of L. J. Street, et al., *J. Med. Chem.*, 36, 1529 (1993). The material was obtained in two crops. The first crop consisted of 6.40 g of powder, mp>200° C. By 400 MHz $^1$H NMR (DMSO-d$_6$), this material consisted of a mixture of carboxylic acid and ethyl ester in approximately a 4:3 molar ratio. Mass spectrum (PB-NH$_3$/CI): 195 (arylhydrazonium cation for the ethyl ester). The second crop consisted of 4.60 g of powder, mp>180° C. By 400 MHz $^1$H NMR (DMSO-d$_6$), this material consisted of a mixture of carboxylic acid and ethyl ester in approximately a 7:1 molar ratio. After adjustment for the mixture composition of the two crops, the estimated total yield was 69%. Because esterification of any carboxylic acid occurs in the next step, both the ester and the acid react to give the same product.

Step AAAA Ethyl (±)-2-(4-nitrophenyl)propionate

To a solution of 9.76 g (50 mmol) of (±)-2-(4-nitrophenyl)propionic acid in 150 mL of absolute ethanol was added 3.0 mL of concentrated sulfuric acid. The resulting solution was stirred at reflux under nitrogen. After 6 hours, the solution was cooled and stirred vigorously as 250 mL of saturated aqueous sodium bicarbonate solution was added gradually (Caution: foaming). The mixture was then partitioned between 750 mL of ethyl acetate and 500 mL of water. The organic layer was washed with 100 mL of saturated aqueous sodium bicarbonate solution and then with 100 mL of saturated aqueous sodium chloride solution. The organic phase was dried over magnesium sulfate, filtered, and concentrated in vacuo to give 10.86 g (97%) of an oil; homogeneous by TLC in 9:1 hexane-ethyl acetate. 400 MHz $^1$H NMR (CDCl$_3$) was consistent with the assigned structure.

Step BBBB Ethyl 2-methyl-2-(4-nitrophenyl)propionate

A suspension of 924 (23 mmol) of sodium hydride (60% in oil) in 21 mL of dry N,N-dimethylformamide was stirred under nitrogen in an ice bath as a solution of 4.68 g (21 mmol) of ethyl (±)-2-(4-nitrophenyl)propionate in 20.5 mL of dry N,N-dimethylformamide was added gradually over about 10 minutes. An intense violet color developed during the addition. The mixture was then allowed to warm to room temperature. After about 1 hour, the mixture was again cooled in an ice bath as a solution of 1.44 mL (3.28 g; 23 mmol) of methyl iodide in 5 mL of dry N,N-dimethylformamide was added dropwise by syringe over about 10 minutes, while maintaining the internal temperature at 10°–15° C. The mixture was allowed to warm to room temperature, and the color changed to brown. After 1 hour, an additional 187 mL (426 mg, 3 mmol) of iodomethane was added. By the next day, the mixture consisted of a suspension of some grayish solid in a golden liquid. It was stirred vigorously and quenched by gradual addition of 10 mL of 5% aqueous potassium bisulfate solution. The mixture was partitioned between 400 mL of diethyl ether and 400 mL of water. The organic layer was washed with an additional 3×400 mL of water and then with 50 mL of saturated aqueous sodium chloride solution. The organic phase was then dried over magnesium sulfate, filtered, and concentrated in vacuo. Flash chromatography of the residue on silica gel (elution with 19:1 hexane-ethyl acetete) yielded 4.31 g (87%) of an oil; homogeneous by TLC in 9:1 hexane-ethyl acetete. 400 MHz $^1$H NMR (CDCl$_3$) was consistent with the assigned structure.

Step CCCC Ethyl 2-(4-aminophenyl)-2-methylpropionate

A mixture of 4.27 g (18 mmol) of ethyl 2-methyl-2-(4-nitrophenyl)propionate, 200 mg of 10% palladium on carbon, and 120 mL of absolute ethanol was shaken with hydrogen (initial hydrogen pressure 47 psig) in a pressure vessel for 2 hours. The catalyst was removed by filtration through Celite under nitrogen, and the filter cake was washed with additional ethanol. Concentration of the filtrate in vacuo at up to 50° C. gave 3.74 g (100%) of an oil; homogeneous by TLC in 4:1 hexane-EtOAc. 400 MHz $^1$H NMR (CDCl$_3$) was consistent with the assigned structure. Mass spectrum (ESI): m/e=208 (M+H).

Step DDDD Ethyl 2-(4-hydrazinophenyl)-2-methylpropionate

A solution of 3.725 g (18 mmol) of ethyl 2-(4-aminophenyl)-2-methylpropionate in 18 mL of concentrated hydrochloric acid was stirred at −10° to −5° C. in an ice-acetone bath as a solution of 1.29 g (18.7 mmol) of sodium nitrite in 7.5 mL of water was added dropwise over about 15 minutes. Stirring was continued at this temperature for an additional 30 minutes. Next, a small amount of insoluble solid was removed by filtration into a cold receiving flask. The filtrate was then added dropwise over 10–15 minutes to a solution of 20.3 g (90 mmol) of stannous chloride dihydrate in 14.5 mL of concentrated hydrochloric acid stirred under nitrogen in an ice-acetone bath. The addition was carried out at such a rate that the internal temperature remained at about −5° C. A gummy material separated during the addition. After completion of the addition, stirring was continued at −10° to −5° C. for 1 hour. The aqueous phase was decanted, and the residual gum was dissolved in 250 mL of ethyl acetate. The ethyl acetate solution was treated cautiously with 250 mL of saturated aqueous sodium bicarbonate solution and shaken in a separatory funnel. The ethyl acetate layer was washed with 50 mL of saturated aqueous sodium chloride solution. The entire mixture was filtered before separation of the phases. The ethyl acetate phase was dried over magnesium sulfate, filtered, and concentrated in vacuo at room temperature to yield 2.59 g (65%) of an oil. 500 MHz $^1$H NMR (CDCl$_3$) was consistent with the assigned structure and indicated that only minor impurities were present.

Following a procedure similar to that described in EXAMPLES 13.1 and 13.2, the following compounds were prepared:

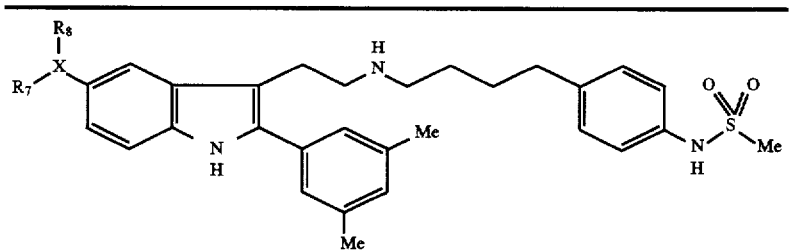

| Example | X—R$_7$R$_8$ | m/e |
|---|---|---|
| 13A | CH$_2$COOEt | 576 (M + H) |
| 13B | CH$_2$CON(Me)$_2$ | 575 (M + H) |
| 13C | CH(Me)COOEt | 590 (M + H) |
| 13D | C(Me)$_2$COOEt | 604 (M + H) |
| 13E | CH(Me)CON(Et)$_2$ | 617 (M + H) |
| 13F | C(Me)$_2$CON(Me)$_2$ | 603 (M + H) |
| 13G | C(Me)$_2$CON(Pr)$_2$ | 659 (M + H) |

EXAMPLE 14.1

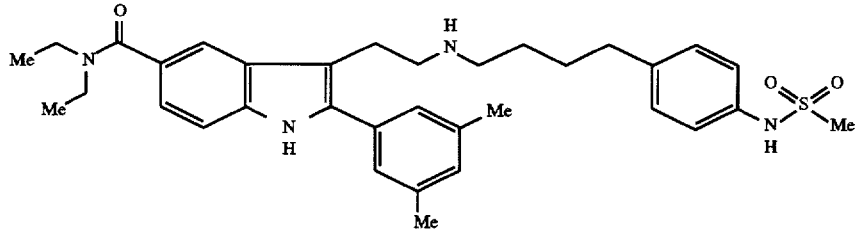

2-(3,5-dimethyphenyl)-3-{2-[4-(4-methanesulfonylaminophenyl)-butylamino]ethyl}-1H-indole-5-carboxylic acid diethylamide Step 14.1A 3-(2-aminoethyl)-2-(3,5-dimethylphenyl)-1H-indole-5-carboxylic acid ethyl ester A mixture of 7.60 g (50 mmol) of 4-hydrazinobenzoic acid, 10.55 g (50 mmol) of 3-chloropropyl 3,5-dimethylphenyl ketone, and 200 mL of absolute ethanol was stirred under nitrogen and heated to reflux. After 12 hours, the mixture was cooled and filtered. The solid on the filter was washed with additional small volumes of ethanol. The filtrate was treated with 4 mL of concentrated sulfuric acid and stirred at reflux under nitrogen for 4 days. The cooled mixture was stirred in an ice bath as a solution of sodium ethoxide (21% w/w in ethanol) was added dropwise under nitrogen until the mixture was basic by pH paper. The mixture was filtered and concentrated in vacuo at 30° C. The residue was partitioned between diethyl ether and water, with some saturated aqueous sodium chloride solution added to assist in separation of the layers. The aqueous phase was washed with an additional 100 mL of ether. The combined organic extracts were dried over sodium sulfate, filtered, and concentrated in vacuo. The residual gum was flash chromatographed on silica gel (elution with 97:3:0.3 and then 95:5:0.5 $CH_2Cl_2$—MeOH-concentrated $NH_4OH$). Concentration of the product fractions yielded 4.03 g of pure product as a stiff foam (virtually homogeneous by TLC in 95:5:0.5 $CH_2Cl_2$—MeOH-concentrated $NH_4OH$). Concentration of mixed fractions yielded an additional 0.93 g, which was rechromatographed to provide an additional 0.77 g of pure material, for a total yield of 4.80 g (29%). 400 MHz $^1H$ NMR ($CDCl_3$) was consistent with the assigned structure. Mass spectrum ($PB-NH_3/CI$): m/e=337 (M+H).

Step 14.1B 2-(3,5-dimethylphenyl)-3-{2-[4-(4-methanesulfonylaminophenyl)butylamino]ethyl}-1H-indole-5-carboxylic acid ethyl ester To a dry flask were added 672 mg (2.0 mmol) of 3-(2-aminoethyl)-2-(3,5-dimethylphenyl)-1H-indole-5-carboxylic acid ethyl ester, 530 mg (2.2 mmol) of 4-[4-(methanesulfonamido)phenyl]-butyraldehyde, 1.20 g (10 mmol) of magnesium sulfate, and a magnetic stirring bar. The flask was purged with nitrogen, cooled to −10° to −5° C. in an ice-methanol bath, and stirred as 4 mL of dry $CDCl_3$ was introduced gradually by syringe. The mixture was stirred under nitrogen for 15 minutes. Next, the septum was removed, and 100 mg (2.6 mmol) of sodium borohydride was added rapidly. The septum was immediately replaced, and the system was again purged with nitrogen. The mixture was stirred under nitrogen at about −5° C. as 4 mL of dry methanol was added gradually by syringe. After 20 minutes at this temperature, the reaction was quenched by gradual syringe addition of 1 mL of acetone to destroy excess sodium borohydride. After a few more minutes, the mixture was removed from the cooling bath and partitioned between 25 mL of ethyl acetate and 25 mL of water. The organic layer was washed with 10 mL of saturated aqueous sodium chloride solution, then dried over sodium sulfate, filtered, and concentrated in vacuo. The residue was flash chromatographed on silica gel (elution with 97:3 and then 95:5 $CH_2Cl_2$—MeOH). Concentration of the pooled product fractions in vacuo yielded 663 mg (59%) of a foam; virtually homogeneous by TLC (92.5:7.5 $CH_2Cl_2$—MeOH). 400 MHz $^1H$ NMR ($CDCl_3$+small amount of $DMSO-d_6$) was consistent with the assigned structure. Mass spectrum (ESI): m/e=562 (M+H).

Step 14.1C 3-(2-{benzyloxycarbonyl-[4-(4-methanesulfonylaminophenyl)butyl]amino}ethyl)-2-(3,5-dimethylphenyl)-1H-indole-5-carboxylic acid ethyl ester A solution of 646 mg (1.15 mmol) of 2-(3,5-dimethylphenyl)-3-{2-[4-(4-methanesulfonylaminophenyl)butylamino]ethyl}-1H-indole-5-carboxylic acid ethyl ester in 5 mL of dry methylene chloride and 5 mL of anhydrous tetrahydrofuran was stirred under nitrogen and cooled to −78° C. in a dry ice-acetone bath as 200 mL of N,N-diisopropylethylamine was added, followed by gradual addition of 173 mL (207 mg; 1.15 mmol, based on 95% purity) of benzyl chloroformate was added gradually by syringe. After 30 minutes, the solution was removed from the cooling bath and allowed to warm to room temperature. It was then partitioned between 25 mL of ethyl acetate and 25 mL of 5% potassium bisulfate aqueous solution. The organic layer was washed with an additional 25 mL of 5% potassium bisulfate and then with 10 mL of saturated aqueous sodium chloride solution. The organic phase was dried (magnesium sulfate), filtered, and concentrated in vacuo. Flash chromatography of the residue on silica gel (elution with 98:2 $CH_2Cl_2$—MeOH) afforded 611 mg (76%) of a foam; homogeneous by TLC in 95:5 $CH_2Cl_2$—MeOH. 500 MHz $^1H$ NMR was complex, owing to the existence of rotamers, but was consistent with the assigned structure. Mass spectrum (ESI): m/e=696 (M+H).

Step 14.1D 3-(2-{benzyloxycarbonyl-[4-(4-methanesulfonylaminophenyl)butyl]amino}ethyl)-2-(3,5-dimethylphenyl)-1H-indole-5-carboxylic acid A solution of 600 mg (0.862 mmol) of 3-(2-{benzyloxycarbonyl-[4-(4-methanesulfonylaminophenyl)butyl]amino}ethyl)-2-(3,5-dimethylphenyl)-1H-indole-5-carboxylic acid ethyl ester in 18 mL (9 mmol) of 0.50N potassium hydroxide in methanol was stirred at about 60° C. as 2.0 mL of water was added gradually. Stirring was continued at 60°–65° C. under nitrogen for 10 hours. The cooled mixture, which contained a white precipitate, was concentrated to small volume in vacuo. The residual suspension was partitioned between 25 mL of ethyl acetate and 25 mL of 0.5N hydrochloric acid. After the aqueous layer was separated, precipitation began in the ethyl acetate phase. Dilution with 25 mL of tetrahydrofuran redissolved the precipitate. The aqueous phase was back-extracted with 10 mL of ethyl acetate+10 mL of tetrahydrofuran. The combined organic phases were dried over magnesium sulfate, filtered, and concentrated in vacuo. The residual solid was triturated with diethyl ether, collected on a filter, and washed with some additional ether to give (after drying) 573 mg (100%) of a powder, mp 211.5°–213° C.; virtually homogeneous by TLC(92.5:7.5 $CH_2Cl_2$—MeOH). 500 MHz $^1H$ NMR ($DMSO-d_6$) was consistent with the assigned structure. Mass spectrum (ESI): m/e=668 (M+H).

Step 14.1E {2-[5-diethylcarbamoyl-2-(3,5-dimethylphenyl)-1H-indol-3-yl]ethyl}-[4-(4-methanesulfonylaminophenyl)butyl]carbamic acid benzyl ester To a suspension of 668 mg (0.703 mmol) of 3-(2-benzyloxycarbonyl-[4-(4-methanesulfonylaminophenyl)butyl]amino}ethyl)-2-(3,5-dimethylphenyl)-1h-indole-5-carboxylic acid in 2.7 mL of dry methylene chloride and 2.7 mL of anhydrous tetrahydrofuran were added 366 mg (0.703 mmol) of PyBOP reagent and 98 mL (71.0 mg; 0.703 mmol) of triethylamine. The resulting solution was stirred under nitrogen at room temperature for 20 minutes. Next, 109 mL (77.1 mg; 1.05 mmol) of diethylamine was added, and stirring was continued for 4 hours. The solution was then partitioned between ethyl acetate and saturated aqueous sodium bicarbonate solution. The organic layer was dried over sodium sulfate, filtered, and concentrated in vacuo. Flash chromatography of the residue on silica gel (gradient elution with 1–4% MeOH in $CH_2Cl_2$) afforded 440 mg (87%) of a stiff foam; homogeneous by TLC in 95:5 $CH_2Cl_2$—MeOH. 500 MHz $^1H$ NMR ($CDCl_3$) was complex, owing to rotamers, but was consistent with the assigned structure. Mass spectrum (ESI): m/e=723 (M+H).

Step 14.1F 2-(3,5-dimethylphenyl)-3-{2-[4-(4-methanesulfonylaminophenyl)butylamino]ethyl}-1H-indole-5-carboxylic acid diethylamide A mixture of 435 mg (0.602 mmol) of {2-[5-diethylcarbamoyl-2-(3,5-dimethylphenyl)-1H-indol-3-yl]

ethyl}-[4-(4-methanesulfonylaminophenyl)butyl]carbamic acid benzyl ester. 100 mg of 20% palladium hydroxide on carbon, and 50 mL of 2-methoxyethanol was shaken with hydrogen (42 psig) in a pressure vessel for 2.25 hours. The catalyst was removed by filtration through Celite, and the filtrate was concentrated in vacuo. Purification of the residue by flash chromatography on silica gel (gradient elution with 5–10% MeOH in $CH_2Cl_2$) yielded 353 mg (100%) of a stiff foam; homogeneous by TLC in 95:5:0.5 $CH_2Cl_2$—MeOH-concentrated $NH_4OH$. 500 MHz $^1H$ NMR ($CDCl_3$) was consistent with the assigned structure. Mass spectrum (ESI): m/e=589 (M+H).

EXAMPLE 14.2

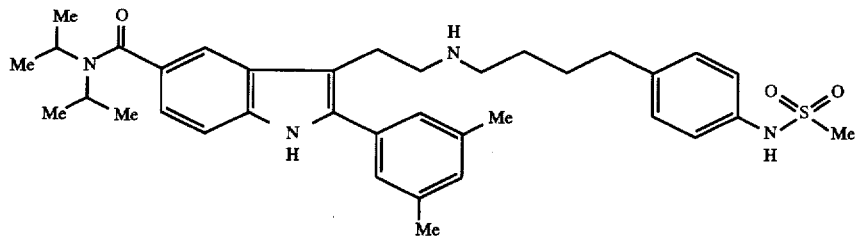

2-(3,5-dimethylphenyl)-3-[2-[4-[4-(methanesulfonylamino)phenyl]-butylamino]ethyl]-1H-indole-5-carboxylic acid diisopropylamide Step 14.2A N,N-diisopropyl-4-nitrobenzamide A solution of 3.51 mL (2.53 g, 25 mmol) of diisopropylamine and 3.62 mL (2.63 g, 26 mmol) of triethylamine in 50 mL of anhydrous tetrahydrofuran was stirred under nitrogen and maintained at −5° C. as a solution of 4.11 g (22.1 mmol) in 10 mL of anhydrous tetrahydrofuran was added dropwise over 15 minutes. The mixture was allowed to warm gradually to room temperature. After 2 hours, the mixture was filtered, and the filtrate was partitioned between diethyl ether and 1N hydrochloric acid. The organic phase was then washed with saturated sodium carbonate₃ solution, then dried over sodium sulfate and filtered. The filtrate was concentrated in vacuo, and the residue was flash-chromatographed on silica gel (gradient elution with 2–5% MeOH in $CH_2Cl_2$) to yield 4.77 g (86%) of yellowish crystals, mp 141.5°–142° C.; homogeneous by TLC 2:1 hexane-EtOAc. 500 MHz $^1H$ NMR ($CDCl_3$) was consistent with the assigned structure.

Step 14.2B 4-amino-N,N-diisopropylbenzamide

A mixture of 4.70 g (18.8 mmol) of N,N-diisopropyl-4-nitrobenzamide, 200 mg of 10% palladium on carbon, and 200 mL of 2-methoxyethanol was shaken with hydrogen at approx. 50 psig for 6.5 hours. The catalyst was removed by filtration through diatomaceous earth under nitrogen. Concentration of the filtrate in vacuo afforded a quantitative yield of a yellow solid, mp 169.5°–170° C.; homogeneous by TLC in 95:5 $CH_2Cl_2$—MeOH. 500 MHz $^1H$ NMR ($CDCl_3$) was consistent with the assigned structure. Mass spectrum (PB-$NH_3$/CI): m/e=221 (M+H).

Step 14.2C 4-hydrazino-N,N-diisopropylbenzamide

Treatment of 4.2 g (19 mmol) of 4-amino-N,N-diisopropylbenzamide with 15 mL of concentrated hydrochloric acid and 10 mL of water was followed by agitation. The resulting solution was maintained at approx. −3° C. as a solution of 1.32 g (19.1 mmol) of sodium nitrite in 9 mL of water was added dropwise. After being stirred for an additional 30 minutes at this temperature, this solution was added portionwise to a vigorously stirred solution of 15.1 g (66.7 mmol) of stannous chloride dihydrate in 15 mL of concentrated hydrochloric acid, which was maintained at about −10° C. After completion of the addition, the mixture was stirred at this temperature for 5 minutes and then allowed to warm to room temperature. At this point, it was again cooled and basified by gradual addition of 25 mL of 50% sodium hydroxide. The resulting precipitate was collected on a filter and partitioned between tetrahydrofuran and 5N sodium hydroxide in a 2:1 ratio. The aqueous layer was extracted 3 times with tetrahydrofuran. The combined organic fractions were concentrated in vacuo. The residue was taken up in $CH_2Cl_2$—EtOAc, dried over sodium sulfate, filtered, and reconcentrated to give 3.55 g (80%) of semi-solid; homogeneous by TLC in 95:5 $CH_2Cl_2$—MeOH. 500 MHz $^1H$ NMR ($CDCl_3$) was consistent with the assigned structure. Mass spectrum (PB-$NH_3$/CI): m/e=236 (M+H).

Step 14.2D 3-(2-aminoethyl)-2-(3,5-dimethylphenyl)-1H-indole-5-carboxylic acid diisopropylamide A solution of 3.51 g (14.9 mmol) 4-hydrazino-N,N-diisopropylbenzamide (from Step 3) in 18 mL of 2-methoxyethanol was stirred at 100° C. under nitrogen as 3.77 g (17.8 mmol) of 3-chloropropyl 3,5-dimethylphenyl ketone in 7 mL of 2-methoxyethanol was added dropwise over 20 minutes. The solution was stirred at this temperature for 5 hours, then cooled and filtered to remove a solid (a tetrahydropyridazine by-product). The filtrate was concentrated in vacuo, and the residue was purified by flash chromatography on silica gel (elution with 95:5 $CH_2Cl_2$—MeOH followed by a gradient of 98:2:0.2 to 92:8:0.8 $CH_2Cl_2$—MeOH-concd. $NH_4OH$) gave 1.78 g (31%) of a brownish, stiff foam; satisfactory purity by TLC in 95:5:0.5 $CH_2Cl_2$—MeOH-concd. $NH_4OH$. 500 MHz $^1H$ NMR ($CDCl_3$) was consistent with the assigned structure. Mass spectrum (PB-$NH_3$/CI): m/e=392.2 (M+H).

Step 14.2E 2-(3,5-dimethylphenyl)-3-[2-[4-[4-(methanesulfonylamino)phenyl]butylamino]ethyl-1H-indole-5-carboxylic acid diisopropylamide A mixture of 100 mg (0.255 mmol) 3-(2-aminoethyl)-2-(3,5-dimethylphenyl)-1H-indole-5-carboxylic acid diisopropylamide, 67.7 mg (0.281 mmol) of 4-[4-(methanesulfonamido)phenyl]butyraldehyde, and 153 mg (1.28 mmol) of anhydrous magnesium sulfate was purged with nitrogen and cooled in an ice-methanol bath at about −10° to −5° C. as 0.60 mL of dry $CDCl_3$ was added gradually by syringe. The mixture was stirred under nitrogen at this temperature for 35 minutes. The septum was removed just long enough to add 12.5 mg (0.332 mmol) of sodium borohydride, and the solution was repurged with nitrogen. The mixture was stirred at −10° to −5° C. as 0.40 mL of dry methanol was added gradually, and stirring was continued at this temperature for several minutes. The mixture was partitioned between ethyl acetate and dilute sodium hydroxide (pH 10). The ethyl acetate phase was dried over sodium sulfate, filtered, and concentrated in vacuo. The residue was purified by flash chromatography on silica gel (gradient elution with 99:1:0.1 to 90:10:1 CH$_2$Cl$_2$—MeOH-concd. NH$_4$OH) to give 16.0 mg of a yellow, stiff foam, and an additional 13.8 mg was obtained by preparative TLC of mixed fractions (developed in 95:5:0.5 CH$_2$Cl$_2$—MeOH-concd. NH$_4$OH), affording a total of 29.8 mg (19%) of the title compound; homogeneous by TLC in 90:10:1 CH$_2$Cl$_2$—MeOH-concd. NH$_4$OH. 500 MHz $^1$H NMR (CDCl$_3$) was consistent with the assigned structure. Mass spectrum (ESI): m/e=617.5 (M+H).

Following a procedure similar to that described above, the following compounds were prepared:

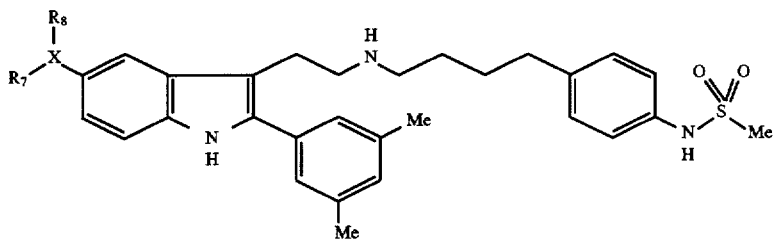

| Example | X—R$_7$R$_8$ | m/e |
| --- | --- | --- |
| 14A | COOEt | 562 (M + H) |
| 14B | CO—N(CH$_2$CH$_2$OH) | 621 (M + H) |
| 14C | CO—NHEt | 562 (M + H) |
| 14D | CO—NH-cyclopropyl | 573 (M + H) |
| 14E | Me—(CH$_2$)$_3$—N(Et)—C(O)Me | 617 (M + H) |
| 14F | (Me)$_2$CH—N(Et)—C(O)Me | 603 (M + H) |
| 14G | cyclohexyl—N(Me)—C(O)Me | 643 (M + H) |
| 14H | HO—CH$_2$CH$_2$—N(Me)—C(O)Me | 591 (M + H) |
| 14I | (Me)$_3$C—N(Me)—C(O)Me | 603 (M + H) |
| 14J | Me—CH$_2$—N(CH$_2$Me)—C(O)Me | 617 (M + H) |
| 14K | HO—CH$_2$CH$_2$—N(Me)—C(O)Me | 605 (M + H) |
| 14L | Ph—N(Me)—C(O)Me | 623 (M + H) |

-continued
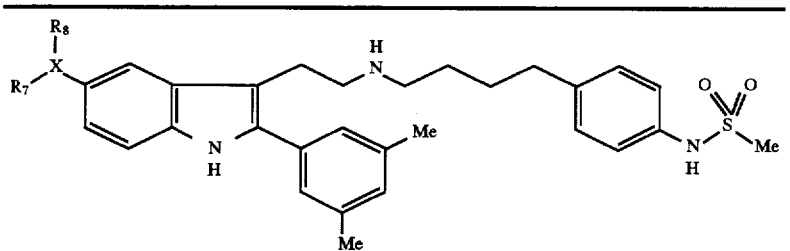
| Example | X—R₇R₈ | m/e |
|---|---|---|
| 14M | Me-N(Me)-C(=O)- | 561 (M + H) |
| 14N | MeO-CH₂CH₂-N(Me)-C(=O)- | 605 (M + H) |
| 14O | MeO-CH₂CH₂-N(CHMe₂)-C(=O)- | 633 (M + H) |
| 14P | MeO-CH₂CH₂-N(CMe₃)-C(=O)- | — |
| 14Q | Me-CH₂-N(CMe₃)-C(=O)- | 617 (M + H) |
| 14R | (Me₂CHCH₂)₂N-C(=O)- | 645 (M + H) |
| 14S | (F₃C-CH₂)₂N-C(=O)- | 697 (M + H) |
EXAMPLE 15
Following a procedure similar to that described in EXAMPLES 8 and 11, the following compounds were prepared:

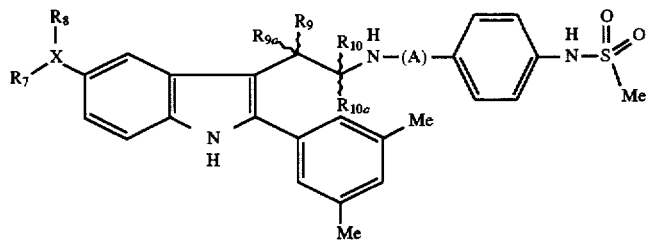

| Example | X — R₇R₈ | R₉,R₉ₐ:R₁₀,R₁₀ₐ | (CH₂)n = A |
|---|---|---|---|
| 15A | NH — CON(Et)₂ | Me,H:H,H | 4 |
| 15B | NH — CO — Ph | Me,H:H,H | 4 |
| 15C | NH — CO — N(Me)₂ | Me,H:H,H | 2 |
| 15D | NH — CO — N(Me)₂ | Me,H:H,H | 4 |
| 15E | N(CH₂Ph)₂ | Me,H:Me,H | 4 |
| 15F | NHC(O)Ph | CH₂CH₂OH,H:H,H | 4 |
| 15G | SO₂Me | Me,H:H,H | 4 |
| 15H | NHC(O)Ph | CH₂CH₂OMe,H:H,H | 4 |
| 15I | O — CH₂Ph | H,H:Me,Me | 4 |

EXAMPLE 16

Following a procedure similar to that described in EXAMPLE 14.1, the following compounds were prepared:

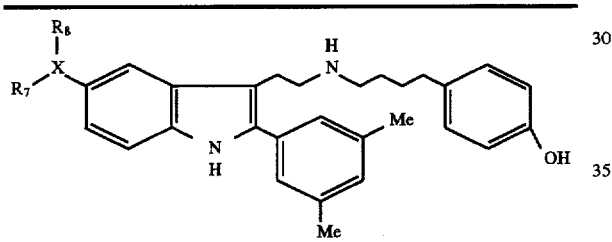

| Example | X — R₇R₈ | m/e |
|---|---|---|
| 16A | COO — CH₂CH₃ | 485 (M + H) |
| 16B | COOH | 457 (M + H) |
| 16C | CO — N(CH₂CH₃)₂ | 512 (M + H) |
| 16D | CO — NH — CH₂Ph | 546 (M + H) |
| 16E | CO — N(CH₃)₂ | 484 (M + H) |
| 16F | CO — N(iBu)₂ | 568 (M + H) |

EXAMPLE 17

Following a procedure similar to that described in EXAMPLES 9 and 14.1, the following compounds were prepared:

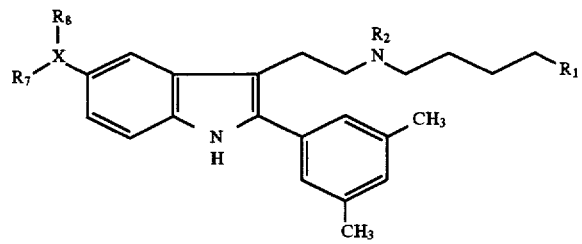

| Example | R₁ | X — R₇R₈ | R₂ | m/e |
|---|---|---|---|---|
| 17A | Ph-4-NH(SO₂Me) — COEt | NHCOEt | | 617 (M + H) |
| 17B | Ph-4-NHSO₂CH₂ — C(O)Me | SO₂CH₂C(O)Me | | 652 (M + H) |
| 17C | Ph-4-NHSO₂CH₂ — C(O)Me | SO₂Me | | 610 (M + H) |
| 17D | Ph-4-SO₂NHMe | COOEt | | 562 (M + H) |
| 17E | Ph-4-NO₂ | COOEt | | 514 (M + H) |
| 17F | Ph-4-NHSO₂Me | CON(Et)₂ | Et | 617 (M + H) |
| 17G | Ph-4-SO₂NHMe | CON(Et)₂ | | 589 (M + H) |

-continued

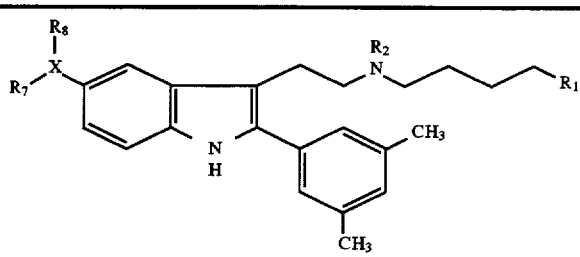

| Example | R₁ | X—R₇R₈ | R₂ | m/e |
|---------|-----|---------|-----|------|
| 17H | Ph-4-SO₂NHMe | CON(iBu)₂ | | 645 (M + H) |
| 17I | Ph-4-SO₂NHMe | CON(cyclohexyl)Et | | 643 (M + H) |
| 17J | Ph-4-NO₂ | CON(iBu)₂ | | 597 (M + H) |
| 17K | Ph-4-NH₂ | CON(iBu)₂ | | 567 (M + H) |
| 17L | Ph-4-SMe | COOEt | | 515 (M + H) |
| 17M | Ph-4-SMe | CON(Et)₂ | | 542 (M + H) |
| 17N | Ph-4-S(O)Me | CON(Et)₂ | | 558 (M + H) |
| 17O | Ph-4-S(O)₂Me | CON(Et)₂ | | 574 (M + H) |
| 17P | Ph-4-SMe | CON(iBu)₂ | | 598 (M + H) |
| 17Q | Ph-4-S(O)Me | CON(iBu)₂ | | 614 (M + H) |
| 17R | Ph-4-S(O)₂Me | CON(iBu)₂ | | 630 (M + H) |
| 17S | Ph-4-NH[C=N(CONH₂)]NHMe | CON(iBu)₂ | | 666 (M + H) |
| 17T | Ph-4-NH[C=N(CN)]NHMe | CON(iBu)₂ | | 648 (M + H) |
| 17U | Ph-4-F | CON(iBu)₂ | | — |
| 17V | Ph-4-SO₂N(Me)₂ | COOEt | | 576 (M + H) |
| 17W | Ph-4-SO₂N(Me)₂ | CON(iBu)₂ | | 659 (M + H) |
| 17X | Ph-4-SO₂N(Me)₂ | CON(Et)₂ | | 603 (M + H) |
| 17Y | Ph-4-SO₂N(Me)₂ | CON(Et)cyclohexyl | | 657 (M + H) |

EXAMPLE 18

Following a procedure similar to that described EXAMPLES 4.1 and 5.1, the following compounds were prepared:

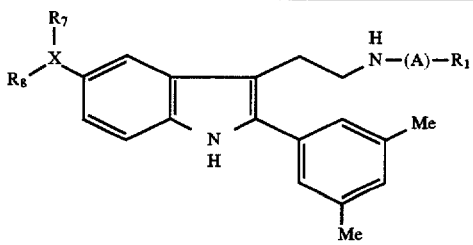

| Example | R₇—X—R₈ | —(A)—R₁ | M/E |
|---------|---------|---------|-----|
| 18A | H | 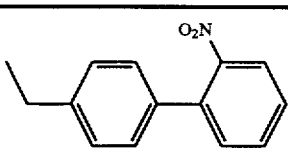 | |
| 18B | H | 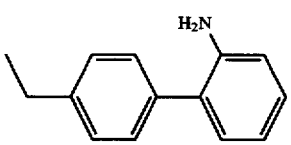 | |
| 18C | H | 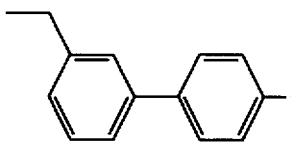 | |

-continued

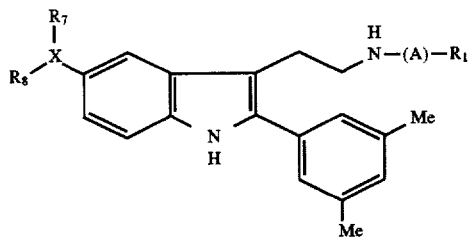

| Example | R₇—X—R₈ | —(A)—R₁ | M/E |
|---|---|---|---|
| 18D | NHCO—N(Et)₂ | 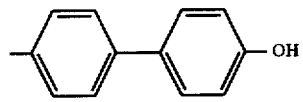 | |
| 18E | SO₂Me | 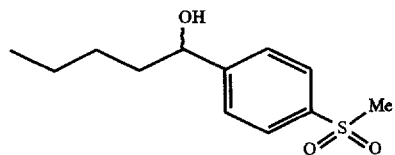 | 569 (M + H) |

EXAMPLE 19

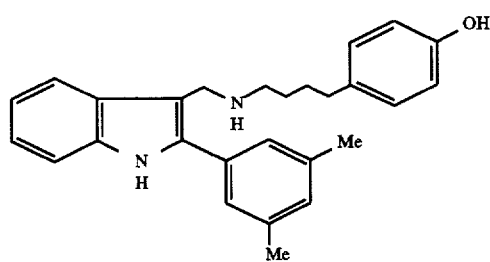

4-(4-{[2-(3,5-dimethylphenyl)-1H-indol-3-ylmethyl]amino}butyl)phenol

Step 19A [2-(3,5-dimethylphenyl)-1H-indol-3-ylmethyl]dimethylamine

To 2.53 g glacial acetic acid was added 2.0 g dimethyl amine (40% aqueous solution) followed by 1.37 g fomalin (37% solution) then 4.0 g 2-(3,5-dimethylphenyl)-1H-indole and the mixture stirred at 0° C. After 15 minutes, 40 mL ethanol was added and the mixture allowed to warm to room temperature. After 1 hour at room temperature, the reaction was quenched by pouring into 50 mL of 1N sodium hydroxide. The resulting mixture was extracted with methylene chloride (4×10 mL) and the combined organics dried over potassium carbonate. Concentration in vacuo gave the crude title compound (4.15 g).

Step 19B [2-(3,5-dimethylphenyl)-1H-indol-3-ylmethyl]trimethylammonium iodide

To a solution of [2-(3,5-dimethylphenyl)-1H-indol-3-ylmethyl]dimethylamine (350 mg in 4 mL diethyl ether) was added 0.5 mL iodomethane and the mixture stirred at room temperature. After 3 hours, the mixture was filtered and the solids dried in vacuo to provide the crude title compound. (414 mg).

Step 19C 4-(4-{[2-(3,5-dimethylphenyl)-1H-indol-3-ylmethyl]amino}butyl)phenol

To a solution of 4-(4-{[2-(3,5-dimethylphenyl)-1H-indol-3-ylmethyl]amino}butyl)phenol (20 mg in 1.5 mL dry methanol) was added 47 mg 4-(4-aminobutyl)phenol and the mixture stirred at room temperature. After 32 hours, the mixture was concentrated in vacuo and the residue purified by preparative TLC on silica gel (methylene chloride:methanol, 96:4) to give the title compound (12.3 mg). m/e=234 (base)

Following a procedure similar to that described above, the following compounds were prepared:

| Example | R₁ | (CH₂)n = A | m/e |
|---|---|---|---|
| 19A | Ph-4-OMe | 4 | 234 (base) |
| 19B | Ph-4-OH | 3 | 234 (base) |
| 19C | Ph-4-OH | 2 | 234 (base) |

EXAMPLE 20

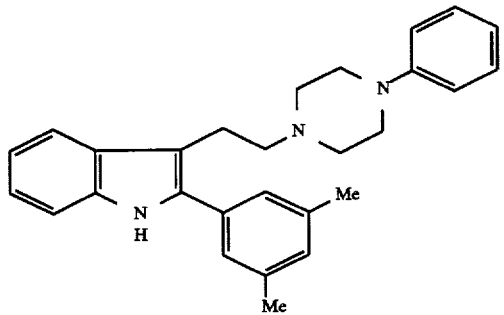

2-(3,5-dimethylphenyl)-3-[2-(4-phenylpiperazin-1-yl)ethyl]-1H-indole

Step 20A 1-[2-(3,5-dimethylphenyl)-1H-indol-3-yl]-2-(4-phenylpiperazin-1-yl)ethane-1,2-dione To a solution of 2-(3,5-dimethylphenyl)-1H-indole (75 mg in 4 mL dry diethyl ether) was added dropwise 0.032 mL oxalyl chloride and the mixture stirred at room temperature. After 45 minutes, the mixture was concentrated in vacuo and re-solvated in 3 mL dry tetrahydrofuran then 0.104 mL of 1-phenylpiperazine was added dropwise. After 20 minutes, the reaction was quenched by the addition of water and the resulting mixture extracted with ethyl acetate. The organic portion was washed with brine, dried over magnesium sulfate and the concentrate purified by flash chromatography on silica gel (ethyl acetate:hexane, 1:1+1% methanol) to give the title compound (143 mg).

Step 20B 2-(3,5-dimethylphenyl)-3-[2-(4-phenylpiperazin-1-yl)ethyl]-1H-indole

To a solution of 1-[2-(3,5-dimethylphenyl)-1H-indol-3-yl]-2-(4-phenylpiperazin-1-yl)ethane-1,2-dione (57 mg in 2 mL dry tetrahydrofuran) was added 30 mg of lithium aluminum hydride and the mixture heated to reflux on an oil bath. After 1 hour the mixture was cooled and quenched by the sequential addition of 1 mL water and 4 mL ammonium hydroxide and 5 mL ethyl acetate. The mixture was filtered to remove the solids. The organic portion was washed with brine, dried over magnesium sulfate and the concentrate purified by flash chromatography on silica gel (ethyl acetate:hexane, 1:5) to give the title compound (38 mg). m/e=410 (M+1)

Following a procedure similar to that described above, the following compounds were prepared:

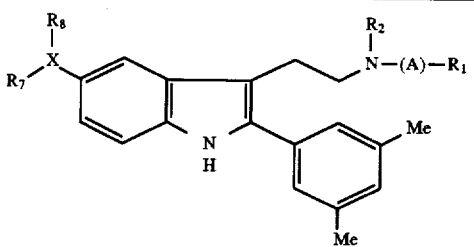

| Example | R₇—X—R₈ | $\overset{R_2}{\underset{N—(A)—R_1}{\|}}$ | m/e |
|---|---|---|---|
| 20A | H | 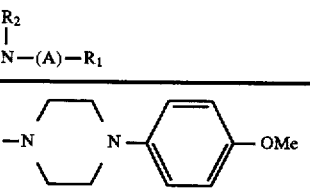 | 440 (M + H) |
| 20B | H | 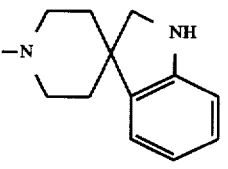 | — |
| 20C | H | 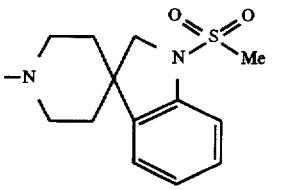 | 514 (M + H) |
| 20D | H | 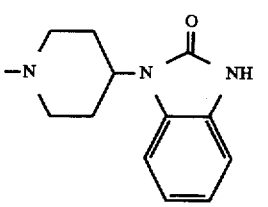 | 465 (M + H) |
| 20E | H | 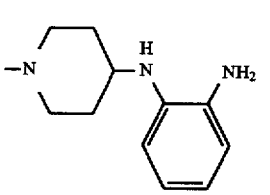 | 439 (M + H) |

-continued

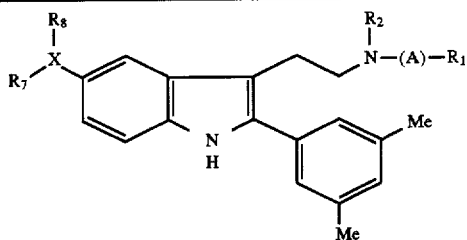

| Example | $R_7-X-R_8$ | $\underset{N-(A)-R_1}{\overset{R_2}{|}}$ | m/e |
|---|---|---|---|
| 20F | $NHC(O)-N(Et)_2$ | [piperidine with phenyl and COOEt] | |
| 20G | $NHC(O)-N(Et)_2$ | [piperidine with phenyl and COOH] | |
| 20H | H | [piperazine-CH2-biphenyl-NHS(O)2-tBu] | 635 (M + H) |

What is claimed is:

1. A compound of the formula

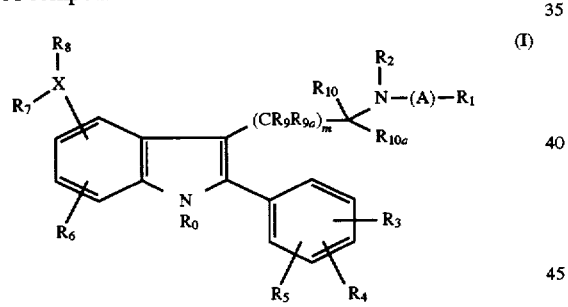

(I)

wherein

A is $C_1-C_6$ alkyl, substituted $C_1-C_6$ alkyl, $C_3-C_7$ cycloalkyl, substituted $C_3-C_7$ cycloalkyl, $C_3-C_6$ alkenyl, substituted $C_3-C_6$ alkenyl, $C_3-C_6$ alkynyl, substituted $C_3-C_6$ alkynyl, $C_1-C_6$ alkoxy, or $C_0-C_5$ alkyl-S(O)$_n$—$C_0-C_5$ alkyl, $C_0-C_5$ alkyl-O—$C_0-C_5$ alkyl, $C_0-C_5$ alkyl-NR$_{18}$—$C_0-C_5$ alkyl where $R_{18}$ and the $C_0-C_5$ alkyl can be joined to form a ring,

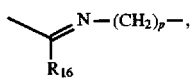

or a single bond;

$R_0$ is hydrogen, $C_1-C_6$ alkyl, substituted $C_1-C_6$ alkyl, wherein the substituents are as defined below; aryl, substituted aryl, aralkyl or substituted aralkyl, wherein the substituents are as defined for $R_3$, $R_4$ and $R_5$;

$R_1$ is

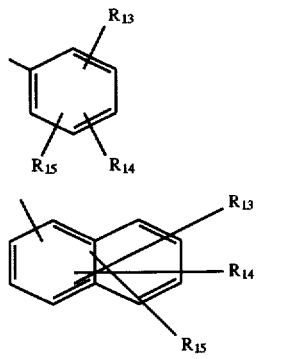

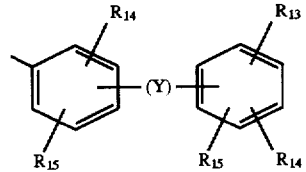

wherein:

Y is B, C or a bond;

B is O, S(O)$_n$, C(O), NR$_{18}$ or C(R$_{11}$R$_{12}$)$_p$

C is B(CH$_2$)$_p$—;

$R_2$ is hydrogen, $C_1-C_6$ alkyl, substituted $C_1-C_6$ alkyl, aralkyl, substituted aralkyl, aryl, substituted aryl, alkyl —OR$_{11}$, $C_1-C_6$(NR$_{11}$R$_{12}$), $C_1-C_6$(CONR$_{11}$R$_{12}$) or C(NR$_{11}$R$_{12}$)NH;

$R_2$ and A taken together form a ring of 5–7 atoms;

$R_3$, $R_4$ and $R_5$ are independently hydrogen, $C_1-C_6$ alkyl, substituted $C_1-C_6$ alkyl, $C_2-C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_3$ and $R_4$ taken together form a carbocyclic ring of 3–7 carbon atoms or a heterocyclic ring containing 1–3 heteroatoms selected from N, O and S;

$R_6$ is hydrogen, $C_1$–$C_6$ alkyl, substituted $C_1$–$C_6$ alkyl, aryl, substituted aryl, $C_1$–$C_3$ perfluoroalkyl, CN, $NO_2$, halogen, $R_{11}O(CH_2)_p$—, $NR_{12}C(O)R_{11}$, $NR_{12}C(O)NR_{11}R_{12}$ or $SO_nR_{11}$;

$R_7$ is hydrogen, $C_1$–$C_6$ alkyl, or substituted $C_1$–$C_6$ alkyl, unless X is hydrogen or halogen, then $R_7$ is absent;

$R_8$ is hydrogen, $C(O)OR_9$, $C(O)NR_{11}R_{12}$, $NR_{11}R_{12}$, $C(O)R_{11}$, $NR_{12}C(O)R_{11}$, $NR_{12}C(O)NR_{11}R_{12}$, $NR_{12}S(O)_2R_{11}$, $NR_{12}S(O)_2NR_{11}R_{12}$, $OC(O)R_{11}$, $OC(O)NR_{11}R_{12}$, $OR_{11}$, $SO_nR_{11}$, $S(O)_nNR_{11}R_{12}$, $C_1$–$C_6$ alkyl or substituted $C_1$–$C_6$ alkyl, unless X is hydrogen or halogen, then $R_8$ is absent; or $R_7$ and $R_8$ taken together form a carbocyclic ring of 3–7 atoms;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m 0; or $R_9$ and $R_{9a}$ taken together form a carbocyclic ring of 3–7 atoms or $$\overset{O}{\|}$$

when m 0;

$R_9$ and A taken together form a heterocyclic ring containing 3–7 carbon atoms and one or more heteroatoms when m 0; or $R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a carbocyclic ring of 3–7 atoms or $$\overset{O}{\|};$$

$R_9$ and $R_{10}$ taken together form a carbocyclic ring of 3–7 carbon atoms or a heterocyclic ring containing one or more heteroatoms when m 0; or $R_9$ and $R_2$ taken together form a heterocyclic ring containing 3–7 carbon atoms and one or more heteroatoms when m 0; or $R_{10}$ and $R_2$ taken together form a heterocyclic ring containing 3–7 carbon atoms and one or more heteroatoms;

$R_{10}$ and A taken together form a heterocyclic ring containing 3–7 carbon atoms and one or more heteroatoms; or $R_{11}$ and $R_{12}$ are independently hydrogen , $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl), $SO_2NR_{11}(C_1$–$C_6$ alkyl), $SO_2NR_{11}$(substituted $C_1$–$C_6$ alkyl), $SO_2NR_{11}$(aryl), $SO_2NR_{11}$(substituted aryl), $SO_2NR_{11}(C_1$–$C_3$ perfluoroalkyl); $SO_2NR_{11}(C(O)C_1$–$C_6$ alkyl), $SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl), $S(O)_n$(substituted $C_1$–$C_6$ alkyl), $S(O)_n$(aryl), $S(O)_n$(substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_{16}$ is hydrogen, $C_1$–$C_6$ alkyl, substituted $C_1$–$C_6$ alkyl, or $N(R_{11}R_{12})$;

$R_{18}$ is hydrogen, $C_1$–$C_6$ alkyl, substituted $C_1$–$C_6$ alkyl, $C(O)OR_9$, $C(O)NR_{11}R_{12}$, $C(O)R_{11}$, $S(O)NR_{11}$;

X is hydrogen, halogen, N, O, $S(O)_n$, $C(O)$, $(CR_{11}R_{12})_p$, $C_2$–$C_6$ alkenyl, substituted $C_2$–$C_6$ alkenyl, $C_2$–$C_6$ alkynyl, or substituted $C_2$–$C_6$ alkynyl; when X is hydrogen or halogen, $R_7$ and $R_8$ are absent; when X is O, $S(O)_n$, $C(O)$, or $CR_{11}R_{12}$ only $R_7$ or $R_8$ is possible;

m is 0–3;

n is 0–2;

p is 0–4; and the alkyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl and aralkyl substituents are as defined for $R_3$, $R_4$ and $R_5$;

with the proviso that at most one of $R_3$, $R_4$ and $R_5$ is hydrogen;

or a pharmaceutically acceptable addition salt and/or hydrate thereof, or where applicable, a geometric or optical isomer or racemic mixture thereof.

2. The compound of claim 1 of the structural formula

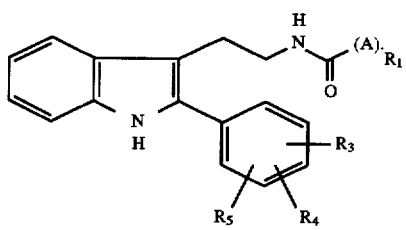

wherein $R_1$, $R_3$, $R_4$, $R_5$ and A are as indicated in the table below:

| $R_1$ | $R_3$, $R_4$, $R_5$ | $(CH_2)n = A$ |
|---|---|---|
| Ph-4-O—$CH_2$—Ph | 3,4-OMe | 3 |
| Ph-4-OH | 3,4-OMe | 3 |

85
-continued

| $R_1$ | $R_3, R_4, R_5$ | $(CH_2)n = A$ |
|---|---|---|
| Ph-4-OH | 3,4-OMe | 1 |
| Ph-3,4-Cl,Cl | 3,4-OMe | 1 |
| Ph-4-F | 3,4-OMe | 1 |
| Ph-4-NO$_2$ | 3,4-OMe | 3 |
| Ph-4-NH$_2$ | 3,4-OMe | 3 |
| Ph-4-NO$_2$ | 3,4-OMe | 1 |
| Ph-4-NH$_2$ | 3,4-OMe | 1 |
| Ph-4-OH | 3,5-OMe | 3 |
| Ph-4-OH | 3-Ph | 3 |
| Ph-4-NH—COO-tBu | 3,5-Me | 3 |
| Ph-4-NH$_2$ | 3,5-Me | 3 |
| Ph-4-NO$_2$ | 3,5-Me | 3 |
| Ph-4-OH | 3-SCH$_3$, 5-CH$_3$ | 3 |
| Ph-4-SO$_2$NH$_2$ | 3,5-Me | 0 |
| Ph-4-OH | 3,4-OMe | 2 |

3. The compound of claim 1 of the structural formula

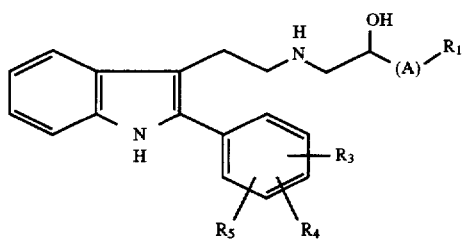

wherein $R_1$, $R_3$, $R_4$, $R_5$ and A are as indicated in the table below:

| $R_1$ | $R_3, R_4, R_5$ | A |
|---|---|---|
| Ph-4-OH | 3,4-OMe | (S) CH$_2$—O |
| Ph-4-OH | 4-OMe | (S) CH$_2$—O |
| Ph | 3,4-OMe | (S) CH$_2$—O |
| Ph-4-OH | 3,4-OMe | (S) CH$_2$—CH$_2$ |
| Ph-4-OH | 3,4-OMe | (R) CH$_2$ |
| Ph-3-F, 4-NH2 | 3,4-OMe | (S) CH$_2$—O |
| Ph-4-NHAc | 3,4-OMe | (S) CH$_2$—O |
| Ph-4-NH2 | 3,4-OMe | (S) CH$_2$—O |
| Ph-4-OH | 3,4-OMe | (R) CH$_2$—O |
| Ph-4-F | 3,4-OMe | (S) CH$_2$—O |
| Ph-4-Cl, 3-NH$_2$ | 3,4-OMe | (S) CH$_2$—O |
| Ph-4-O—CH$_2$—Ph, 3-NH—COCH$_3$ | 3,4-OMe | (S) CH$_2$—O |
| Ph-4-OH, 3-NHCOCH$_3$ | 3,4-OMe | (S) CH$_2$—O |
| Ph-3-CN | 3,4-OMe | (S) CH$_2$—O |
| Ph-3-CH$_2$OH | 3,4-OMe | (S) CH$_2$—O |
| Ph-3-F | 3,4-OMe | (S) CH$_2$—O |
| Ph-3-CH$_2$NH$_2$ | 3,4-OMe | (S) CH$_2$—O |
| Ph-2-F | 3,4-OMe | (S) CH$_2$—O |
| Ph-3-OCH$_2$—Ph | 3,5-Me | (R,S) CH$_2$—O |
| Ph-4-OH | 3,5-Me | (R,S) CH$_2$—O |
| Ph-3-Cl | 3,5-Me | (S) CH$_2$—O |
| Ph-3-CN | 3,5-Me | (S) CH$_2$—O |
| Ph-3-CH$_2$OH | 3,5-Me | (S) CH$_2$—O |

4. The compound of claim 1 of the structural formula

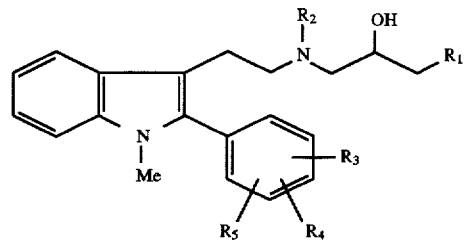

wherein $R_1$, $R_2$, $R_3$, $R_4$ and $R_5$ are as indicated in the table below:

| $R_1$ | $R_3, R_4, R_5$ | $R_2$ |
|---|---|---|
| Ph-4-OCH$_2$—Ph | 3,4-OMe | Me |
| Ph-4-OCH$_2$—Ph | 3,4-OMe | H |
| Ph-OH | 3,4-OMe | Me |
| Ph-OH | 3,4-OMe | H |

5. The compound of claim 1 of the structural formula

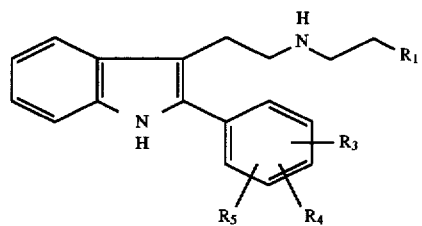

wherein $R_1$, $R_3$, $R_4$ and $R_5$ are as indicated in the table below:

| $R_1$ | $R_3, R_4, R_5$ |
|---|---|
| Ph-3-F, 4-OH | 3,4-OMe |
| Ph-4-OH | 3,4-OMe |
| Ph-3,4-Cl | 3,4-OMe |
| Ph-4-F | 3,4-OMe |
| Ph-4-Cl | 3,4-OMe |
| Ph-4-OH | 3,5-Me |
| Ph-4-NO$_2$ | 3,4-OMe |
| Ph-4-NH$_2$ | 3,4-OMe |

6. The compound of claim 1 of the structural formula

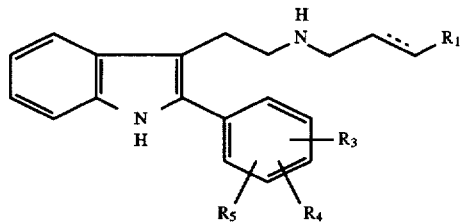

wherein $R_1$, $R_3$, $R_4$ and $R_5$ are as indicated in the table below:

| $R_1$ | $R_3, R_4, R_5$ |
|---|---|
| Ph-3-NH$_2$,4-OH | 3,4-OMe |
| Ph-4-OH | 3,5-Me |

87
-continued

| $R_1$ | $R_3, R_4, R_5$ |
|---|---|
| Ph-4-SO$_2$NH$_2$ | 3,5-Me |
| Ph-4-CH$_2$OH | 3,5-Me |
| Ph-4-COOMe | 3,5-Me |
| Ph-4-NHSO$_2$Me | 3,5-Me |
| Ph-4-Br(trans) | 3,4-OMe |
| Ph-4-OH | 3,5-Me |

7. The compound of claim 1 of the structural formula

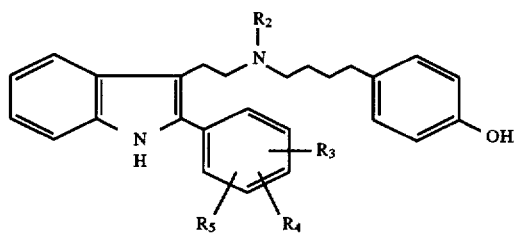

wherein $R_2$, $R_3$, $R_4$ and $R_5$ are as indicated in the table below:

| $R_2$ | $R_3$–$R_5$ |
|---|---|
| CH$_3$ | 3,4-OMe |
| (CH$_2$)$_4$—Ph(4-OH) | 3,5-Me |
| (CH$_2$)CONH$_2$ | 3,5-Me |
| (CH$_2$)$_2$NH$_2$ | 3,5-Me |
| (CNH)NH$_2$ | 3,5-Me |
| (CNH)NH(CNH)NH$_2$ | 3,5-Me |
| CH$_3$ | 3,5-Me |
| (CH$_2$)$_4$OH | 3,5-Me |

8. The compound of claim 1 of the structural formula

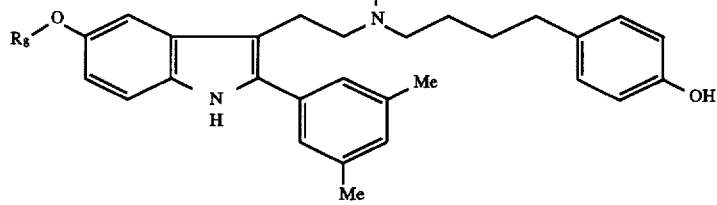

88 wherein $R_2$ and $R_8$ are as indicated in the table below:

| $R_2$ | $R_8$ |
|---|---|
| (CH$_2$)$_4$OH | —CO—NHCH$_2$CH$_3$ |
| (CH$_2$)$_4$OH | —CO—N(CH$_2$CH$_3$)—CO—NH—Et |
| H | —CO—N(CH$_2$CH$_3$)—CO—NH—Et |
| H | —CO—OCH$_2$CH$_3$ |
| H | —CO—NH—Me |
| H | —CO—N—(CH$_3$)$_2$ |
| H | —CO—NH—Ph |
| H | —CO—NH—(CH$_2$)$_2$CH$_3$ |
| H | —CO—NHCH$_2$CH$_3$ |

9. The compound of claim 1 of the structural formula

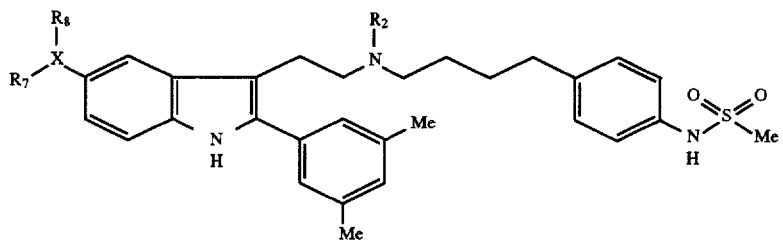

wherein $R_2$ and $XR_7R_8$ are as indicated in the table below:

| $R_6$ | $R_2$ | X–$R_7R_8$ |
|---|---|---|
| H | H | NH–COOCH$_2$Ph |
| H | CH$_2$Ph | NH–COO–Et |
| H | H | NH–COO–Et |
| H | H | NH–CO–N(CH$_2$CH$_3$)$_2$ |
| H | H | N(CH$_2$CH$_3$)CO–N(CH$_2$CH$_3$)$_2$ |
| H | H | NH–CO-Cyclopropyl |
| H | H | NH–CO–Ph |
| H | H | 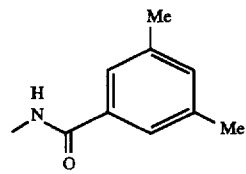 |

| $R_6$ | $R_2$ | $X-R_7R_8$ |
|---|---|---|
| H | H | ![3,5-bis(CF3)benzamide] N-methyl-3,5-bis(trifluoromethyl)benzamide |
| H | H | NH—CO—Me |
| H | H | ![3,5-difluorobenzamide] N-methyl-3,5-difluorobenzamide |
| H | H | NH—CO—CH(Me)—NH—CO—Me |
| H | H | N(Me)—CO—Ph |
| H | H | N(Me)—CO—Me |
| H | H | NH—SO$_2$Me |
| H | H | N-methyl-4-methoxybenzamide |
| H | H | N-methyl-3-methoxybenzamide |

| $R_6$ | $R_2$ | $X-R_7R_8$ |
|---|---|---|
| H | H | NH—CO—NH(CH$_2$CH$_3$) |
| H | H | NH—CO—CH$_2$CH$_3$ |
| H | H | NH—CO—NHMe |
| H | H | NH—CO—NH(CH$_2$CH$_2$CH$_3$) |
| H | H | NH—CO—CH(CH$_3$)$_2$ |
| H | H | NH—CO—NH—CH(CH$_3$)$_2$ |
| H | H | NH—CO—NH-(cyclopropyl) |
| H | H | NH—SO$_2$—(CH$_2$CH$_2$CH$_3$) |
| H | H | NH—SO$_2$—NH—(CH$_2$CH$_3$) |
| H | H | SCH$_3$ |
| H | H | S(O)CH$_3$ |
| H | H | S(O)$_2$CH$_3$ |
| H | H | S(O)$_2$NH$_2$ |
| 6-Cl | H | * |
| 6-Cl | H | NH—CO—NH-(cyclopropyl) |
| H | H | NH—CO—N(CH$_3$)$_2$ |

* = NO$_2$

10. The compound of claim 1 of the structural formula

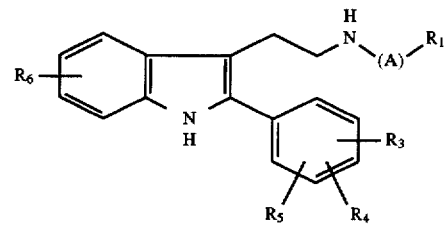

wherein $R_1$, $R_3$, $R_4$, $R_5$, $R_6$ and A are as indicated in the table below:

| $R_1$ | $R_3-R_5$ | $R_6$ | $(CH_2)_n = (A)$ |
|---|---|---|---|
| Ph-4-O—CH$_2$—Ph | 3,4-OMe | | 4 |
| Ph-4-OH | 3,4-OMe | | 4 |
| Ph-4-OH | 3,4-OMe | | 1 |
| Ph-4-NO$_2$ | 3,4-OMe | | 4 |
| Ph-4-NH$_2$ | 3,4-OMe | | 4 |
| Ph-4-OCH$_3$ | 3-OCH$_2$(Ph-3-OMe) | | 4 |
| Ph-4-OH | 3,4-OMe | | 5 |
| Ph-4-OH | 3,5-CF3 | | 4 |
| Ph-4-OH | 3,4-OMe | | 6 |
| Ph-4-OCH$_3$ | 3,4-OMe | | 4 |
| Ph-4-OH | 2-Me | | 4 |
| Ph-4-OH | 2,4-Cl | | 4 |
| Ph-4-OH | 4-F | | 4 |
| Ph-4-OH | 4-Me | | 4 |
| Ph-4-OH | 3-Cl,4-F | | 4 |
| Ph-4-OH | 3,5-Cl | | 4 |
| Ph-4-OH | — | | 4 |
| Ph-4-OH | 3,5-Me | | 4 |
| Ph-4-OH | 3-Me | | 4 |
| Ph-4-OH | 2,6-Me | | 4 |
| Ph-4-OH | 3-OMe | | 4 |
| Ph-4-OH | 3,5-OMe | | 4 |
| Ph-4-OCH$_3$ | 3,5-Me | | 4 |
| Ph-4-OH | 3,5-Me | 5-Cl | 4 |
| Ph-4-OH | 3,5-Me | 5-Me | 4 |
| Ph-4-OH | 3,5-Me | | 5 |
| Ph-4-OH | 3,5-Me | 5-OBn | 4 |
| Ph-4-OH | 2,3-Me | | 4 |
| Ph-4-OH | 3-N(Me)$_2$ | | 4 |
| Ph-4-OH | 3,5-Me | | 6 |
| Ph-4-OH | 2,5-Me | | 4 |
| Ph-4-OH | 3,5-Me | 7-Me | 4 |
| Ph-4-OH | 3,5-Me | | 1 |

-continued

| R₁ | R₃—R₅ | R₆ | (CH₂)ₙ = (A) |
|---|---|---|---|
| Ph-4-OH | 3,5-Me | 5-OMe | 4 |
| Ph-4-OH | 3-OCH₂—Ph | | 4 |
| Ph-4-OH | 3-CH(Me)OBn | | 4 |
| Ph-4-OH | 3-Et | | 4 |
| Ph-4-NO₂ | 3,5-Me | | 4 |
| Ph-4-OH | 3-CH(Me)OH | | 4 |
| Ph-4-OH | 3,5-Me | 6-NH—C(O)CH₃ | 4 |
| Ph-4-OCH₃ | 3-O—CH₂Ph | | 4 |
| Ph-4-NH₂ | 3,5-Me | | 4 |
| Ph-4-NH—COCH₃ | 3,5-Me | | 4 |
| Ph-4-NHSO₂Ph | 3,5-Me | | 4 |
| Ph-4-NHSO₂Me | 3,5-Me | | 4 |
| Ph-4-OMe | 3-OCH₂(Ph-3-OMe) | | 4 |
| Ph-4-OH | 3-SMe | | 4 |
| Ph-4-OH | 3-SMe, 5-Me | | 4 |
| Ph-4-OH | 3,5-Me | 6-Cl | 4 |
| Ph-4-SO₂NH₂ | 3,5-Me | | 1 |
| Ph-4-OH | 3,5-Me | 4-Cl | 4 |
| Ph-4-OH | 3-S(O)Me | | 4 |
| Ph-4-OH | 3-S(O)Me, 5-Me | | 4 |
| Ph-4-OH | 3-SO₂Me | | 4 |
| Ph-4-OH | 3-SO₂Me, 5-Me | | 4 |
| Ph-NHSO₂CF₃ | 3,5-Me | | 4 |
| Ph-NHSO₂Et | 3,5-Me | | 4 |
| *trans-4-methylcyclohexyl-Ph-4-OH* | 3,4-OMe | | 0 |
| *cis-4-methylcyclohexyl-Ph-4-OH* | 3,4-OMe | | 0 |
| Ph-4-OH | 3,5-Me | 6-(3,5-dimethylphenyl) | 4 |
| Ph-4-OH | 3-Me, 5-i-Bu | | 4 |
| Ph-4-OH | 3-Me, 5-Pr | | 4 |
| Ph-4-NH₂ | 3,5-Me | 5-NHC(O)—NHEt | 4 |
| Ph-4-NHSO₂-iPr | 3,5-Me | | 4 |
| Ph-4-OH | 3,5-Me | 5-NO₂ | 4 |
| Ph-3,4-OMe | 3,5-Me | | 4 |
| Ph-3,4-OH | 3,5-Me | | 4 |
| Ph-4-OH | 3,5-Me | 5-Br | 4 |
| 2-naphthyl | 3,5-Me | | 4 |
| Ph-4-NHSO₂NHMe | 3,5-Me | | 4 |
| Ph-4-CN | 3,5-Me | | 4 |
| Ph-4-F | 3,5-Me | | 4 |
| Ph-4-OH | 3,5-Me | 5-Ph | 4 |
| Ph-3-Br, 4-NHSO₂—Me | 3,5-Me | | 4 |
| Ph-4-NHCONHMe | 3,5-Me | | 4 |
| Ph-4-OH | 3,5-Me | 5-CH(Me)₂ | 4 |
| Ph-4-SO₂NH₂ | 3,5-Me | | 4 |
| 1-naphthyl-4-OMe | 3,5-Me | | 4 |
| 1-naphthyl-4-OH | 3,5-Me | | 4 |
| Ph-3-F, 4-OMe | 3,5-Me | | 4 |
| Ph-3-F, 4-OH | 3,5-Me | | 4 |
| Ph-4-NHSO₂NHEt | 3,5-Me | | 4 |
| Ph-4-NHCONHEt | 3,5-Me | | 4 |
| Ph-4-NHSO₂Me | 3,5-Me | 5-SO₂Me | 5 |

-continued

| R₁ | R₃—R₅ | R₆ | (CH₂)ₐ = (A) |
|---|---|---|---|
| Ph-4-NHSO₂Me | 3,5-Cl | 5-N(Et)CO—N(Et)₂ | 4 |
| Ph-4-OH | 3,5-Me | 5-F | 4 |

11. The compound of claim 1 of the structural formula

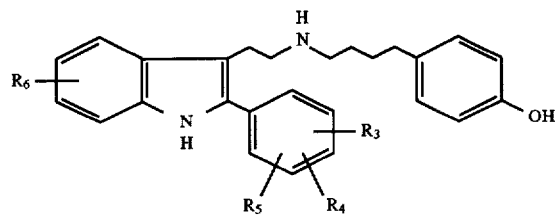

wherein R₃, R₄, R₅ and R₆ are as indicated in the table below:

| R₃–R₅ | R₆ |
|---|---|
| 2-(CH)₄-3 | H |
| 3-(CH)₄-4 | H |
| 3-(CH—CH—N(Me))-4 | H |
| 2-(CH)₄-3 | 5-OBn |
| 2-(CH)₄-3 | 5-OH |
| 2-(CH)₄-3 | 6-F |
| 2-(CH)₄-3, 5-Me | H |

12. The compound of claim 1 of the structural formula

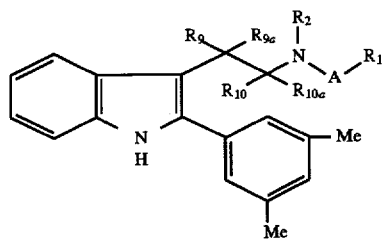

wherein R₁, R₂, R₉, R₉ₐ, R₁₀, R₁₀ₐ and A are as indicated in the table below:

| R₁ | R₂ | R₉ | R₉ₐ | R₁₀ | R10a | A |
|---|---|---|---|---|---|---|
| Ph-4-OH | H | H | H | CH₃ | H | 4 |
| Ph-4-OH | H | Ph | H | H | H | 4 |
| Ph-4-OH | | —CH₂CH₂— | H | H | H | 4 |
| Ph-4-OH | H | CH₃ | H | H | H | 2 |
| Ph-4-NHSO₂Me | H | CH₃ | H | H | H | 4 |
| Ph-4-OH | H | H | H | CH₃ | H | 2 |
| Ph-4-OH | H | H | H | CH₃ | CH₃ | 4 |
| Ph-4-NHSO₂Me | H | CH₃ | H | H | H | 2 |
| Ph-4-OH | H | CH₃ | H | H | H | 4 |

13. The compound of claim 1 of the structural formula

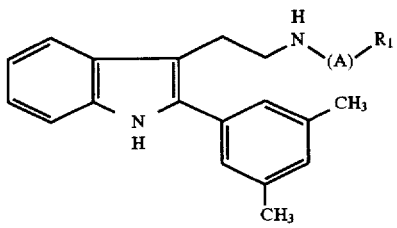

wherein R₁ and A are as indicated in the table below:

| R₁ | (A) |
|---|---|
| Ph-4-O-tBu | —CH₂—CH₂—O—CH₂— |
| Ph-4-OH | —(CH₂)₃—C(CH₃)₂—Ph-4-OH |
| Ph-4-OH | —CH₂—CH₂—CHMe—CH₂— |
| Ph-4-OH | —CH₂—CH(CH₃)₂— |
| Ph-4-OH | —CNH—NH—(CH₂)₂— |
| Ph-4-OH | —(CH₂)₃—CH(O—CH₂—CH₂—OH)— |
| Ph-4-OH | —(CH₂)₃—C(O—CH₂—CH₂—O)— |
| 1-(naphthyl-4-OH) | —CH₂—C(Me)₂— |
| Ph-4-OH | -⬡- |
| Ph-4-OH | —CO—NHCH₂CH₂— |

14. The compound of claim 1 of the structural formula

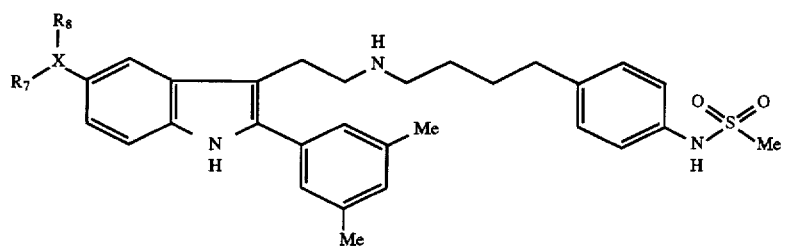
wherein $XR_7R_8$ is as indicated in the table below:
| $X-R_7R_8$ |
|---|
| $CH_2COOEt$ |
| $CH_2CON(Me)_2$ |
| $CH(Me)COOEt$ |
| $C(Me)_2COOEt$ |
| $CH(Me)CON(Et)_2$ |
| $C(Me)_2CON(Me)_2$ |
| $C(Me)_2CON(Pr)_2$ |
| $CH_2CON(Et)_2$ |
| $C(Me)_2CON(Et)_2$ |
15. The compound of claim 1 of the structural formula
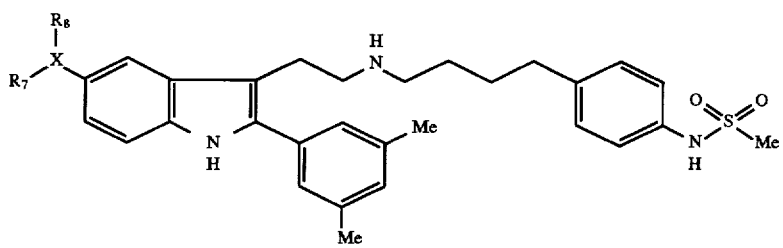
wherein $XR_7R_8$ is as indicated in the table below:
| $X-R_7R_8$ |
|---|
| COOEt |
| CO—N(CH$_2$CH$_2$OH) |
| CO—NHEt |
| CO—NH-cyclopropyl |
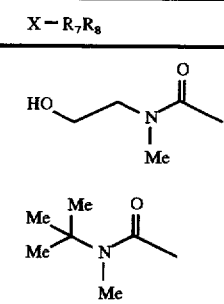
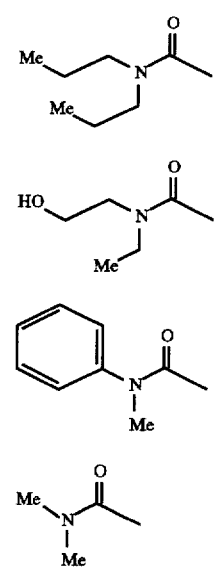

| X—R₇R₈ |
| --- |

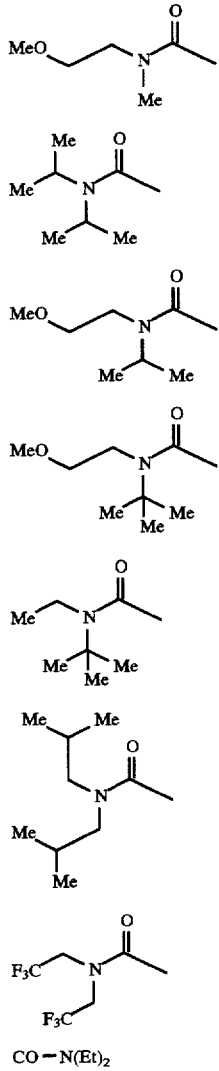

CO—N(Et)₂

16. The compound of claim 1 of the structural formula wherein X—R₇R₈, R₉, R₉ₐ, R₁₀, R₁₀ₐ and A are as indicated in the table below:

| X—R₇R₈ | R₉, R₉ₐ:R₁₀, R₁₀ₐ | (CH₂)n = A |
| --- | --- | --- |
| NH—CON(Et)₂ | Me, H:H, H | 4 |
| NH—CO—Ph | Me, H:H, H | 4 |
| NH—CO—N(Me)₂ | Me, H:H, H | 2 |
| NH—CO—N(Me)₂ | Me, H:H, H | 4 |
| N(CH₂Ph)₂ | Me, H:Me, H | 4 |
| NHC(O)Ph | CH₂CH₂OH, H:H, H | 4 |
| SO₂Me | Me,H:H,H | 4 |
| NHC(O)Ph | CH₂CH₂OMe, H:H, H | 4 |
| O—CH₂Ph | H, H:Me, Me | 4 |

17. The compound of claim 1 of the structural formula

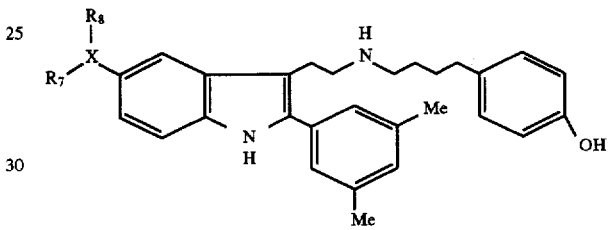

wherein X—R₇R₈ are as indicated in the table below:

| X—R₇R₈ |
| --- |
| COO—CH₂CH₃ |
| COOH |
| CO—N(CH₂CH₃)₂ |
| CO—NH—CH₂Ph |
| CO—N(CH₃)₂ |
| CO—N(iBu)₂ |

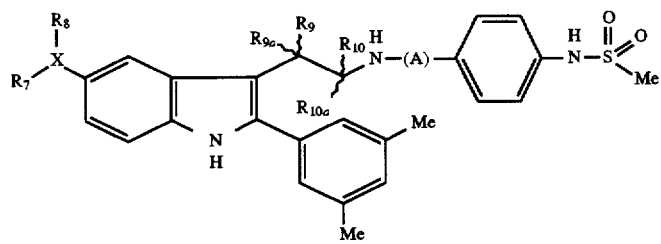

18. The compound of claim 1 of the structural formula

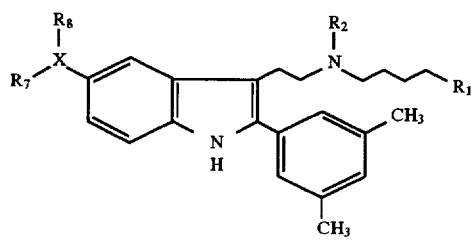

wherein $R_1$, $R_2$ and $XR_7R_8$ are as indicated in the table below:

| $R_1$ | $X-R_7R_8$ | $R_2$ |
|---|---|---|
| Ph-4-NH(SO$_2$Me)—COEt | NHCOEt | |
| Ph-4-NHSO$_2$CH$_2$—C(O)Me | SO$_2$CH$_2$C(O)Me | |
| Ph-4-NHSO$_2$CH$_2$—C(O)Me | SO$_2$Me | |
| Ph-4-SONHMe | COOEt | |
| Ph-4-NO$_2$ | COOEt | |
| Ph-4-NHSO$_2$Me | CON(Et)$_2$ | Et |
| Ph-4-SO$_2$NHMe | CON(Et)$_2$ | |
| Ph-4-SO$_2$NHMe | CON(iBu)$_2$ | |
| Ph-4-SO$_2$NHMe | CON(cyclohexyl)Et | |
| Ph-4-NO$_2$ | CON(iBu)$_2$ | |
| Ph-4-NH$_2$ | CON(iBu)$_2$ | |
| Ph-4-SMe | COOEt | |
| Ph-4-SMe | CON(Et)$_2$ | |
| Ph-4-S(O)Me | CON(Et)$_2$ | |
| Ph-4-S(O)$_2$Me | CON(Et)$_2$ | |
| Ph-4-SMe | CON(iBu)$_2$ | |
| Ph-4-S(O)Me | CON(iBu)$_2$ | |
| Ph-4-S(O)$_2$Me | CON(iBu)$_2$ | |
| Ph-4-NH[C=N(CONH2)]NHMe | CON(iBu)$_2$ | |
| Ph-4-NH[C=N(CN)]NHMe | CON(iBu)$_2$ | |
| Ph-4-F | CON(iBu)$_2$ | |
| Ph-4-SO2N(Me)2 | COOEt | |
| Ph-4-SO2N(Me)2 | CON(iBu)$_2$ | |
| Ph-4-SO2N(Me)2 | CON(Et)$_2$ | |
| Ph-4-SO2N(Me)2 | CON(Et)cyclohexyl | |

19. The compound of claim 1 of the structural formula

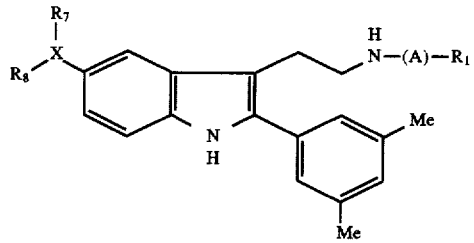

wherein A, $R_1$ and X—$R_7R_8$ are as indicated in the table below:

| X—$R_7R_8$ | —(A)—$R_1$ |
|---|---|
| H | (2-nitro-biphenyl-ethyl) |
| H | (2-amino-biphenyl-ethyl) |
| H | (biphenyl-OH-ethyl) |
| NHCON(Et)$_2$ | (biphenyl-OH) |
| SO$_2$Me | (butyl-CH(OH)-Ph-SO$_2$Me) |

20. The compound of claim 1 of the structural formula

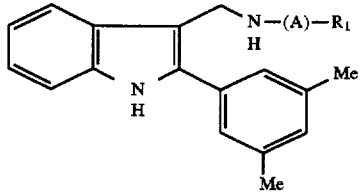

wherein A and $R_1$ are as indicated in the table below:

| $R_1$ | (CH$_2$)n = A |
|---|---|
| Ph-4-OMe | 4 |
| Ph-4-OH | 4 |
| Ph-4-OH | 3 |
| Ph-4-OH | 2 |

21. The compound of claim 1 of the structural formula

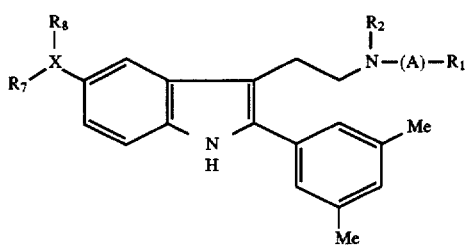

wherein A, $R_1$, $R_2$ and X—$R_7R_8$ are as indicated in the table below:

| X—$R_7R_8$ | $\underset{N-(A)-R_1}{\overset{R_2}{\mid}}$ |
|---|---|
| H | —N(piperazinyl)—N-(4-methoxyphenyl) |
| H | —N(piperidinyl) with NH-2-aminophenyl substituent |
| H | —N(piperidinyl) with N(SO₂Me)-2-aminophenyl substituent |
| H | —N(piperidinyl)—N(C(O))—2-NH-phenyl |
| H | —N(piperidinyl)—N(H)—2-NH₂-phenyl |
| NHC(O)N(Et)₂ | —N(piperidinyl) with phenyl and COOEt |
| NHC(O)N(Et)₂ | —N(piperidinyl) with phenyl and COOH |

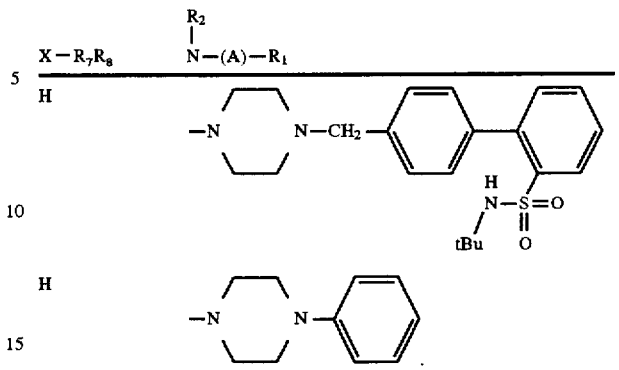

22. The compound as defined in claim 1 which is
   a) N-[2-[2-(3,4-dimethoxyphenyl)-1H-indol-3-yl]ethyl]-3-(4-hydroxyphenyl)propionamide;
   b) 3-[3-[2-[2-(3,5-dimethylphenyl)-1H-Indol-3-yl]ethylamino]-2-hydroxypropoxy]phenol;
   c) (S)-4-[3-[2-[2-(3,5-dimethylphenyl)-1-methyl-1H-indol-3-yl]ethylamino]-2-hydroxypropoxy]phenol;
   d) [2-[2-(3,4-dimethoxyphenyl)-1H-indol-3-yl]ethyl]-[2-(4-nitrophenyl)ethyl]amine;
   e) [2-[2-(3,4-dimethoxyphenyl)-1H-indol-3-yl]ethyl]-[2-(4-aminophenyl)ethyl]amine;
   f) [3-(4-bromophenyl)allyl]-[2-[2-(3,4-dimethoxyphenyl)-1H-indol-3-yl]ethyl]amine;
   g) 4-[3-[2-[[2-(3,4-dimethoxyphenyl)-1H-indol-3-yl]ethyl]amino]propyl]phenol;
   h) 2-[[2-[2-(3,5-dimethylphenyl)-1H-indol-3-yl]ethyl]-[4-(4-hydroxyphenyl)-butyl]amino]acetamide;
   i) 4-[4-[(2-aminoethyl)-[2-[2-(3,5-dimethylphenyl)-1H-indol-3-yl]ethyl]amino]butyl]phenol;
   j) N-[2-[2-(3,5-dimethylphenyl)-1H-indol-3-yl]ethyl]-N-[4-(4-hydroxyphenyl)butyl]guanidine;
   k) N-[2-[2-(3,5-dimethylphenyl)-1H-indol-3-yl]ethyl]-N-[4-(4-hydroxyphenyl)butyl]guanidino-guanidine;
   l) 4-[4-[[2-[2-(3,5-dimethylphenyl)-1H-indol-3-yl]ethyl]methylamino]butyl]phenol;
   m) 4-[4-[[2-[2-(3,5-dimethylphenyl)-1H-indol-3-yl]ethyl]-(4-hydroxybutyl)amino]butyl]phenol;
   n) Propylcarbamic acid 2-(3,5-dimethylphenyl)-3-[2-[4-(4-hydroxyphenyl)butylamino]ethyl]-1H-indol-5-yl ester;
   o) Ethylcarbamic acid 2-(3,5-dimethylphenyl)-3-[2-[4-(4-hydroxyphenyl)butylamino]ethyl]-1H-indol-5-yl ester;
   p) N-[4-(4-{2-[2-(3,5-dimethylphenyl)-5-(3,3-dimethylureido)-1H-indol-3-yl]ethylamino}butyl)phenyl]methanesulfonamide;
   q) 5-[(N,N-Diethylcarbamoyl)methyl]-2-(3,5-dimethylphenyl)-3-[2-[[4-[4-(methanesulfonamido)phenyl]butyl]amino]ethyl]indole;
   r) 5-[1-(N,N-Diethylcarbamoyl)-1-methylethyl]-2-(3,5-dimethylphenyl)-3-[2-[[4-[4-(methanesulfonamido)phenyl]butyl]amino]ethyl]indole; and
   s) 5-(N,N-Diethylcarbamoyl)-2-(3,5-dimethylphenyl)-3-[2-[[4-[4-(methanesulfonamido)phenyl]butyl]amino]ethyl]indole.

23. A pharmaceutical composition which comprises an effective amount of a compound as defined in claim 1 and a pharmaceutically acceptable carrier therefor.

24. A method for antagonizing gonadotropin-releasing hormone in a subject in need thereof which comprises administering to said subject an effective amount of a compound as defined in claim 1 to a subject suffering from a gonadotropin-releasing hormone derived disorder.

25. A method according to claim 24 wherein the gonadotropin-releasing hormone derived disorder is a sex-hormone related condition.

26. A method according to claim 24 wherein the gonadotropin-releasing hormone derived disorder is a sex hormone dependent cancer, benign prostatic hypertrophy or myoma of the uterus.

27. A method according to claim 26 wherein the sex hormone dependent cancer is selected from the group consisting of prostatic cancer, uterine cancer, breast cancer and pituitary gonadotrophe adenomas.

28. A method according to claim 25 wherein the sex hormone related condition is selected from the group consisting of endometriosis, polycystic ovarian disease, uterine fibroids and precocious puberty.

29. A method for preventing pregnancy in a subject in need thereof which comprises administering an effective amount of a compound as defined in claim 1.

30. A method for treating lupus erythematosis in a subject in need thereof which comprises administering to said subject an effective amount of a compound as defined in claim 1.

31. A method for treating irritable bowel syndrome in a subject in need thereof which comprises administering to said subject an effective amount of a compound as defined in claim 1.

32. A method for treating premenstrual syndrome in a subject in need thereof which comprises administering to said subject an effective amount of a compound as defined in claim 1.

33. A method for treating hirsutism in a subject in need thereof which comprises administering to said subject an effective amount of a compound as defined in claim 1.

34. A method for treating short stature or a growth hormone deficiency in a subject in need thereof which comprises administering to said subject an effective amount of a compound which stimulates the endogenous production or release of growth hormone and an effective amount of a compound as defined in claim 1.

35. A method for treating sleep disorders such as sleep apnea in a subject in need thereof which comprises administering to said subject an effective amount of a compound as defined in claim 1.

36. A pharmaceutical composition which comprises an inert carrier and an effective amount of a compound which stimulates the endogenous production or release of growth hormone in combination with a compound as defined in claim 1.

37. A pharmaceutical composition made by combining the compound of claim 1 and a pharmaceutically acceptable carrier therefor.

38. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 5,756,507
DATED : May 26, 1998
INVENTOR(S) : Mark Goulet, et al.

It is certified that error appears in the above-identified patent and that said Letters Patent is hereby corrected as shown below:

Column 99, line 30-31 in the table, should read:

"SONHMe" should read --$SO_2NHMe$--.

Signed and Sealed this

Sixth Day of October, 1998

*Attest:*

BRUCE LEHMAN

*Attesting Officer*    *Commissioner of Patents and Trademarks*